US011338059B2

(12) United States Patent
Peyman

(10) Patent No.: US 11,338,059 B2
(45) Date of Patent: *May 24, 2022

(54) METHOD OF CORNEAL AND SCLERAL INLAY CROSSLINKING AND PRESERVATION

(71) Applicant: Gholam A. Peyman, Sun City, AZ (US)

(72) Inventor: Gholam A. Peyman, Sun City, AZ (US)

(*) Notice: Subject to any disclaimer, the term of this patent is extended or adjusted under 35 U.S.C. 154(b) by 157 days.

This patent is subject to a terminal disclaimer.

(21) Appl. No.: 16/717,705

(22) Filed: Dec. 17, 2019

(65) Prior Publication Data

US 2020/0121829 A1 Apr. 23, 2020

Related U.S. Application Data

(63) Continuation-in-part of application No. 16/451,247, filed on Jun. 25, 2019, now Pat. No. 10,881,503,
(Continued)

(51) Int. Cl.
*A61L 27/54* (2006.01)
*A61F 2/14* (2006.01)
*A61L 27/36* (2006.01)

(52) U.S. Cl.
CPC ......... *A61L 27/3687* (2013.01); *A61F 2/142* (2013.01); *A61F 2/1451* (2015.04);
(Continued)

(58) Field of Classification Search
CPC .. A61L 27/3687; A61L 27/3691; A61L 27/54; A61L 2430/16; A61L 2430/40;
(Continued)

(56) References Cited

U.S. PATENT DOCUMENTS 3,760,807 A 9/1973 Neefe
4,563,779 A 1/1986 Kelman
(Continued)

FOREIGN PATENT DOCUMENTS

EP 1616568 A2 1/2016
WO 89/04153 A1 5/1989
(Continued)

OTHER PUBLICATIONS

J. I. Barraquer, "Keratomileusis and Keratophakia for the Correction of Congenital Hypermetropia and Aphakia", Bulletins et Memoires de la Societe Francaise D'Ophthalmologie, vol. 95, pp. 380-390 (1984).
(Continued)

*Primary Examiner* — Paul B Prebilic
(74) *Attorney, Agent, or Firm* — The Law Office of Patrick F. O'Reilly III, LLC

(57) ABSTRACT

A method of corneal and scleral inlay crosslinking and preservation is disclosed herein. The method includes crosslinking at least a portion of a donor cornea or a donor sclera so as to kill cellular elements in the portion of the donor cornea or the donor sclera, and make the portion of the donor cornea or the donor sclera less antigenic to a body portion of a recipient patient in which the portion of the donor cornea or the donor sclera is to be implanted; and storing the cross-linked donor cornea or the donor sclera for a long period of time prior to implanting the portion of the donor cornea or the donor sclera into the body portion of the recipient patient.

19 Claims, 27 Drawing Sheets

Related U.S. Application Data which is a continuation-in-part of application No. 16/414,713, filed on May 16, 2019, now Pat. No. 10,583,221, which is a continuation-in-part of application No. 15/941,641, filed on Mar. 30, 2018, now Pat. No. 10,314,690, which is a continuation-in-part of application No. 15/230,445, filed on Aug. 7, 2016, now Pat. No. 9,937,033, which is a continuation-in-part of application No. 14/709,801, filed on May 12, 2015, now Pat. No. 9,427,355.

(60) Provisional application No. 62/849,941, filed on May 19, 2019, provisional application No. 62/780,404, filed on Dec. 17, 2018, provisional application No. 62/672,161, filed on May 16, 2018, provisional application No. 62/478,914, filed on Mar. 30, 2017, provisional application No. 62/360,281, filed on Jul. 8, 2016, provisional application No. 62/065,714, filed on Oct. 19, 2014, provisional application No. 61/991,785, filed on May 12, 2014.

(52) U.S. Cl.
CPC ........... *A61L 27/3691* (2013.01); *A61L 27/54* (2013.01); *A61L 2430/16* (2013.01); *A61L 2430/40* (2013.01)

(58) Field of Classification Search
CPC .............. A61F 2/142; A61F 2/2451; A61F 2220/0008; A61F 2240/001; A61F 2250/0001; A61F 2250/0067; A61F 2250/0091; A61F 2250/0095
See application file for complete search history.

(56) References Cited

U.S. PATENT DOCUMENTS

| | | | |
|---|---|---|---|
| 4,665,913 A | 5/1987 | L'Esperance, Jr. | |
| 4,718,418 A | 1/1988 | L'Esperance, Jr. | |
| 4,793,344 A | 12/1988 | Cumming et al. | |
| 4,799,931 A | 1/1989 | Lindstrom | |
| 4,840,175 A | 6/1989 | Peyman | |
| 4,842,599 A | 6/1989 | Bronstein | |
| 4,844,242 A * | 7/1989 | Chen | A01N 1/02 206/5.1 |
| 4,903,695 A | 2/1990 | Warner et al. | |
| 4,994,058 A | 2/1991 | Raven et al. | |
| 5,171,318 A | 12/1992 | Gibson et al. | |
| 5,336,261 A | 8/1994 | Barrett et al. | |
| 5,552,452 A | 9/1996 | Khadem | |
| 5,613,982 A * | 3/1997 | Goldstein | A61L 27/507 424/423 |
| 5,702,441 A | 12/1997 | Zhou | |
| 5,964,748 A | 10/1999 | Peyman | |
| 6,102,946 A | 8/2000 | Nigam | |
| 6,110,166 A | 8/2000 | Juhasz | |
| 6,180,687 B1 | 1/2001 | Hammer | |
| 6,197,019 B1 | 3/2001 | Peyman | |
| 6,537,545 B1 | 3/2003 | Karageozian et al. | |
| 6,551,307 B2 | 4/2003 | Peyman | |
| 7,001,374 B2 | 2/2006 | Peyman | |
| 7,004,902 B2 | 2/2006 | Luce | |
| 7,044,945 B2 | 5/2006 | Sand | |
| 7,083,802 B2 | 8/2006 | Peyman | |
| 7,598,288 B2 | 10/2009 | Hellberg et al. | |
| 7,828,844 B2 | 11/2010 | Marmo et al. | |
| 8,632,489 B1 | 1/2014 | Ahmed | |
| 8,911,768 B2 | 12/2014 | Whitcup et al. | |
| 9,249,424 B2 | 2/2016 | Wolf et al. | |
| 9,301,925 B2 | 4/2016 | Xu et al. | |
| 9,370,446 B2 | 6/2016 | Peyman | |
| 9,427,355 B1 | 8/2016 | Peyman | |
| 9,486,357 B2 | 11/2016 | Peyman | |
| 9,814,567 B2 | 11/2017 | Peyman | |
| 9,931,171 B1 | 4/2018 | Peyman | |
| 9,937,033 B1 * | 4/2018 | Peyman | A61F 9/00834 |
| 2001/0027314 A1 | 10/2001 | Peyman | |
| 2002/0006394 A1 | 1/2002 | Redmond et al. | |
| 2002/0071856 A1 | 6/2002 | Dillingham | |
| 2002/0123744 A1 | 9/2002 | Reynard | |
| 2003/0035843 A1 | 2/2003 | Livesey et al. | |
| 2004/0029855 A1 | 2/2004 | Klaveness et al. | |
| 2004/0049174 A1 | 3/2004 | Peyman | |
| 2005/0070942 A1 | 3/2005 | Perez | |
| 2005/0246018 A1 | 11/2005 | Grubbs | |
| 2006/0135477 A1 | 6/2006 | Haitjema | |
| 2006/0166919 A1 | 7/2006 | Shepard et al. | |
| 2007/0135754 A1 | 6/2007 | Akiyama et al. | |
| 2007/0142908 A1 | 6/2007 | Xu | |
| 2007/0255404 A1 | 11/2007 | Pinchuk | |
| 2009/0171305 A1 | 7/2009 | El Hage | |
| 2009/0177139 A1 | 7/2009 | Boyden et al. | |
| 2009/0196903 A1 | 8/2009 | Kliman | |
| 2009/0208577 A1 | 8/2009 | Xu et al. | |
| 2009/0253661 A1 | 10/2009 | Peyman | |
| 2010/0087920 A1 | 4/2010 | Marmo | |
| 2010/0198348 A1 | 8/2010 | Hiles et al. | |
| 2010/0210996 A1 | 8/2010 | Peyman | |
| 2010/0215717 A1 | 8/2010 | Soker et al. | |
| 2011/0076734 A1 | 3/2011 | Zhou et al. | |
| 2011/0152219 A1 | 6/2011 | Stagni et al. | |
| 2011/0166650 A1 | 7/2011 | Busin | |
| 2011/0208300 A1 | 8/2011 | de Juan, Jr et al. | |
| 2011/0250688 A1 | 10/2011 | Hasan | |
| 2012/0203161 A1 | 8/2012 | Herekar | |
| 2012/0226351 A1 | 9/2012 | Peyman | |
| 2012/0245683 A1 | 9/2012 | Christie et al. | |
| 2013/0218167 A1 | 8/2013 | Coffey et al. | |
| 2015/0134049 A1 | 5/2015 | Austen, Jr. et al. | |
| 2015/0223930 A1 | 8/2015 | Shiuey | |
| 2015/0366706 A1 | 12/2015 | Belkin et al. | |
| 2016/0022495 A1 | 1/2016 | Feingold | |
| 2016/0081852 A1 | 3/2016 | Peyman | |
| 2016/0331868 A1 | 11/2016 | Grubbs et al. | |
| 2017/0007395 A1 | 1/2017 | Peyman | |
| 2019/0054183 A1 | 2/2019 | Yang et al. | |

FOREIGN PATENT DOCUMENTS

| | | |
|---|---|---|
| WO | 92/16172 A1 | 10/1992 |
| WO | 01/58495 A2 | 8/2001 |
| WO | 2004/108064 A2 | 12/2004 |
| WO | 2008/055118 A2 | 5/2008 |

OTHER PUBLICATIONS

Wollensak et al., "Riboflavin/Ultraviolet-A-induced Collagen Crosslinking for the Treatment of Keratoconus", American Journal of Ophthalmology, vol. 135, pp. 620-627 (2003).

M. A. Bamashmus, M. F. Saleh, M. A. Awadalla, "Reasons for Not Performing Keratorefractive Surgery in Patients Seeking Refractive Surgery in a Hospital-Based Cohort in Yemen", Middle East Afr J Ophthalmol, Oct.-Dec. 2010;17(4): pp. 349-353.

Goins et al., "Photodynamic biologic tissue glue to enhance corneal wound healing after radial keratotomy" (Nov. 1997), Journal of Cataract and Refractive Surgery, vol. 23, Issue 9, pp. 1331-1338. (Abstract only).

First office action on the merits (Non-Final Rejection) in U.S. Appl. No. 14/709,801, dated Jan. 11, 2016.

Second office action on the merits (Final Rejection) in U.S. Appl. No. 14/709,801, dated May 4, 2016.

Notice of Allowance in U.S. Appl. No. 14/709,801, dated Jul. 19, 2016.

First office action on the merits (Non-Final Rejection) in U.S. Appl. No. 15/230,445, dated Jul. 11, 2017.

Notice of Allowance in U.S. Appl. No. 15/230,445, dated Dec. 4, 2017.

First office action on the merits (Non-Final Rejection) in U.S. Appl. No. 15/816,140, dated Oct. 22, 2018.

(56) References Cited

OTHER PUBLICATIONS

Notice of Allowance in U.S. Appl. No. 15/816,140, dated Feb. 19, 2019.
PCT Form 210, International Search Report for PCT/US2019/030931, dated Jul. 17, 2019.
PCT Form 237, Written Opinion of the International Searching Authority for PCT/US2019/030931, dated Jul. 17, 2019.
Darwish et al. "Subbasal Nerve Fiber Regeneration after LASIK and LASEK Assessed by Noncontact Esthesiometry and in Vivo Confocal Microscopy: Prospective Study." Journal of Cataract & Refractive Surgery, vol. 33, No. 9, Sep. 2007, pp. 1515-1521, doi:https://doi.org/10.1016/j.jcrs.2007.05.023.
Townes-Anderson et al. "Fasudil, a Clinically Used ROCK Inhibitor, Stabilizes Rod Photoreceptor Synapses after Retinal Detachment." Translational Vision Science & Technology, vol. 6, No. 3, ser. 22, Jun. 2017. 22, doi:10.1167/tvst.6.3.22.
Abegunde et al. "Doxycycline plus Ivermectin versus Ivermectin Alone for Treatment of Patients with Onchocerciasis." The Cochrane Database of Systematic Reviews, U.S. National Library of Medicine, Jan. 15, 2016, www.ncbi.nlm.nih.gov/pmc/articles/PMC5029467/.
Hegde et al. "A Skin-Depth Analysis of Integrins: Role of the Integrin Network in Health and Disease." Cell Communication & Adhesion, vol. 20, No. 6, Nov. 2013, pp. 155-169, doi:https:1/doi.org/10.3109/15419061.2013.854334.
Todorich et al. "Simultaneous Dexamethasone Intravitreal Implant and Anti-VEGF Therapy for Neovascular Age-Related Macular Degeneration Resistant to Anti-VEGF Monotherapy." Journal of Vitreoretinal Diseases, vol. 1, No. 1, Jan. 26, 2017, pp. 65-74, doi:10.1177/2474126416683299.
Tao et al. "Treatment of Burn Scars in Fitzpatrick Phototype III Patients with a Combination of Pulsed Dye Laser and Non-Ablative Fractional Resurfacing 1550 Nm Erbium:Glass/1927 Nm Thulium Laser Devices." Scars, Burrns & Healing, SAGE Publications, Feb. 23, 2018, www.ncbi.nlm.nih.gov/pmc/articles/PMC5965338/.
Stepp et al. "Wounding the Cornea to Learn How it Heals." Experimental Eye Research, U.S. National Library of Medicine, Apr. 2014, www.ncbi.nlm.nih.gov/pmc/articles/PMC4072315/.
Loewen. Ocular Surgery News. "How Many Medications Should be Tried to Lower IOP before Moving on to SLT or Glaucoma Filtering Surgery?" Healio Ocular Surgery News, Healio, Oct. 25, 2010, www.healio.com/ophthalmology/glaucoma/news/print/ocular-surgery-news/%7Bd9857d89-570c-4b52-af40-26bfd5273ddc%7D/how-many-medications-should-be-tried-to-lower-iop-before-moving-on-to-slt-or-glaucoma-filtering-surgery.
Li et al. "Intranasal Delivery of FSD-C10, a Novel Rho Kinase Inhibitor, Exhibits Therapeutic Potential in Experimental Autoimmune Encephalomyelitis." Immunology, Blackwell Science Inc, Oct. 2014, www.ncbi.nlm.nih.gov/pmc/articles/PMC4172138/.
First office action on the merits (Non-Final Rejection) in U.S. Appl. No. 15/941,641, dated Sep. 27, 2018.
Notice of Allowance in U.S. Appl. No. 15/941,641, dated Mar. 21, 2019.
First office action on the merits (Non-Final Rejection) in U.S. Appl. No. 16/414,713, dated Oct. 8, 2019.
Notice of Allowance in U.S. Appl. No. 16/414,713, dated Dec. 6, 2019.
Petersen et al., "An Improved Method of Intralamellar Keratoplasty in Rats", (Feb. 1987), Investigative & Visual Science, vol. 28, pp. 281-286, (Year 1987).
First office action on the merits (Non-Final Rejection) in U.S. Appl. No. 16/451,247, dated Apr. 1, 2020.
Notice of Allowance in U.S. Appl. No. 16/451,247, dated Sep. 1, 2020.
"Triton X-100", Sigma-Aldrich Website, Web page <https://www.sigmaaldrich.com/US/en/product/roche/10789704001>, 6 pages, dated at least as early as Dec. 23, 2021, retrieved from Sigma-Aldrich website on Dec. 23, 2021.
"IGEPAL® CA-630", Sigma-Aldrich Website, Web page <https://www.sigmaaldrich.com/US/en/product/sigma/i8896>, 10 pages, dated at least as early as Dec. 23, 2021, retrieved from Sigma-Aldrich website on Dec. 23, 2021.

* cited by examiner

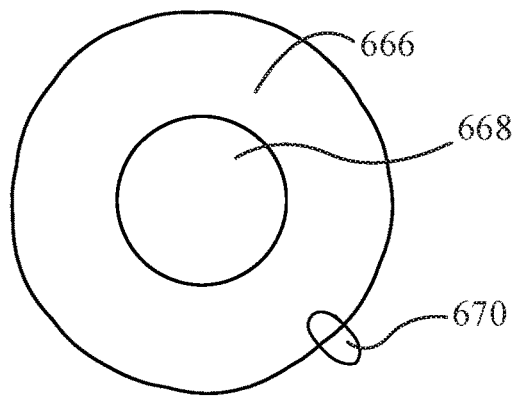
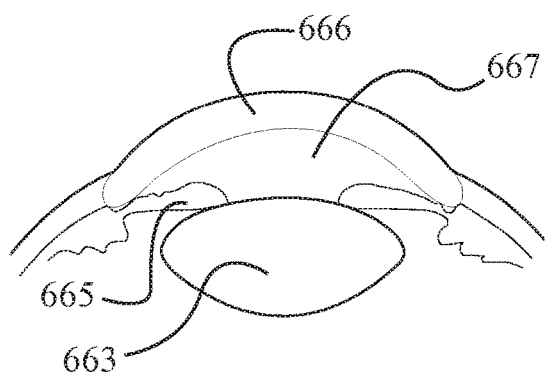
FIG. 41A
FIG. 41B
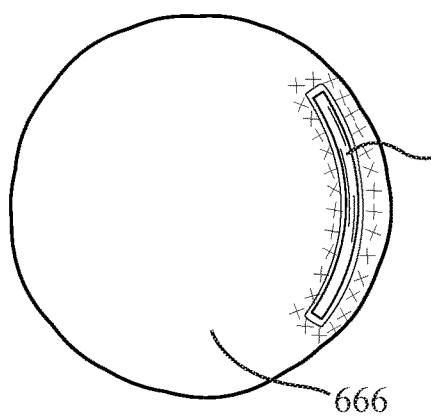
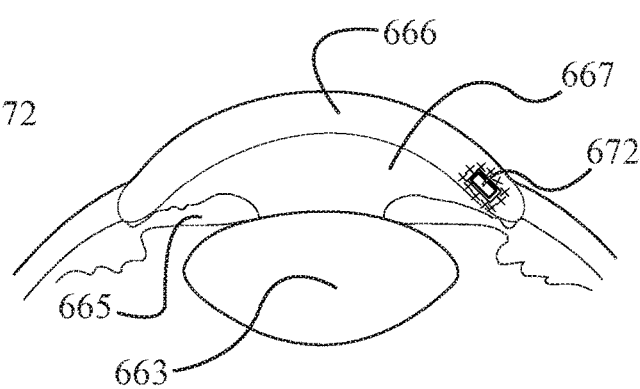
FIG. 42A
FIG. 42B
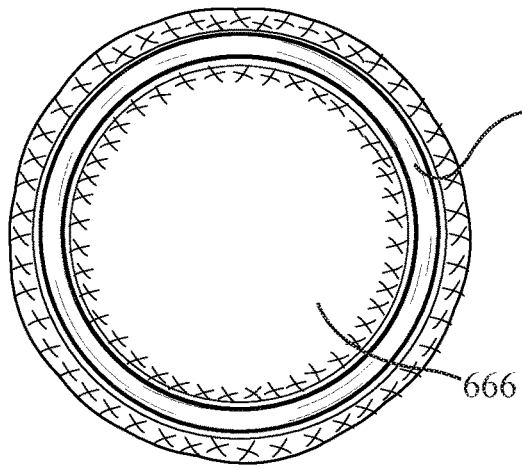
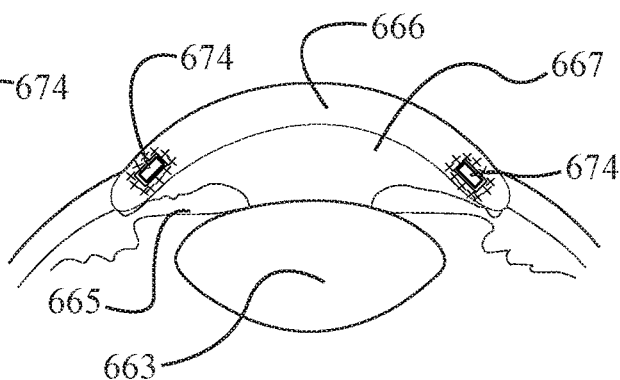
FIG. 43A
FIG. 43B

METHOD OF CORNEAL AND SCLERAL INLAY CROSSLINKING AND PRESERVATION

CROSS-REFERENCE TO RELATED APPLICATIONS

This patent application claims priority to U.S. Provisional Patent Application No. 62/780,404, entitled "Method Of Corneal And Scleral Inlay Crosslinking And Preservation", filed on Dec. 17, 2018, and is a continuation-in-part of application Ser. No. 16/451,247, entitled "Method Of Corneal Transplantation Or Corneal Inlay Implantation With Cross-Linking", filed on Jun. 25, 2019, now U.S. Pat. No. 10,881,503, which claims priority to U.S. Provisional Patent Application No. 62/849,941, entitled "Method Of Corneal Transplantation Or Corneal Inlay Implantation With Cross-Linking", filed on May 19, 2019, and Ser. No. 16/451,247 is a continuation-in-part of application Ser. No. 16/414,713, entitled "Method Of Corneal Transplantation Or Corneal Inlay Implantation With Cross-Linking", filed on May 16, 2019, now U.S. Pat. No. 10,583,221, which claims priority to U.S. Provisional Patent Application No. 62/672,161, entitled "Drug Delivery Implant And A Method Using The Same", filed on May 16, 2018, and Ser. No. 16/414,713 is a continuation-in-part of application Ser. No. 15/941,641, entitled "Method Of Corneal Transplantation Or Corneal Inlay Implantation With Cross-Linking", filed on Mar. 30, 2018, now U.S. Pat. No. 10,314,690, which claims priority to U.S. Provisional Patent Application No. 62/478,914, entitled "Method Of Corneal Transplantation With Cross-Linking", filed on Mar. 30, 2017, and Ser. No. 15/941,641 is a continuation-in-part of application Ser. No. 15/230,445, entitled "Corneal Lenslet Implantation With A Cross-Linked Cornea", filed on Aug. 7, 2016, now U.S. Pat. No. 9,937,033, which claims priority to U.S. Provisional Patent Application No. 62/360,281, entitled "Method of Altering the Refractive Properties of an Eye", filed on Jul. 8, 2016, and Ser. No. 15/230,445 is a continuation-in-part of application Ser. No. 14/709,801, entitled "Corneal Transplantation With A Cross-Linked Cornea", filed on May 12, 2015, now U.S. Pat. No. 9,427,355, which claims priority to U.S. Provisional Patent Application No. 61/991,785, entitled "Corneal Transplantation With A Cross-Linked Cornea", filed on May 12, 2014, and to U.S. Provisional Patent Application No. 62/065,714, entitled "Corneal Transplantation With A Cross-Linked Cornea", filed on Oct. 19, 2014, the disclosure of each of which is hereby incorporated by reference as if set forth in their entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a method of corneal transplantation or corneal inlay implantation with cross-linking. More particularly, the invention relates to method of corneal transplantation or corneal inlay implantation with cross-linking for preventing an immune response to a corneal graft and/or rejection of the corneal graft by the patient, and for preventing vascular and/or fibrous tissue growth on, and surrounding a keratoprosthesis lens or other type of corneal implant or inlay.

2. Background

Corneal scarring is a major cause of blindness, especially in developing countries. There are various causes for corneal scarring, which include: bacterial infections, viral infections, fungal infections, parasitic infections, genetic corneal problems, Fuch's dystrophy, other corneal dystrophies, corneal trauma, or failed surgery. A corneal transplant is often required if the corneal scarring is extensive, and cannot be corrected by other means. However, there can be major complications associated with a corneal transplant, such as corneal graft rejection wherein the transplanted cornea is rejected by the patient's immune system.

A normal emmetropic eye includes a cornea, a lens and a retina. The cornea and lens of a normal eye cooperatively focus light entering the eye from a far point, i.e., infinity, onto the retina. However, an eye can have a disorder known as ametropia, which is the inability of the lens and cornea to focus the far point correctly on the retina. Typical types of ametropia are myopia, hypermetropia or hyperopia, and astigmatism.

A myopic eye has either an axial length that is longer than that of a normal emmetropic eye, or a cornea or lens having a refractive power stronger than that of the cornea and lens of an emmetropic eye. This stronger refractive power causes the far point to be projected in front of the retina.

Conversely, a hypermetropic or hyperopic eye has an axial length shorter than that of a normal emmetropic eye, or a lens or cornea having a refractive power less than that of a lens and cornea of an emmetropic eye. This lesser refractive power causes the far point to be focused behind the retina.

An eye suffering from astigmatism has a defect in the lens or shape of the cornea converting an image of the point of light to a line. Therefore, an astigmatic eye is incapable of sharply focusing images on the retina.

While laser surgical techniques, such as laser-assisted in situ keratomileusis (LASIK) and photorefractive keratectomy (PRK) are known for correcting refractive errors of the eye, these laser surgical techniques have complications, such as post-operative pain and dry eye or scarring. Also, these laser surgical techniques cannot be safely used on patients with corneas having certain biomechanical properties. For example, corneal ectasia may occur if these laser surgical techniques are applied to patients having thin corneas (e.g., corneas with thicknesses that are less than 500 microns).

Therefore, what is needed is a method for corneal transplantation that reduces the likelihood that the implanted cornea will be rejected by the patient. Moreover, a method is needed for corneal transplantation that is capable of preserving the clarity of the transplanted cornea. Furthermore, there is a need for a method of corneal transplantation that reduces the likelihood that the transplanted cornea will be invaded by migrating cells. Also, what is needed is a method for corneal lenslet implantation for modifying the cornea to better correct ametropic conditions without removing the tissue that potentially creates a side effect of keratectasia. In addition, a method is needed for corneal lenslet implantation that prevents a lens implant from moving around inside the cornea once implanted so that the lens implant remains centered about the visual axis of the eye, and is not rejected by the host tissue.

Further, a number of the diseases can lead to corneal opacity and loss of sight. Among these are many infectious diseases, caused by bacterial, viral, and fungal or other organisms. Furthermore, penetrating and contusion corneal injury in children and adults can create a corneal scar, which prevents a patient from seeing. Postsurgical procedures, such as cataract surgery, and glaucoma, etc. can also damage corneal endothelial cells with loss of clarity of the corneal tissue. A large number of corneal diseases have a genetic predisposition, and can cloud the cornea over a period of time.

In order to clear the visual axis for light to reach the retina, it often requires performing a corneal transplantation. In this process, a cornea from a recently deceased person is excised and transplanted in place of the diseased cornea in the host.

Often, the first corneal transplantation is successful for about 90% of the cases. However, the rest of the cases require repeated corneal transplantation to replace a rejected one. These cases and all cases that have vascular components to the corneal cloudiness constitute the group of patients in whom the corneal transplant can be rejected in about 30% of the cases. As a general rule, the more corneal transplantations that are performed, the greater are the chances of a graft rejection.

Medical therapy, steroids, immunosuppressants, etc. are often applied to the cornea, but in repeated cases of corneal transplantation and complicated cases, they have limited success with their associated side effects. This process can ultimately lead to corneal edema, cellular immune response, complete corneal cloudiness and vascularization, in addition to dry eye. In these cases, one can remove the center part of the opaque cornea and create a circular pocket in the remaining peripheral cornea horizontally with a knife as known in the art. This produces an anterior and a posterior flap around the central opening and a remaining part of the cornea in which a prosthetic lens with a flange is implanted. However, often these artificial lenses can be rejected because of the body's immune response.

Therefore, it is apparent that a need also exists for a corneal transplantation method with cross-linking that prevents an immune response to a corneal transplant and/or rejection of the corneal transplant by the patient, and for a corneal transplantation method with cross-linking that prevents vascular and/or fibrous tissue growth on, and surrounding a corneal implant, inlay, or keratoprosthesis lens.

BRIEF SUMMARY OF EMBODIMENTS OF THE INVENTION

Accordingly, the present invention is directed to a method of corneal transplantation or corneal inlay implantation with cross-linking that substantially obviates one or more problems resulting from the limitations and deficiencies of the related art.

In accordance with one or more embodiments of the present invention, there is provided a method of corneal and scleral inlay crosslinking and preservation. The method comprising the steps of: (i) cross-linking at least a portion of a donor cornea or a donor sclera so as to kill cellular elements in the portion of the donor cornea or the donor sclera, and make the portion of the donor cornea or the donor sclera less antigenic to a body portion of a recipient patient in which the portion of the donor cornea or the donor sclera is to be implanted; and (ii) storing the cross-linked donor cornea or the donor sclera for a long period of time prior to implanting the portion of the donor cornea or the donor sclera into the body portion of the recipient patient.

In a further embodiment of the present invention, the step of cross-linking the portion of the donor cornea or the donor sclera comprises the substeps of: (a) applying a photosensitizer to the portion of the donor cornea or the donor sclera so as to penetrate the tissue of the donor cornea or the donor sclera; and (b) irradiating the portion of the donor cornea or the donor sclera with ultraviolet light so as to cross-link collagen in the portion of the donor cornea or the donor sclera so as to make the portion of the donor cornea or the donor sclera less antigenic to the body portion of the recipient patient in which the portion of the donor cornea or the donor sclera is to be implanted.

In yet a further embodiment, the photosensitizer comprises riboflavin and a cell penetrating agent, and the portion of the donor cornea or the donor sclera is irradiated by using a laser emitting the ultraviolet light.

In still a further embodiment, the cell penetrating agent comprises one or more nanoparticles conjugated with one or more cell penetrating peptides (CPP) and/or activatable-cell penetrating peptides (ACPP).

In yet a further embodiment, after the substep of irradiating the portion of the donor cornea or the donor sclera with ultraviolet light, the method further comprises the steps of: (iii) implanting the portion of the donor cornea into a host cornea of the recipient patient; and (iv) applying low intensity focused ultrasound to stromal cells of the host cornea of the recipient patient so as to kill the stromal cells of the host cornea.

In still a further embodiment, the step of storing the cross-linked donor cornea or the donor sclera for a long period of time comprises storing the cross-linked donor cornea or the donor sclera for a time period of one year or more.

In yet a further embodiment, prior to the step of cross-linking at least a portion of the donor cornea or the donor sclera, the method comprises the steps of: (iii) dissecting and removing all of the soft tissue from a donor eye so to leave only the donor cornea and/or the donor sclera, the removed soft tissue of the donor eye comprising the conjunctiva, muscles, retina, choroid, iris, ciliary body, and optic nerve; and (iv) cleansing the donor cornea and/or the donor sclera in a physiological solution so as to prepare the donor cornea and/or the donor sclera for cross-linking.

In still a further embodiment, the method further comprising the step of: (iii) cutting and shaping the donor cornea using a cutting instrument so as to form a lens having a desired thickness, shape, and diameter; the lens comprising a plus or minus lens, an astigmatic lens, or a combination thereof.

In yet a further embodiment, prior to the step of cross-linking at least a portion of the donor cornea or the donor sclera, the method comprises the step of: (iii) exposing the donor cornea or the donor sclera to a high intensity ultrasonic or hydrostatic force so as to destroy the cellular elements in the portion of the donor cornea or the donor sclera. Also, in this further embodiment, after the step of cross-linking at least a portion of the donor cornea or the donor sclera, the method comprises the step of: (iv) cleansing the donor cornea and/or the donor sclera in a saline solution to remove the reactive oxygen species and enzymes released from the destroyed cellular elements by mechanical agitation of the donor cornea or the donor sclera or by applying a low frequency ultrasound to the donor cornea or the donor sclera.

In still a further embodiment, after the step of cross-linking at least a portion of the donor cornea or the donor sclera, the method comprises the step of: (iii) implanting the portion of the donor cornea or the donor sclera in the body of the recipient patient to replace an injured chin, lip, nose, or cheek; or in cosmetic surgery, to augment a chin, lip, nose, or cheek.

In yet a further embodiment, the step of cross-linking the portion of the donor cornea or the donor sclera comprises the substeps of: (a) applying a photosensitizer comprising riboflavin to the donor cornea or the donor sclera so as to penetrate the tissue of the donor cornea or the donor sclera; and (b) irradiating the donor cornea or the donor sclera with ultraviolet light so as to sterilize the donor cornea or the donor sclera.

In still a further embodiment, the recipient patient has an infected corneal ulcer or scleral weakness or infection, and the method further comprises the steps of: (iii) applying a photosensitizer conjugated with one or more antibody-coated metallic nanoparticles, one or more cell penetrating peptides (CPP), and one or more medications to a host eye of the recipient patient, the one or more medications selected from the group consisting of antibiotics, antifungals, antiparasites, antivirals, and combinations thereof; and (iv) irradiating the area of the host eye having the infected corneal ulcer or the scleral weakness or infection with ultraviolet light so as to kill bacteria, fungi, parasites, and/or viruses while cross-linking the area of the host eye to resist enzymatic degradation and heal the infected corneal ulcer or the scleral weakness or infection.

In yet a further embodiment, the method further comprises the steps of: (iii) forming cavities or holes in the portion of the cross-linked donor cornea or the donor sclera using a laser so that the portion of the donor cornea or the donor sclera is capable of being used for sustained drug delivery; and (iv) co-culturing the donor cornea or the donor sclera in a medium having nanoparticles conjugated with one or more medications and cell penetrating peptides (CPP) or lipids that penetrate the tissue scaffolds formed by the cavities or holes in the portion of the donor cornea or the donor sclera, the portion of the donor cornea or the donor sclera configured to be used for sustained drug delivery when the portion of the donor cornea or the donor sclera is implanted in the body portion of the recipient patient.

In still a further embodiment, the nanoparticles are formed from polylactic, polyglycolic, polycaprolactone, and/or silicon; and wherein the one or more medications are selected from the group consisting of anti-inflammatory agents, steroids, nonsteroidal anti-inflammatory drugs (NSAIDs), anti-proliferative agents, immunosuppressives, antibiotics, anti-glaucoma agents, Rock inhibitors, anti-integrins, Wnt inhibitors, GSK inhibitors, anti-vascular endothelial growth factors (anti-VEGFs), and combinations thereof.

In yet a further embodiment, the step of cross-linking the portion of the donor cornea or the donor sclera comprises the substeps of: (a) applying riboflavin to the portion of the donor cornea or the donor sclera so as to penetrate the tissue of the donor cornea or the donor sclera; and (b) irradiating the portion of the donor cornea or the donor sclera using a laser emitting ultraviolet light so as to cross-link collagen in the portion of the donor cornea or the donor sclera so as to make the portion of the donor cornea or the donor sclera less antigenic to the body portion of the recipient patient in which the portion of the donor cornea or the donor sclera is to be implanted.

In still a further embodiment, prior to the step of cross-linking the portion of the donor cornea or the donor sclera with the riboflavin and the ultraviolet light, the method comprises the step of: (iii) using chemical means or mechanical means to destroy the cellular elements in the portion of the donor cornea or the donor sclera.

In yet a further embodiment, the chemical means for destroying the cellular elements in the portion of the donor cornea or the donor sclera are selected from the group consisting of ethanol, glycerol, acids, alkalis, peracetic acid, ammonium hydroxide ionic detergents, sodium dodecyl sulfate, sodium deoxycholate non-ionic detergents, zwitterionic detergents, Triton X-100, benzalkonium chloride, Igepal, genipin, and combinations thereof.

In still a further embodiment, the mechanical means for destroying the cellular elements in the portion of the donor cornea or the donor sclera comprises applying low intensity focused ultrasound to the portion of the donor cornea or the donor sclera.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 41A is a front view of a cornea of an eye illustrating a pupil, cornea, sclera, and limbus of the eye;

FIG. 41B is a partial side cross-sectional view of the eye of FIG. 41A illustrating an anterior chamber, iris, and lens of the eye;

FIG. 42A is a front view of a cornea of an eye illustrating a one-part semi-circular drug delivery implant disposed in a cross-linked pocket in the peripheral portion of the cornea;

FIG. 42B is a partial side cross-sectional view of the eye of FIG. 42A illustrating the one-part semi-circular drug delivery implant disposed in the cross-linked pocket in the peripheral portion of the cornea;

FIG. 43A is a front view of a cornea of an eye illustrating a doughnut-shaped drug delivery implant disposed in a cross-linked pocket in the peripheral portion of the cornea;

FIG. 43B is a partial side cross-sectional view of the eye of FIG. 43A illustrating the doughnut-shaped drug delivery implant disposed in the cross-linked pocket in the peripheral portion of the cornea;

Throughout the figures, the same elements are always denoted using the same reference characters so that, as a general rule, they will only be described once.

DETAILED DESCRIPTION OF EMBODIMENTS OF THE INVENTION

A first illustrative embodiment of a corneal transplant procedure with a cross-linked cornea is shown in FIGS. 1A-1D. The corneal transplant procedure illustrated in FIGS. 1A-1D involves full corneal replacement of the scarred or diseased cornea by the donor cornea. In other words, FIGS. 1A-1D illustrate a penetrating keratoplasty procedure wherein the full thickness of the scarred or diseased cornea is replaced with a cross-linked donor cornea (i.e., a full-thickness corneal transplant).

Figure 1A:
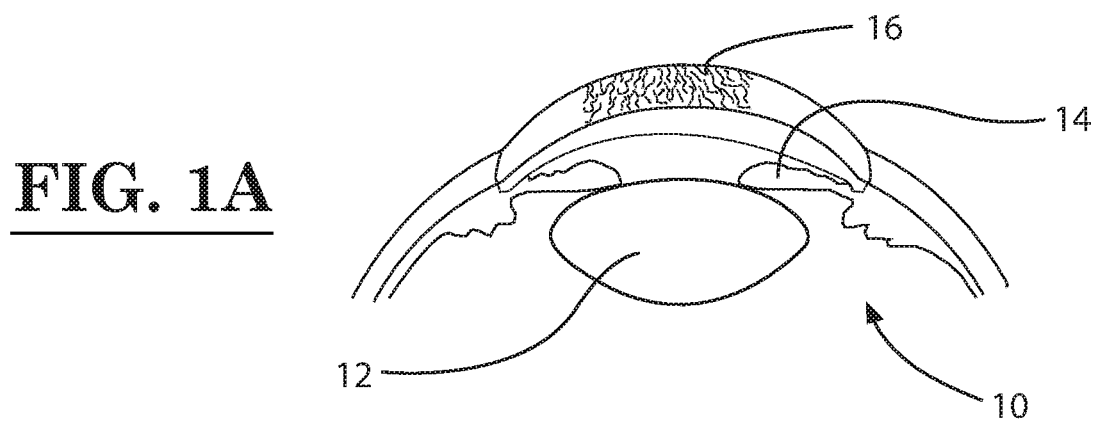
FIG. 1A is a partial side cross-sectional view of an eye having a scarred cornea, wherein substantially the entire thickness of the cornea is scarred.

Referring initially to FIG. 1A, it can be seen that substantially the entire thickness of the cornea 16 of the eye 10 is scarred and/or diseased (i.e., scarred, diseased, or scarred and diseased). FIG. 1A also illustrates the lens 12 and iris 14 of the eye 10, which are located posteriorly of the cornea 16. In this embodiment, it is necessary to replace substantially the entire thickness of the cornea 16 with a donor cornea.

Figure 1B:
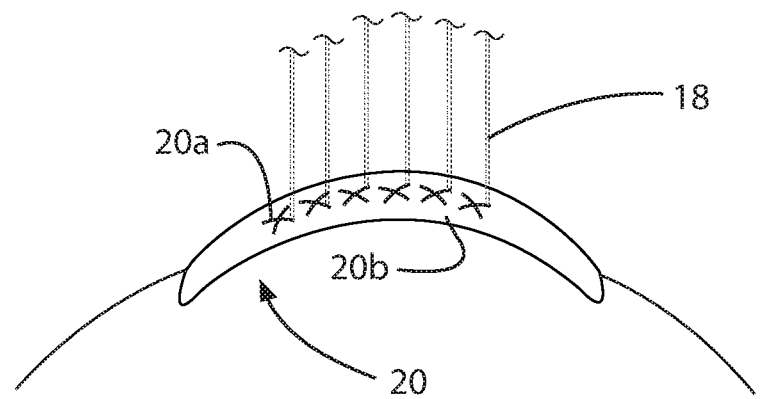
FIG. 1B is a partial side cross-sectional view of a donor cornea undergoing cross-linking.

In FIG. 1B, the cross-linking 18 of the clear donor cornea 20 is diagrammatically illustrated. As depicted in FIG. 1B, only the front portion 20a of the donor cornea 20 is cross-linked. That is, the cross-linking does not extend all the way to the rear portion 20b of the donor cornea 20. It is to be understood that the cross-linking 18 of the donor cornea 20 may also be done after implanting the donor cornea into the eye of the patient, rather than before implantation as shown in the illustrative example of FIGS. 1A-1D. Also, it is to be understood that all or just a part of the donor cornea 20 may be cross-linked.

In the illustrative embodiments described herein (i.e., as depicted in FIGS. 1A-1D, 2A-2C, and 3A-3C), the crosslinking of the clear donor cornea may comprise the steps of: (i) applying a photosensitizer to the donor cornea, the photosensitizer facilitating cross-linking of the donor cornea; and (ii) irradiating the donor cornea with ultraviolet light so as to activate cross-linkers in the donor cornea and thereby strengthen the donor cornea. The photosensitizer may comprise riboflavin or a solution comprising a liquid suspension having nanoparticles of riboflavin. The cross-linker may have between about 0.1% Riboflavin to about 100% Riboflavin or any other suitable range or specific percentage therein. The ultraviolet radiation or rays used to irradiate the donor cornea may be between about 370 nanometers and about 380 nanometers (or between 370 nanometers and 380 nanometers). The radiation is preferably about 3 mW or more as needed and emanates from a laser source at about a 3 cm distance from the donor cornea for about 30 minutes or less. The time of the exposure can vary depending on the light intensity, focus, and the concentration of riboflavin. However, the ultraviolet radiation can be applied at any suitable distance, time or wavelength. Preferably, cross-linking the donor cornea does not significantly change the refractive power of the donor cornea; however, if desired, cross-linking can change the refractive power of the donor cornea to any suitable degree.

In addition to Riboflavin, other suitable cross linking agents are low carbon carbohydrates, such as pentose sugar (e.g., ribose) or hexose sugar (e.g., glucose), or complex carbohydrates. Other crosslinking agents may include Transaminidases, transglutaminases or a naturally-derived cross-linker named malic acid derivative (MAD) concentrations higher than 30 mM, commercially available cross-linkers such as 1-ethyl-3-(3('-dimethylaminopropyl) carbodiimide (EDC), or ethyl-3(3-dimethylamino) propyl carbodiimide (EDC), etc. The cross-linking may also be done postoperatively by the application of other crosslinking agents, such as Triglycidylamine (TGA) synthesized via reacting epichlorhydrin and a carbodiimide, or the oxidized glycogen hexoses. The ribose, glucose and similar agents may penetrate the cornea easily using drops, gel, or the slow release mechanisms, nanoparticle, microspares, liposome sets. In addition, the crosslinkers may be delivered with Mucoadhesives.

In one or more embodiments, all or part of the donor cornea is cross-linked. Also, in one or more embodiments, a very high concentration of Riboflavin may be used because the in vitro cross-linking process may be stopped whenever needed prior to the transplantation of the donor cornea in the host eye. In addition, the power of the ultraviolet (UV) laser may also be increased so as to cross-link the tissue of the donor cornea faster. The use of a high concentration of Riboflavin, and the increasing of the ultraviolet (UV) laser power, are not possible during an in vivo cross-linking procedure because the aim of such an in vivo procedure is to protect the cells of the host cornea. Also, the in vivo process cannot be controlled as efficiently as in the vitro crosslinking of the corneal transplant.

In one or more embodiments, the donor cornea may be extracted from a human cadaver, or the cornea may be reconstructed as known in tissue engineering in vitro and three-dimensionally (3D) printed. Cross-linking of a culture-grown cornea eliminates the cellular structure inside the cornea. If needed again, the healthy corneal endothelium of the patient may be grown in vitro for these tissues by placing them on the concave surface of the cornea and encouraging their growth under laboratory control conditions prior to the transplantation.

In the embodiments where the donor cornea is tissue culture grown, the cornea may be formed from mesenchymal fibroblast stem cells, embryonic stem cells, or cells derived from epithelial stem cells extracted from the same patient, or a mixture of these cells. Using known tissue culture techniques, the cells may produce a transparent corneal stroma. This culture-grown corneal stroma will not have a corneal epithelium or a corneal endothelium. Thus, it eliminates the complexity of developing a full thickness cornea in the tissue culture. This stromal transplant may be used as a lamellar or partial thickness replacement of the existing host cornea. This transplant may also be used to augment or add to the thickness of the host cornea. This transparent corneal stroma may be transplanted either prior to, or after being cross-linked using various cross-linking methods.

In one or more embodiments, the cross-linked donor cornea may be sized and precisely cut with a femtosecond laser to the desired shape and curvature to replace the removed host cornea so that the refractive errors of the recipient are also automatically corrected with the cross-linked cornea.

Figure 1C:
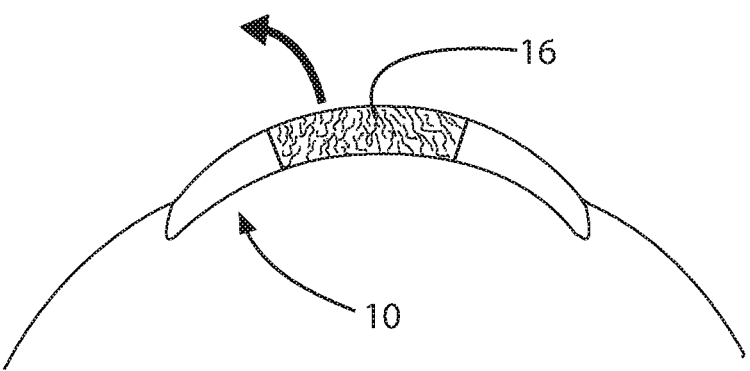
FIG. 1C is a partial side cross-sectional view of the eye of FIG. 1A, wherein the scarred cornea is shown being removed.

Now, referring to FIG. 1C, it can be seen that the scarred and/or diseased cornea 16 is shown being removed from the eye 10. The scarred and/or diseased cornea 16 may be removed from the eye 10 by using various suitable means, such as mechanical means or cutting using a laser. When mechanical means are used to remove the scarred and/or diseased cornea 16 from the eye 10, the scarred and/or diseased cornea 16 may initially be cut away or dissected from the remainder of the eye 10 using a sharp mechanical instrument (e.g., a surgical micro-knife, a needle, a sharp spatula, a pair of micro-scissors), and then subsequently removed or extracted with a pair of micro-forceps. When laser cutting is used to remove the scarred and/or diseased cornea 16 from the eye 10, the scarred and/or diseased cornea 16 may be cut away using a suitable laser, such as a femtosecond laser. Also, in some embodiments, the mechanical means for cutting and extraction (e.g., the surgical micro-knife and/or pair of micro-scissors) may be used in combination with the laser means (e.g., the femtosecond laser).

In one or more embodiments, the donor cornea may be shaped and cut with the femtosecond laser prior to the cross-linking thereof so as to replace part or all of the recipient cornea which is cut with the femtosecond laser. In these one or more embodiments, the entire donor and host cornea together may be cross-linked with Riboflavin and UV radiation. These procedures may also be performed on a culture-grown transplant cornea.

Figure 1D:
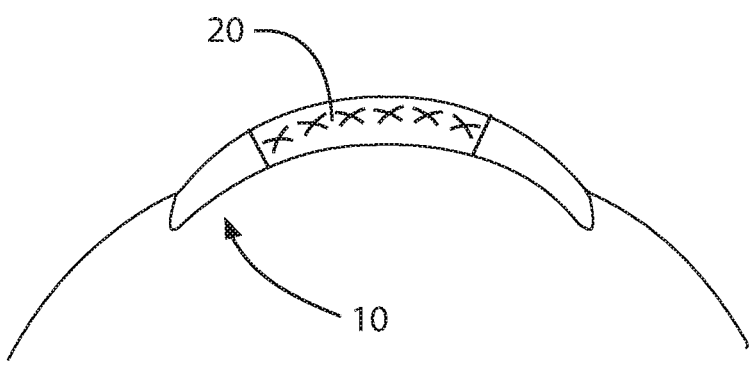
FIG. 1D is a partial side cross-sectional view of the eye of FIG. 1A, wherein the cross-linked donor cornea is shown being implanted in the location previously occupied by the scarred cornea.

Then, as shown in FIG. 1D, after the scarred and/or diseased cornea 16 has been removed from the eye 10, the cross-linked donor cornea 20 is implanted into the eye 10 of the patient in the location previously occupied by the scarred and/or diseased cornea 16. After implantation of the cross-linked donor cornea 20, sutures or a suitable adhesive may be utilized to secure the cross-linked donor cornea 20 in place on the eye 10. When sutures are used for holding the donor cornea 20 in place, the sutures may comprise nylon sutures, steel sutures, or another suitable type of non-absorbable suture. When the cornea 16 is subsequently ablated after the implantation of the donor cornea, as will be described hereinafter, additional sutures may be required after ablation.

In one or more embodiments, a biodegradable adhesive is used in a corneal transplantation procedure with the cross-linked donor cornea 20 described above, or with a noncross-linked corneal transplant. In these one or more embodiments, the biodegradable adhesive obviates the need for a suture in the corneal transplant procedure. Sutures generally distort the surface of the cornea and can produce an optically unacceptable corneal surface. Also, the use of the biodegradable adhesive obviates the need for glues requiring exothermic energy. Glues that use an exothermic effect, such as Fibronectin, need thermal energy to activate their adhesive properties. This thermal energy, such as that delivered by a high-powered laser, produces sufficient heat to coagulate the Fibronectin and the tissue that it contacts. Any thermal effect on the cornea produces: (i) corneal opacity, (ii) tissue contraction, and (iii) distortion of the optical surface of the cornea. The tissue adhesion created by these glues, including Fibronectin or fibrinogen, is flimsy and cannot withstand the intraocular pressure of the eye.

In fact, sutures are superior to these types of adhesives because the wound becomes immediately strong with sutures, thereby supporting the normal intraocular pressure of between 18 and 35 mmHg. In contrast to the use of a suture in which distortion that is caused by suture placement can be managed by cutting and removing the suture, the distortion caused by the coagulated corneal tissue cannot be corrected.

Other glues, such as cyanoacrylate, become immediately solid after coming into contact with the tissue or water. These glues produce a rock-hard polymer, the shape of which cannot be controlled after administration. Also, the surface of the polymer created by these glues is not smooth. Thus, the eyelid will rub on this uneven surface, and the uneven surface scratches the undersurface of the eyelid when the eyelid moves over it. In addition, the cyanoacrylate is not biodegradable or biocompatible. As such, it causes an inflammatory response if applied to the tissue, thereby causing undesirable cell migration and vascularization of the cornea.

Thus, by using a biocompatible and absorbable acrylate or other biodegradable glues that do not need exothermic energy for the process of adhesion (i.e., like fibronectin or fibrinogen), one is able to maintain the integrity of the smooth corneal surface. In one or more embodiments, the biocompatible and biodegradable adhesive may be painted only at the edges of the transplant prior to placing it in the host or diseased cornea. In these embodiments, the biocompatible and biodegradable adhesive only comes into contact with the host tissue at the desired predetermined surface to create a strong adhesion. The adhesion may last a few hours to several months depending on the composition of the molecule chosen and the concentration of the active component.

Other suitable biodegradable adhesives or glues that may be used in conjunction with the transplant include combinations of gallic acid, gallic tannic acid, Chitosan, gelatin, polyphenyl compound, Tannic Acid (N-isopropylacrylamide (PNIPAM), and/or Poly(N-vinylpyrrolidone) with polyethylene glycol (PEG). That is, polyethylene glycol (PEG) may be mixed with any one or plurality of gallic acid, gallic tannic acid, Chitosan, gelatin, polyphenyl compound, Tannic Acid (N-isopropylacrylamide (PNIPAM), and Poly(N-vinylpyrrolidone), so as to form a molecular glue. These adhesives are suitable for the use on the cornea because they create a tight wound that prevents leakage from the corneal wound and maintain the normal intraocular pressure shortly after their application and also do not distort the wound by causing traction on the tissue.

In one or more embodiments, the donor cornea may be temporarily sutured to the host cornea by only a few single sutures to the host cornea. Then, the sutures may be removed immediately after donor cornea is fixed to the host cornea with a suitable adhesive.

Figure 2A:
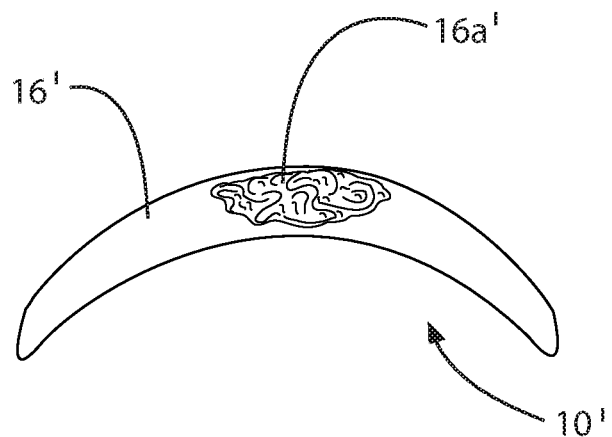
FIG. 2A is a partial side cross-sectional view of an eye having internal corneal scar tissue.
Figure 2B:
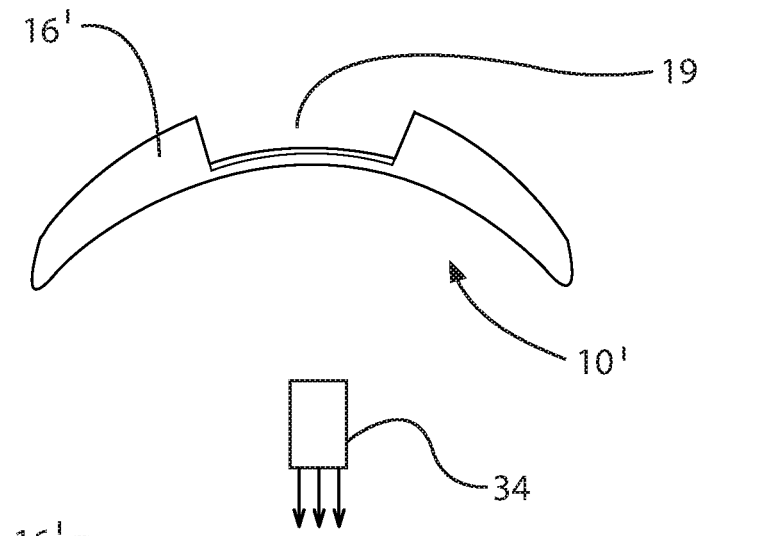
FIG. 2B is a partial side cross-sectional view of the eye of FIG. 2A, wherein the scarred corneal tissue has been externally removed from the eye.
Figure 2C:
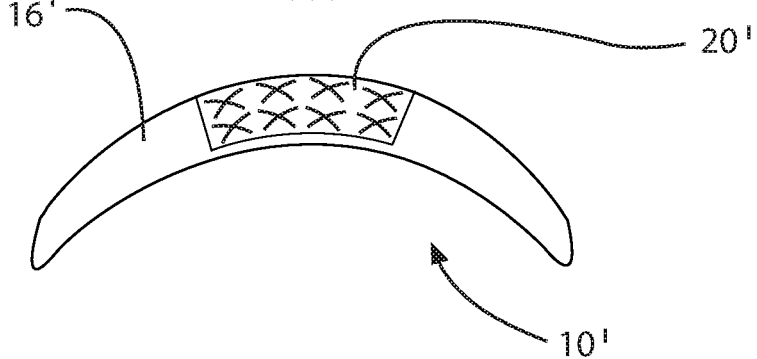
FIG. 2C is a partial side cross-sectional view of the eye of FIG. 2A, wherein a cross-linked donor cornea is shown being implanted in the location previously occupied by the scarred corneal tissue.

A second illustrative embodiment of a corneal transplant procedure with a cross-linked cornea is shown in FIGS. 2A-2C. Unlike the first embodiment described above, the corneal transplant procedure illustrated in FIGS. 2A-2C does not involve full corneal replacement of the scarred or diseased cornea by the donor cornea. Rather, FIGS. 2A-2C illustrate a lamellar keratoplasty procedure wherein only a portion of the cornea 16' of the eye 10' contains scarred and/or diseased tissue (i.e., a full-thickness corneal section is not removed). In the procedure of FIGS. 2A-2C, an internal scarred and/or diseased portion 16a' of the cornea 16' is externally removed from the eye 10' of a patient.

Referring initially to FIG. 2A, it can be seen that only an internal portion 16a' of the cornea 16' is scarred and/or diseased. As such, in this embodiment, it is not necessary to replace the entire thickness of the cornea 16 with a donor cornea as was described above in conjunction with FIGS. 1A-1D, but rather just a portion of the cornea 16'.

Next, referring to FIG. 2B, it can be seen that the scarred and/or diseased portion 16a' has been externally removed from the cornea 16' of the eye 10' such that the cornea 16' comprises a cavity 19 disposed therein for receiving the donor cornea. Because an external approach was utilized for removing the scarred and/or diseased portion 16a' of the cornea 16', the cavity 19 comprises a notch-like void in the outside or anterior surface of the cornea 16'. As described above for the first embodiment, the scarred and/or diseased corneal portion 16a' may be removed from the remainder of the cornea 16' using various suitable means, such as mechanical means or the laser cutting means (e.g., femtosecond laser) described above.

Finally, as shown in FIG. 2C, after the scarred and/or diseased portion 16a' has been removed from the remainder of the cornea 16' of the eye 10', the cross-linked donor cornea or cross-linked donor corneal portion 20' is implanted into the eye 10' of the patient in the location previously occupied by the scarred and/or diseased corneal portion 16a'. As described above, after implantation of the cross-linked donor corneal portion 20' into the eye 10', sutures or a suitable adhesive (e.g., the biocompatible and biodegradable adhesive described above) may be utilized to secure the cross-linked donor corneal portion 20' in place on the host cornea of the eye 10'.

After the cross-linked donor corneal portion 20' is implanted into the eye 10' of the patient, a portion of the cornea 16' may be ablated so as to change the refractive properties of the eye (e.g., to give the patient perfect or near perfect refraction). The ablation of the portion of the cornea 16' may be performed using a suitable laser 34, such as an excimer laser. The ablation by the laser causes the ablated tissue to essentially evaporate into the air. Also, the ablation of the portion of the cornea 16' may be done intrastromally, as with LASIK (laser-assisted in situ keratomileusis), or on the surface of the cornea, as with PRK (photorefractive keratectomy). The ablation may be performed a predetermined time period after the corneal transplantation so as to enable the wound healing process of the recipient's cornea to be completed. It is to be understood that the ablation, which follows the corneal transplantation, may be performed in conjunction with any of the embodiments described herein.

It is also to be understood that, in some alternative embodiments, the ablation may be performed prior to the transplantation of the donor cornea, rather than after the transplantation of the donor cornea. For example, in one or more alternative embodiments, a lenticle may be precisely cut in the tissue of a culture-grown stroma of a donor cornea by using a femtosecond laser so that when implanted into the host cornea, it corrects the residual host eye's refractive error.

Figure 3A:
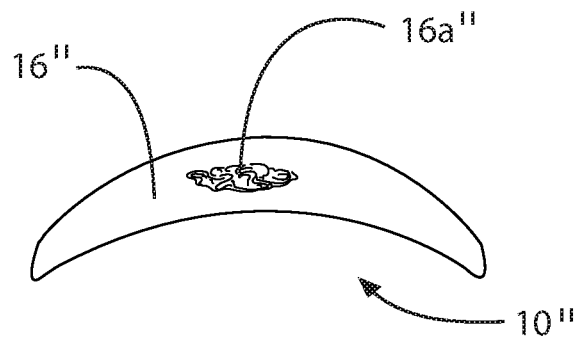
FIG. 3A is a partial side cross-sectional view of an eye having internal corneal scar tissue.
Figure 3B:
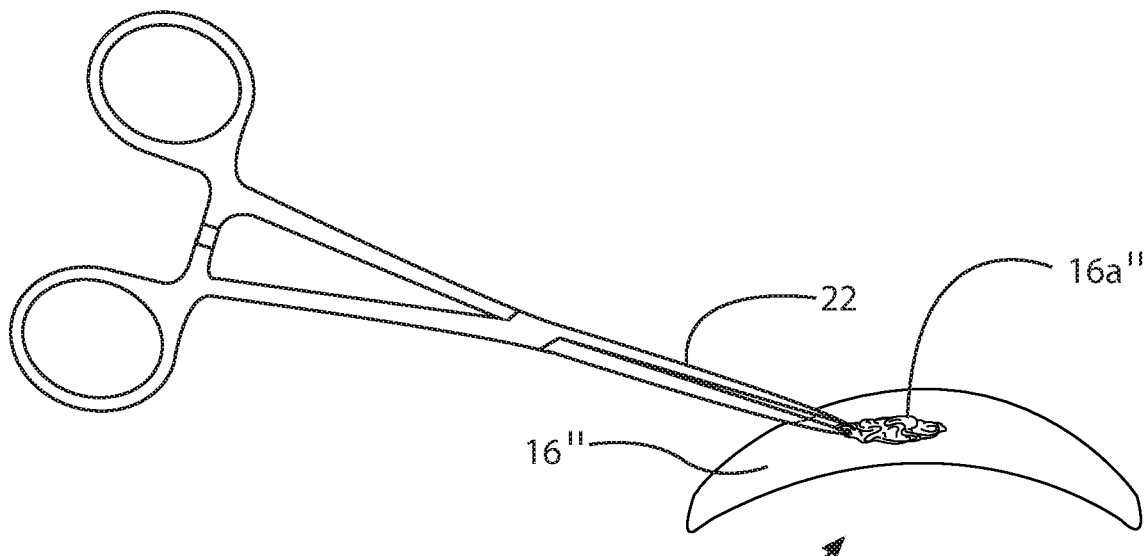
FIG. 3B is a partial side cross-sectional view of the eye of FIG. 3A, wherein the scarred corneal tissue is shown being internally removed from the eye.
Figure 3C:
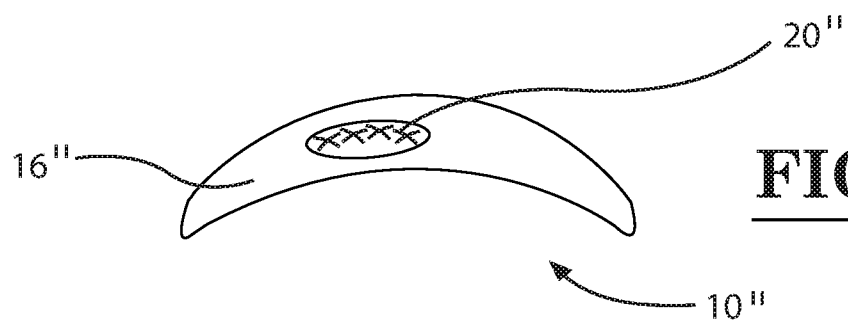
FIG. 3C is a partial side cross-sectional view of the eye of FIG. 3A, wherein a cross-linked donor cornea is shown being implanted in the location previously occupied by the scarred corneal tissue.

A third illustrative embodiment of a corneal transplant procedure with a cross-linked cornea is shown in FIGS. 3A-3C. Like the second embodiment described above, the corneal transplant procedure illustrated in FIGS. 3A-3C only involves replacing a scarred and/or diseased portion 16a" of the cornea 16" with a donor corneal portion. Thus, similar to the second embodiment explained above, FIGS. 3A-3C illustrate a lamellar keratoplasty procedure wherein only a portion of the cornea 16" of the eye 10" contains scarred and/or diseased tissue (i.e., a full-thickness corneal section is not removed). Although, in the procedure of FIGS. 3A-3C, an internal scarred and/or diseased portion 16a" of the cornea 16" is internally removed from the eye 10" of a patient, rather than being externally removed as in the second embodiment of FIGS. 2A-2C.

Referring initially to FIG. 3A, it can be seen that only an internal portion 16a" of the cornea 16" of the eye 10" is scarred and/or diseased. As such, in this embodiment, like the preceding second embodiment, it is not necessary to replace the entire thickness of the cornea 16" with a donor cornea, but rather just a portion of the cornea 16".

Next, referring to FIG. 3B, it can be seen that the scarred and/or diseased portion 16a" is being internally removed from the remainder of the cornea 16" using a pair of forceps 22 (i.e., mechanical means of removal are illustrated in FIG. 3B). Advantageously, because an internal approach is being utilized for removing the scarred and/or diseased portion 16a" of the cornea 16", the cornea 16" will not comprise the notch-like cavity 19 disposed in the outside or anterior surface of the cornea, which was described in conjunction with the preceding second embodiment. As described above for the first and second embodiments, the scarred and/or diseased corneal portion 16a" may be removed from the remainder of the cornea 16" using other suitable alternative means, such as laser cutting techniques (e.g., using a femtosecond laser). Advantageously, the femtosecond laser is capable of cutting inside the tissue without involving the surface of the tissue. The cut part of the tissue can then be removed by other means (e.g., micro-forceps).

Finally, as shown in FIG. 3C, after the scarred and/or diseased corneal portion 16a" has been removed from the remainder of the cornea 16" of the eye 10", the cross-linked donor cornea or cross-linked donor corneal portion 20" is implanted into the eye 10" of the patient in the location previously occupied by the scarred and/or diseased corneal portion 16a". After implantation of the cross-linked donor corneal portion 20", sutures or a suitable adhesive (e.g., the biocompatible and biodegradable adhesive described above) may be utilized to secure the cross-linked donor corneal portion 20" in place on the host cornea of the eye 10". Advantageously, the cross-linked donor corneal portion 20", which is strengthened by the cross-linking performed thereon, reinforces the cornea 16" and greatly reduces the likelihood of corneal graft rejection.

It is to be understood that the scarred and/or diseased corneal portion 16a" that is removed from the cornea 16" may also be replaced with stroma stem cells or mesenchymal stem cells, which can be contained in a medium, and then injected in the internal cavity previously occupied by the scarred and/or diseased corneal tissue 16a".

In one or more embodiments, mesenchymal stem cells also may be injected inside the donor cornea before or after transplantation. In addition, in one or more embodiments, daily drops of a Rho Kinase inhibitor may be added to the host eye after the surgery. The use of a medication, such as a Rho Kinase inhibitor, with the stem cells will encourage stem cell proliferation.

A fourth illustrative embodiment of a corneal transplant procedure with a cross-linked cornea is shown in FIGS. 4A-4E. Like the second and third embodiments described above, the corneal transplant procedure illustrated in FIGS. 4A-4E only involves replacing a scarred and/or diseased portion 16a''' of the cornea 16''' with a donor corneal portion. Thus, similar to the second and third embodiments explained above, FIGS. 4A-4E illustrate a lamellar keratoplasty procedure wherein only a portion of the cornea 16''' of the eye 10''' contains scarred and/or diseased tissue (i.e., a full-thickness corneal section is not removed). Although, in the procedure of FIGS. 4A-4E, a different-shaped scarred and/or diseased portion 16a''' of the cornea 16''' is removed.

Figure 4A:
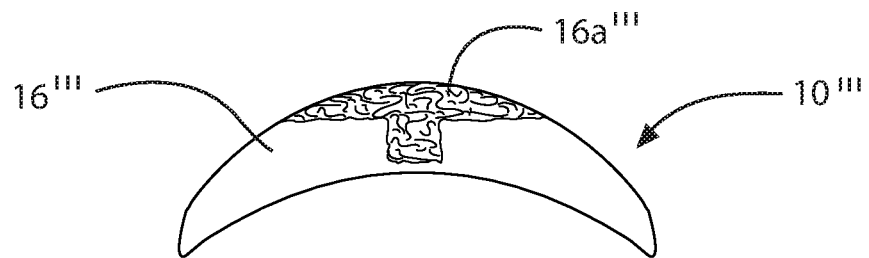
FIG. 4A is a partial side cross-sectional view of an eye having a T-shaped corneal scar and/or diseased tissue portion.

Referring initially to FIG. 4A, it can be seen that only a portion 16a''' of the cornea 16''' having a T-shape or "top hut" shape is scarred and/or diseased. As such, in this embodiment, it is not necessary to replace the entire thickness of the cornea 16''' with a donor cornea as was described above in conjunction with FIGS. 1A-1D, but rather just a portion 16a''' of the cornea 16'''. In this illustrative embodiment, the back side of the cornea 16''' is maintained (see e.g., FIG. 4D).

Figure 4B:
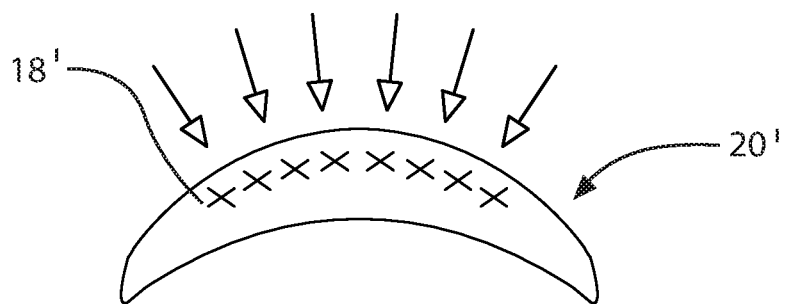
FIG. 4B is another partial side cross-sectional view of a donor cornea undergoing cross-linking.
Figure 4C:
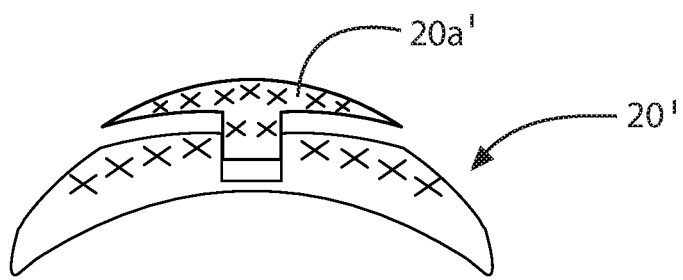
FIG. 4C is a partial side cross-sectional view illustrating a T-shaped portion of the cross-linked donor cornea being cut out from a remainder of the donor cornea.
Figure 5A:
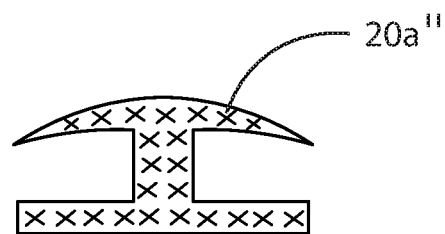
FIG. 5A illustrates an alternative configuration for the cross-linked donor cornea implant, wherein the donor cornea implant has a dumbbell shape.
Figure 5B:
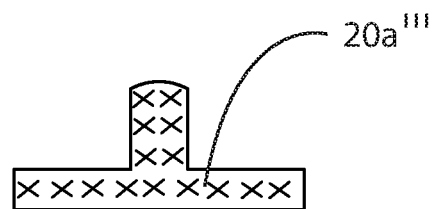
FIG. 5B illustrates another alternative configuration for the cross-linked donor cornea implant, wherein the donor cornea implant has a reversed or upside down T-shape.

In FIG. 4B, the cross-linking 18' of the clear donor cornea 20' is diagrammatically illustrated. As mentioned above, it is to be understood that all or just a part of the donor cornea 20' may be cross-linked. Then, in FIG. 4C, it can be seen that a portion 20a' of the clear donor cornea 20', which has a T-shape or "top hut" shape that matches the shape of the scarred and/or diseased portion 16a''' of the cornea 16''', is cut out from the remainder of the clear donor cornea 20' such that it has the necessary shape. In one or more embodiments, the portion 20a' may be cut from the clear donor cornea 20' and appropriately shaped using a femtosecond laser. As shown in FIGS. 5A and 5B, other suitably shaped cross-linked corneal portions may be cut from the clear donor cornea 20', such as a dumbbell-shaped corneal portion 20a" (see FIG. 5A) or a corneal portion 20a''' having a reversed T-shape or "reversed top hut" shape (see FIG. 5B), in order to accommodate correspondingly shaped scarred and/or diseased areas in the host cornea.

Figure 4D:
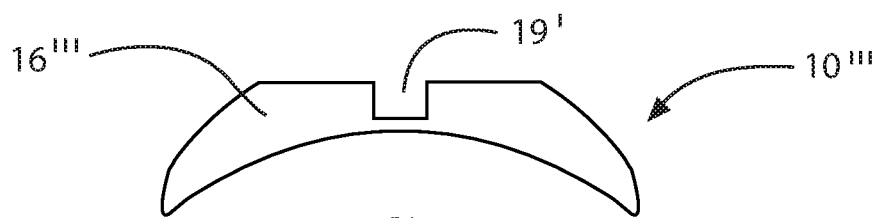
FIG. 4D is a partial side cross-sectional view of the eye of FIG. 4A, wherein the T-shaped scarred and/or diseased portion of corneal tissue has been removed from the eye.

Next, referring to FIG. 4D, it can be seen that the scarred and/or diseased portion 16a''' having the T-shape or "top hut" shape has been removed from the cornea 16''' of the eye 10''' such that the cornea 16''' comprises a cavity 19' disposed therein for receiving the donor cornea. As described above for the first three embodiments, the scarred and/or diseased corneal portion 16a''' may be removed from the remainder of the cornea 16''' using various suitable means, such as mechanical means or the laser cutting means (e.g., femtosecond laser) described above.

Figure 4E:
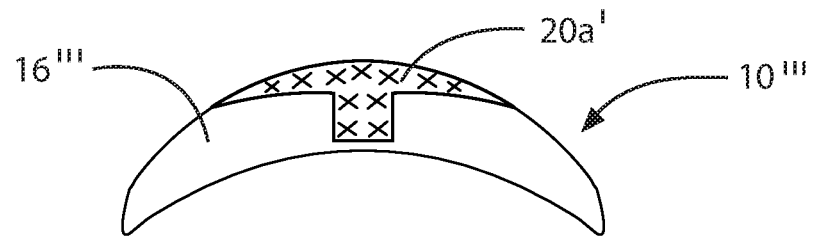
FIG. 4E is a partial side cross-sectional view of the eye of FIG. 4A, wherein the cross-linked T-shaped donor cornea portion is shown being implanted in the location previously occupied by the scarred and/or diseased corneal tissue portion.

Finally, as shown in FIG. 4E, after the scarred and/or diseased portion 16a''' has been removed from the remainder of the cornea 16''' of the eye 10''', the cross-linked donor corneal portion 20a' is implanted into the eye 10''' of the patient in the location previously occupied by the scarred and/or diseased corneal portion 16a'''. Because the shape of the transplant corresponds to that of the removed portion 16a''' of the cornea 16''', the transplant sits comfortably in its position in the host cornea. As described above, after implantation of the cross-linked donor corneal portion 20a' into the eye 10''', sutures or a suitable adhesive (e.g., the biocompatible and biodegradable adhesive described above) may be utilized to secure the cross-linked donor corneal portion 20a' in place on the host cornea 16''' of the eye 10'''. For example, if a biocompatible and biodegradable adhesive is used to secure the cross-linked donor corneal portion 20a' in place in the cornea 16''' of the eye 10''', the edges of the donor corneal portion 20a' are coated with the biocompatible and biodegradable adhesive so as to give the transplant a reliable stability. In this case, it is desirable to have the attachment of the transplant maintained by the biocompatible and biodegradable adhesive for a period of months (i.e., it is desirable for the transplant to be secured in place by the biocompatible and biodegradable adhesive for as long as possible).

An illustrative embodiment of a corneal lenslet implantation procedure with a cross-linked cornea is shown in FIGS. 6A-6C and 7A-7C. Similar to the second, third, and fourth embodiments described above, FIGS. 6A-6C and 7A-7C illustrate a lamellar keratoplasty procedure wherein only a portion of the cornea 16'''' of the host eye 10'''' is removed during the procedure (i.e., a full-thickness corneal section is not removed). Although, the procedure of FIGS. 6A-6C and 7A-7C differs in several important respects from the abovedescribed procedures. In this embodiment, the corneal transplant is cross-linked in vitro. Then, using a femtosecond laser or an excimer laser, the surgeon carves out or ablates a three-dimensional (3D) corneal cross-linked augment from the donor cornea 20''' that exactly compensates for the refractive error of the recipient of the transplant. That is, the corneal cross-linked augment or inlay may be cut to the desired shape using a femtosecond laser, or the inlay may be shaped in vitro using an excimer laser prior to its implantation in the cornea 16'''' of the host eye 10''''. After making an internal pocket 28 in the recipient cornea 16'''' of the host eye 10'''' with a femtosecond laser, the cross-linked transplant is folded and implanted in a predetermined fashion inside the host's corneal pocket 28 to provide stability to the eye 10'''' having keratoconus, keratoglobus, a thin cornea or abnormal corneal curvature, thereby preventing future corneal ectasia in this eye 10'''' and correcting its refractive errors. Advantageously, the procedure of this embodiment comprises a lamellar cross-linked corneal transplantation, which additionally results in simultaneous correction of the refractive error of the eye 10'''' of the patient. As used herein, the term "lenslet" refers to a lens implant configured to be implanted in a cornea of an eye. The lens implant may be formed from an organic material, a synthetic material, or a combination of organic and synthetic materials.

Figure 6A:
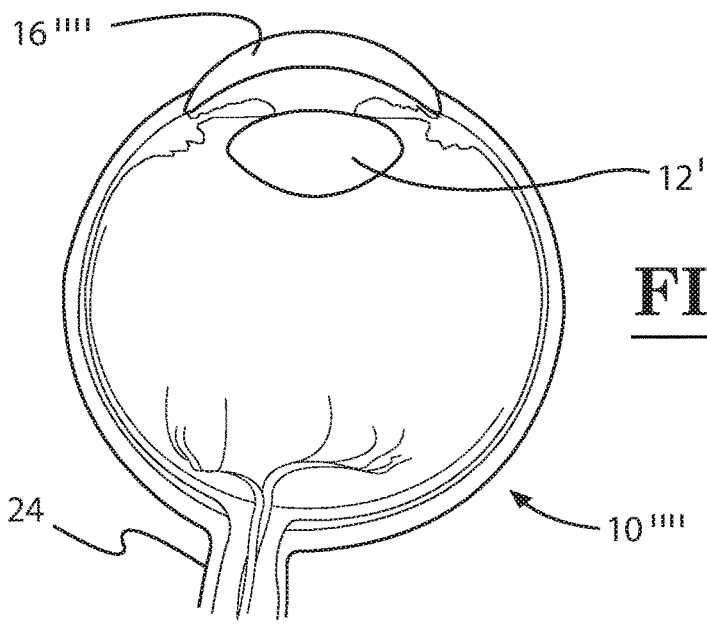
FIG. 6A is a side cross-sectional view of a host eye prior to an transplant procedure.
Figure 6B:
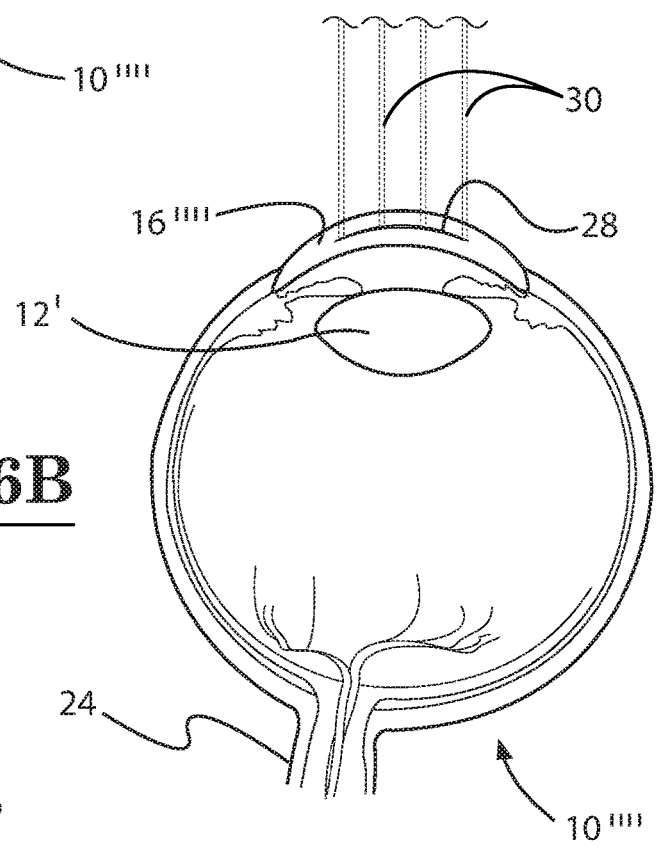
FIG. 6B is another side cross-sectional view of the host eye of FIG. 6A, which illustrates a creation of a corneal pocket therein.

Now, with reference to FIGS. 6A-6C and 7A-7C, the illustrative embodiment will be described in further detail. The host eye 10'''' with lens 12', cornea 16'''', and optic nerve 24 is shown in FIG. 6A, while the donor cornea 20''' is depicted in FIG. 7A. The donor cornea 20''' of FIG. 7A may be a cross-linked cornea of a cadaver or a tissue culture-grown cornea that has been cross-linked. Turning to FIG. 6B, it can be seen that an internal corneal pocket 28 is created in the cornea 16'''' of the host eye 10'''' (e.g., by using a suitable laser, which is indicated diagrammatically in FIG. 6B by lines 30).

Figure 7A:
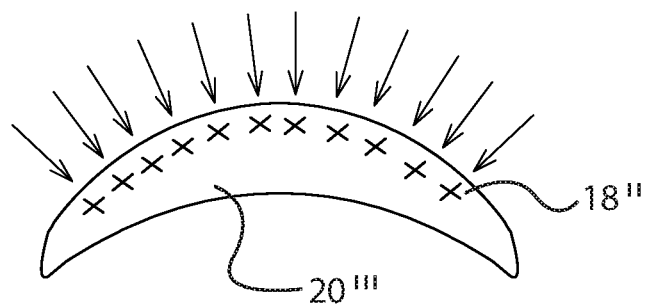
FIG. 7A is a partial side cross-sectional view of a donor cornea being cross-linked prior to being shaped for use in a transplant procedure.
Figure 7B:
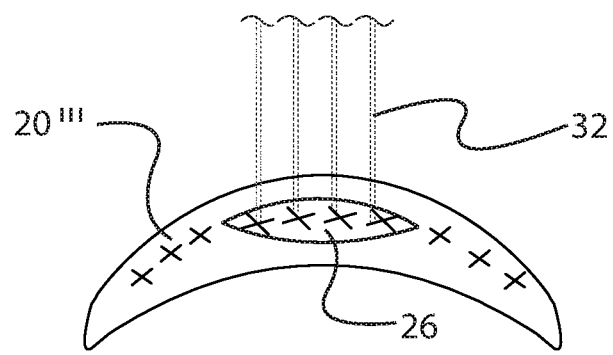
FIG. 7B is another partial side cross-sectional view of the donor cornea of FIG. 7A, which illustrates the cutting of a cross-linked lamellar lenslet from a remainder of the cross-lined donor cornea.
Figure 7C:
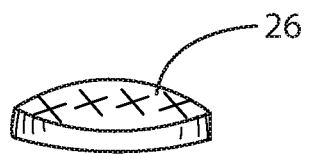
FIG. 7C is a side cross-sectional view of the cross-linked lamellar lenslet after it has been appropriately shaped and removed from the donor cornea of FIGS. 7A and 7B.

In FIG. 7A, the cross-linking 18'' of the donor cornea 20''' is diagrammatically illustrated. As mentioned in the preceding embodiments, it is to be understood that all or just a part of the donor cornea 20''' may be cross-linked. Then, after the donor cornea 20''' of FIG. 7A has been cross-linked (e.g., by using a photosensitizer in the form of riboflavin and UV radiation as described above), it can be seen that a cross-linked lamellar lenslet 26 is cut out from the remainder of the donor cornea 20''' (e.g., by using a suitable laser, which is indicated diagrammatically in FIG. 7B by lines 32) such that it has the necessary shape for implantation into the host eye 10''''. As explained above, the cross-linked lamellar lenslet 26 may be cut from the donor cornea 20''' and appropriately shaped using a femtosecond laser or an excimer laser. The cross-linked lamellar lenslet 26 is capable of being prepared to any requisite shape using either the femtosecond laser or the excimer laser. FIG. 7C illustrates the shaped cross-linked lamellar lenslet 26 after it has been removed from the remainder of the donor cornea 20'''.

Figure 6C:
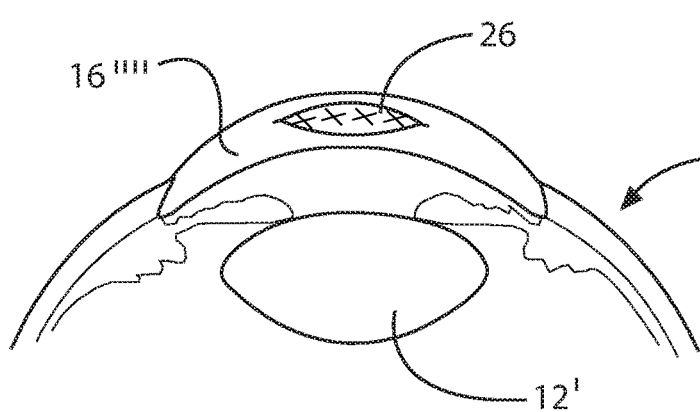
FIG. 6C is another side cross-sectional view of the host eye of FIG. 6A, which illustrates an implantation of the cross-linked lamellar lenslet into the host eye.

Finally, as shown in FIG. 6C, the cross-linked lamellar lenslet 26 is implanted into the cornea 16'''' of the host eye 10'''' of the patient in the location where the pocket 28 was previously formed. Because the shape of the transplant corresponds to that of the pocket 28 formed in the eye 10'''', the transplant sits comfortably in its position in the host cornea 16''''. As described above, after implantation of the cross-linked lamellar lenslet 26 into the eye 10'''', the refractive errors of the eye 10'''' have been corrected because the cross-linked lamellar lenslet 26 has been appropriately shaped to compensate for the specific refractive errors of the host eye 10'''' prior to its implantation into the eye 10''''. In addition, as explained above, the implantation of the cross-linked lamellar lenslet 26 provides additional stability to an eye having keratoconus, keratoglobus, a thin cornea, or abnormal corneal curvature.

Another illustrative embodiment of a corneal lenslet implantation procedure with a cross-linked cornea is shown in FIGS. 8-14. In general, the procedure illustrated in these figures involves forming a two-dimensional cut into a cornea of an eye; creating a three-dimensional pocket in the cornea of the eye, cross-linking the interior stroma, and inserting a lenslet or lens implant into the three-dimensional pocket after the internal stromal tissue has been cross-linked.

Figure 8:
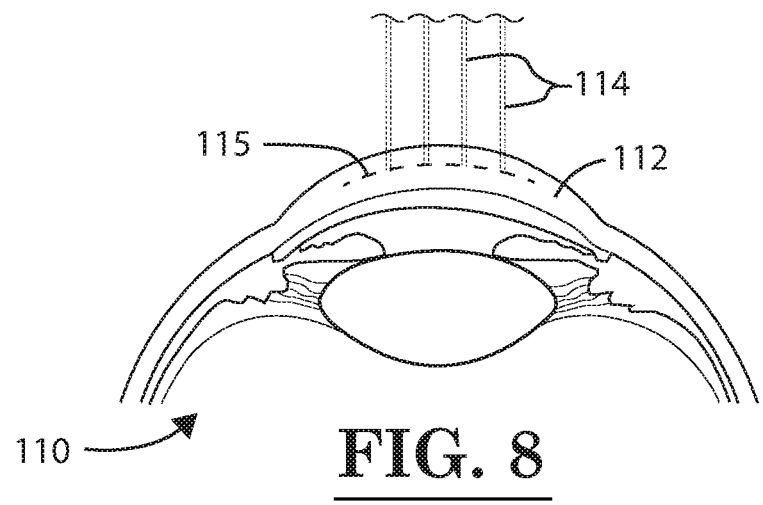
FIG. 8 is a partial side cross-sectional view illustrating the formation of a two-dimensional cut into a cornea of an eye, according to another embodiment of the invention.

Initially, in FIG. 8, the forming of a two-dimensional cut 115 into the cornea 112 of the eye 110 is diagrammatically illustrated. In particular, as shown in the illustrative embodiment of FIG. 8, the two-dimensional cut 115 is formed by making an intrastromal incision in the cornea 112 of the eye 110 using a femtosecond laser (i.e., the incision is cut in the cornea 112 using the laser beam(s) 114 emitted from the femtosecond laser). Alternatively, the two-dimensional cut 115 may be formed in the cornea 112 of the eye 110 using a knife.

Figure 9:
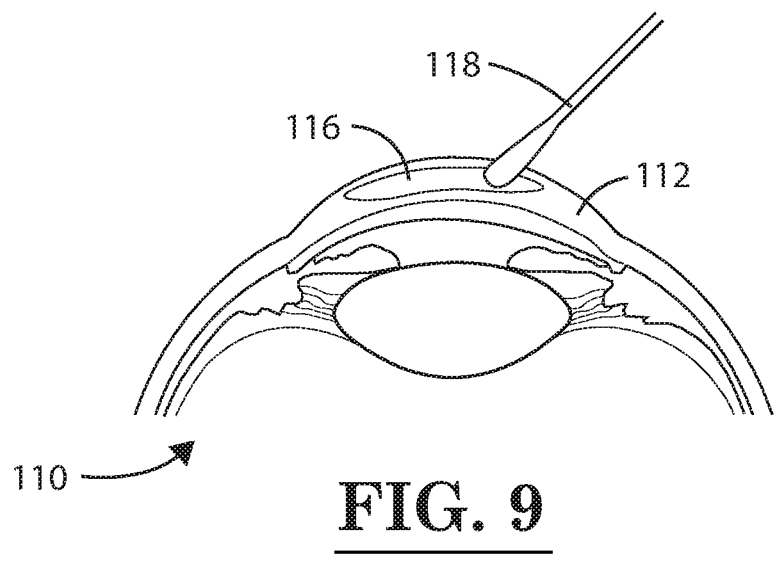
FIG. 9 is another partial side cross-sectional view of the eye of FIG. 8, which illustrates the creation of a three-dimensional pocket in the cornea of the eye.

Then, in FIG. 9, the forming of a three-dimensional corneal pocket 116 in the cornea 112 of the eye 110 is diagrammatically illustrated. In particular, as shown in the illustrative embodiment of FIG. 9, the three-dimensional corneal pocket 116 is formed by using a spatula 118. The formation of the intracorneal pocket 116 in the cornea 112 of the eye 110 allows one to gain access to the tissue surrounding the pocket 116 (i.e., the interior stromal tissue surrounding the pocket 116).

Turning again to FIGS. 8 and 9, in the illustrative embodiment, the corneal pocket 116 formed in the cornea 112 of the eye 110 may be in the form of an intrastromal corneal pocket cut into the corneal stroma. A femtosecond laser may be used to form a 2-dimensional cut into the cornea 112, which is then opened with a spatula 118 to create a 3-dimensional pocket 116. In one embodiment, a piece of the cornea 112 or a cornea which has a scar tissue is first cut with the femtosecond laser. Then, the cavity is cross-linked before filling it with an implant or inlay 128 to replace the lost tissue with a clear flexible inlay or implant 128 (see FIG. 12).

In one embodiment, a three-dimensional (3D) uniform circular, oval, or squared-shaped corneal pocket 116 is cut with a femtosecond laser and the tissue inside the pocket is removed to produce a three-dimensional (3D) pocket 116 to be cross-linked with riboflavin and implanted with a prepared implant.

Figure 10:
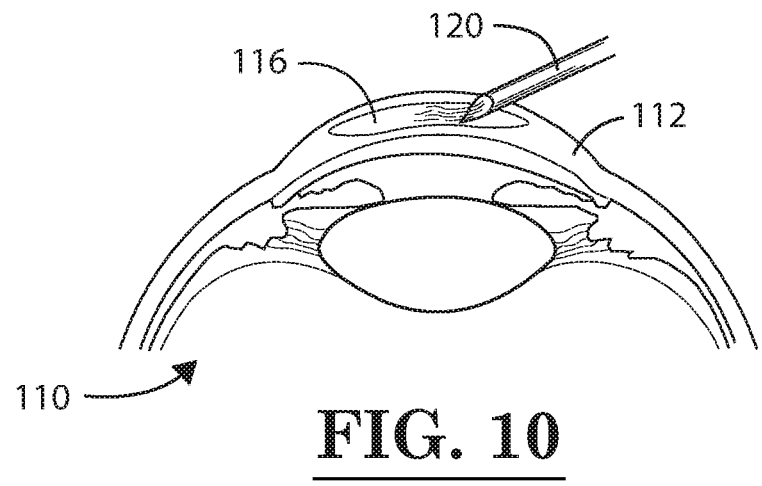
FIG. 10 is yet another partial side cross-sectional view of the eye of FIG. 8, which illustrates the injection of a photosensitizer into the three-dimensional pocket in the cornea of the eye.

After the pocket 116 is formed using the spatula 118, a photosensitizer is applied inside the three-dimensional pocket 116 so that the photosensitizer permeates the tissue surrounding the pocket 116 (see FIG. 10). The photosensitizer facilitates the cross-linking of the tissue surrounding the pocket 116. In the illustrative embodiment, the photosensitizer is injected with a needle 120 inside the stromal pocket 116 without lifting the anterior corneal stroma so as to cover the internal surface of the corneal pocket 116. In one or more embodiments, the photosensitizer or cross-linker that is injected through the needle 120 inside the stromal pocket comprises riboflavin, and/or a liquid suspension having nanoparticles of riboflavin disposed therein. Preferably, the cross-linker has between about 0.1% riboflavin to about 100% riboflavin therein (or between 0.1% and 100% riboflavin therein). Also, in one or more embodiments, an excess portion of the photosensitizer in the pocket 116 may be aspirated through the needle 120 until all, or substantially all, of the excess portion of the photosensitizer is removed from the pocket 116 (i.e., the excess cross-linker may be aspirated through the same needle so that the pocket 116 may be completely emptied or substantially emptied).

Figure 11A:
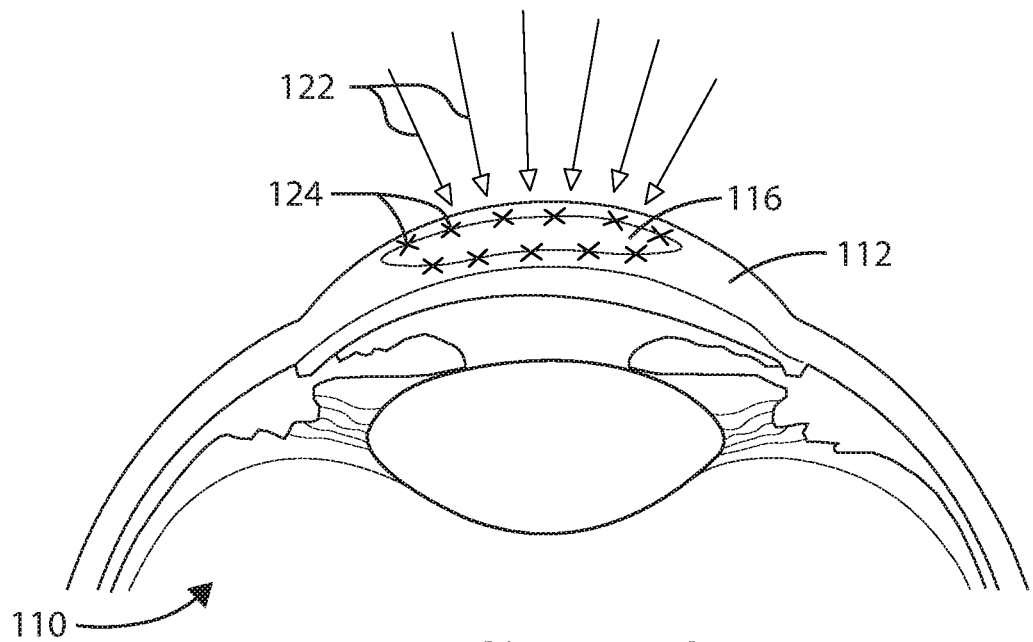
FIG. 11A is still another partial side cross-sectional view of the eye of FIG. 8, which illustrates the irradiation of the stromal tissue surrounding the three-dimensional pocket of the eye using ultraviolet radiation delivered from outside of the cornea.

Next, turning to the illustrative embodiment of FIG. 11A, shortly after the photosensitizer is applied inside the pocket 116, the cornea 112 of the eye 110 is irradiated from the outside using ultraviolet (UV) radiation 122 so as to activate cross-linkers in the portion of the tissue surrounding the three-dimensional pocket 116, and thereby stiffen the cornea 112, prevent corneal ectasia of the cornea 112, and kill cells in the portion of the tissue surrounding the pocket 116. In the illustrative embodiment, the ultraviolet light used to irradiate the cornea 112 may have a wavelength between about 370 nanometers and about 380 nanometers (or between 370 nanometers and 380 nanometers). Also, in the illustrative embodiment, only a predetermined anterior stromal portion 124 of the cornea 112 to which the photosensitizer was applied is cross-linked (i.e., the surrounding wall of the corneal pocket 116), thereby leaving an anterior portion of the cornea 112 and a posterior stromal portion of the cornea 112 uncross-linked. That is, in the illustrative embodiment, the entire corneal area inside the cornea 112 exposed to the cross-linker is selectively cross-linked, thereby leaving the anterior part of the cornea 112 and the posterior part of the stroma uncross-linked. The portion of the cornea 112 without the cross-linker is not cross-linked when exposed to the UV radiation. In an alternative embodiment, the cornea 112 may be irradiated using wavelengths of light other than UV light as an alternative to, or in addition to being irradiated using the ultraviolet (UV) radiation 122 depicted in FIG. 11A. Also, microwave radiation may be used synergistically or additively to correct non-invasively the remaining refractive error(s) of the cornea.

Figure 11B:
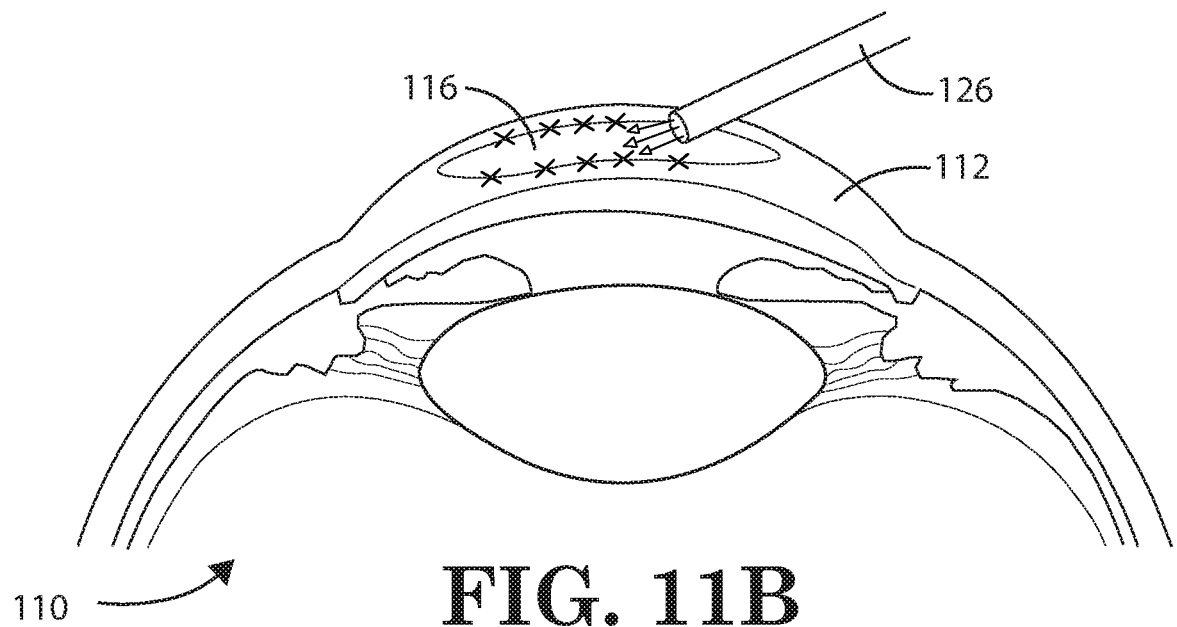
FIG. 11B is yet another partial side cross-sectional view of the eye of FIG. 8, which illustrates the irradiation of the stromal tissue surrounding the three-dimensional pocket of the eye using a fiber optic delivering ultraviolet radiation inside the three-dimensional pocket, according to an alternative embodiment of the invention.

Alternatively, as shown in FIG. 11B, a fiber optic 126 may be inserted into the corneal pocket 116 so as to apply the ultraviolet radiation and activate the photosensitizer in the wall of the corneal pocket 116. When the fiber optic 126 is used to irradiate the wall of the pocket 116, the ultraviolet radiation is applied internally, rather than externally as depicted in FIG. 11A.

Figure 12:
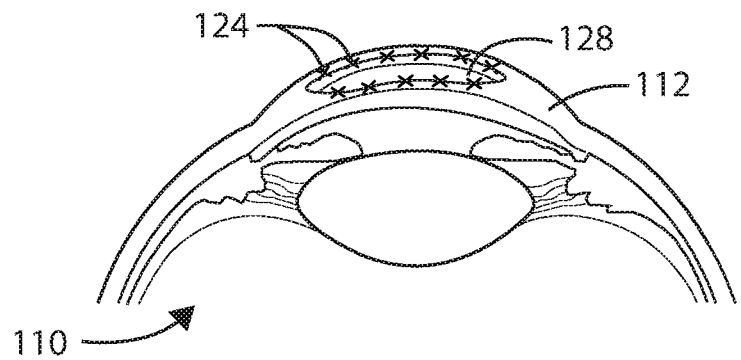
FIG. 12 is still another partial side cross-sectional view of the eye of FIG. 8, which illustrates a lens implant inserted into the pocket so as to change the refractive properties of the eye.

Now, with reference to FIG. 12, it can be seen that, after the wall of the corneal pocket 116 has been stiffened and is devoid of cellular elements by the activation of the cross-linkers, a lens implant 128 is inserted into the corneal pocket 116 in order to change the refractive properties of the eye. In particular, in the illustrated embodiment, the lens implant 128 is inserted through a small incision, and into the corneal pocket 116, using forceps or microforceps. In one or more embodiments, the lens implant 128 that is inserted inside the pocket 116 in the cornea 112 is flexible and porous. Also, in one or more embodiments, the lens implant 128 may comprise a hybrid lens implant with an organic outer portion and a synthetic inner portion. The organic outer portion of the hybrid lens implant may be made from a transparent, hydrophilic organic polymer, while the synthetic inner portion of the hybrid lens implant may be made from a transparent, gas permeable, porous flexible polymer. For example, the transparent, hydrophilic polymer forming the organic outer portion may be formed from collagen, chitosan, poloxamer, polyethylene glycol, or a combination thereof (or any other transparent hydrophilic coating which can be deposited over the entire lens surface), while the flexible polymer forming the synthetic inner portion of the hybrid lens implant may be formed from silicone, acrylic, polymetacrylate, hydrogel, or a combination thereof. The surface of the lens implant 128 may have the appropriate shape to reshape the cornea 112 or the dioptric power to nullify the remaining spheric or astigmatic error of the eye. More particularly, in one or more embodiments, the lens implant 128 may have one of: (i) a concave surface to correct myopic refractive errors (i.e., a minus lens for correcting nearsightedness), (ii) a convex surface to correct hyperopic refractive errors (i.e., a plus lens for correcting farsightedness), or (iii) a toric shape to correct astigmatic refractive errors.

In the illustrative embodiment, the irradiation of the cornea 112 using the ultraviolet (UV) radiation 122 only activates cross-linkers in the portion of the stromal tissue surrounding the three-dimensional pocket 116, and only kills the cells in the portion of the tissue surrounding the pocket 116, so as to leave only a thin layer of cross-linked collagen to prevent an immune response and rejection of the lens implant 128 and/or encapsulation by fibrocytes, while preventing post-operative dry eye formation. In addition to preventing encapsulation of the lens implant 128 by fibrocytes, the cross-linking of the stromal tissue surrounding the pocket 116 also advantageously prevents corneal haze formation around the lens implant 128. That is, the cross-linking of the stromal tissue surrounding the lens implant 128 prevents formation of myofibroblast from surrounding keratocytes, which then convert gradually to fibrocytes that appear as a haze, and then white encapsulation inside the cornea, thereby causing light scattering in front of the patient's eye.

Figure 13:
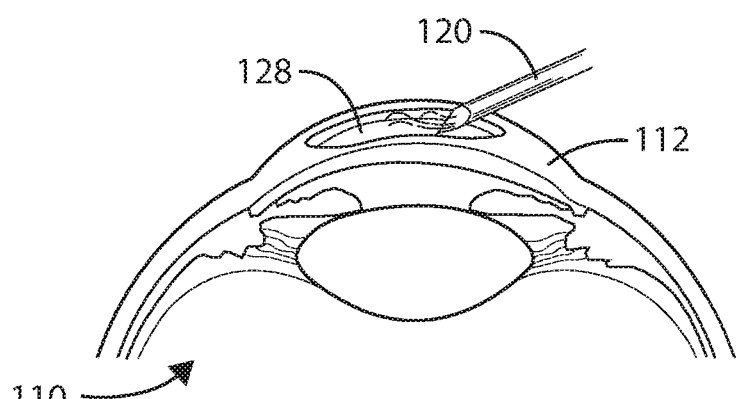
FIG. 13 is yet another partial side cross-sectional view of the eye of FIG. 8, which illustrates the reinjection of a photosensitizer into the three-dimensional pocket with the lens implant disposed therein so that the cross-linking procedure may be repeated.
Figure 14:
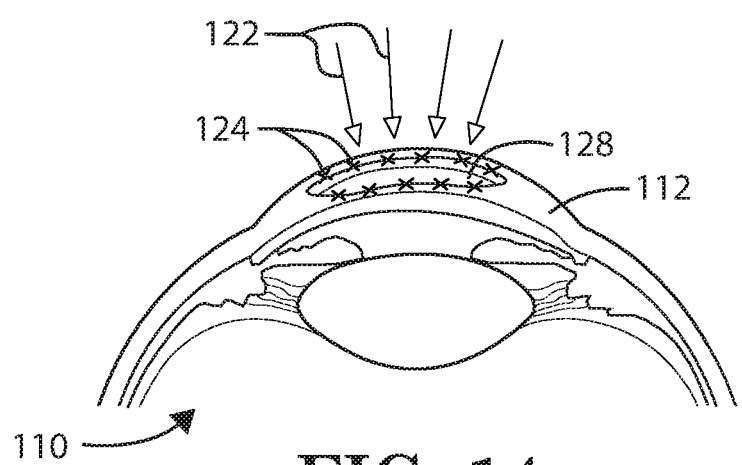
FIG. 14 is still another partial side cross-sectional view of the eye of FIG. 8, which illustrates the re-irradiation of the stromal tissue surrounding the three-dimensional pocket of the eye during the repetition of the cross-linking procedure.

As shown in FIGS. 13 and 14, the crosslinking procedure described above may be repeated after the lens implant 128 is implanted so as to prevent any cellular invasion in the area surrounding the implant 128. Initially, with reference to FIG. 13, the photosensitizer is reinjected inside the space between the lens implant 128 and the surrounding corneal tissue using a needle 120. In one or more embodiments, the needle 120 for injecting the photosensitizer may comprise a 30-32 gauge needle. Then, after the reinjection of the cross-linker, the cornea 112 is re-irradiated with ultraviolet radiation 122 to cross-link the tissue surrounding the lens implant 128 so as to prevent cellular migration towards the lens implant 128 (see FIG. 14).

In one or more embodiments, the lens implant or inlay 128 may be prepared ahead of time with known techniques, wherein the inlay 128 may be coated with a biocompatible material, such as collagen, elastin, polyethylene glycol, biotin, streptavidin, etc., or a combination thereof. The inlay 128 and the coating may be cross-linked with a photosensitizer or cross-linker, such as riboflavin, prior to being implanted into the pocket 116 in the cornea 112 of the eye.

In another embodiment, the lens implant or inlay 128 may be silicone, methacrylate, hydroxyethylmethacrylate (HEMA), or any other biocompatible transparent material, or a mixture thereof. The lens implant or inlay 128 also may be coated with materials, such as collagen or elastin, and may have a desired thickness of from 2 microns to 70 microns or more.

In yet another embodiment, the lens implant or inlay 128 is formed from an eye bank cornea, or a cross-linked eye bank cornea, etc. In general, there is a tremendous paucity of normal cadaver corneas for total or partial implants, such as for a corneal transplant of a corneal inlay. Because all the cellular elements are killed during the crosslinking of the corneal inlay, and because the corneal collagen is cross-linked and denatured, the remaining collagenous elements are not immunogenic when implanted inside the body or in the cornea of a patient. Advantageously, the prior cross-linking of the organic material, such as in the cadaver cornea, permits transplantation of the corneal inlay from an animal or human cornea or any species of animal to another animal or human for the first time without inciting a cellular or humoral response by the body, which rejects the inlay. Thus, cross-linking transparent cadaveric tissue for corneal transplantation, or as an inlay to modify of the refractive power of the eye, is highly beneficial to many patients who are on the waiting list for a corneal surgery. In addition, the surgery may be planned ahead of time without necessitating the urgency of the surgery when a fresh cadaver eye becomes available. In one or more embodiments, the collagens may be driven from the animal cornea, and cross-linked. Also, in one or more embodiments, the implant or inlay 128 may be made of cross-linked animal cornea or human cornea that is cut using a femtosecond laser to any desired shape and size, and then ablated with an excimer laser or cut with a femtosecond laser to a have a desired refractive power.

Figure 15:
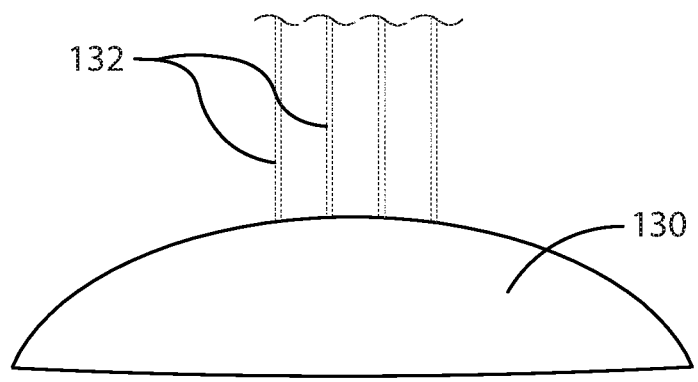
FIG. 15 is a side cross-sectional view illustrating the creation of a lens implant from an organic block of polymer using a excimer laser.
Figure 16:
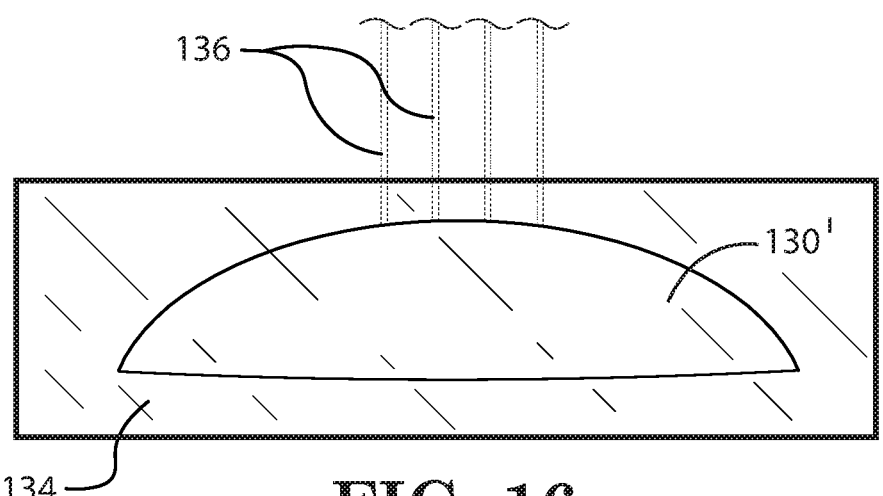
FIG. 16 is a side cross-sectional view illustrating the cutting of a lens implant from an organic block of polymer using a femtosecond laser.

For example, as shown in FIG. 15, the lens implant or inlay 130 may be formed from an organic block of a polymer (e.g., donor cornea) by cutting the lens implant 130 using an excimer laser (e.g., by using the laser beam(s) 132 emitted from the excimer laser). Alternatively, referring to FIG. 16, the lens implant or inlay 130' may be formed from an organic block 134 of a polymer (e.g., donor cornea) by cutting the lens implant 130' from the block 134 using a femtosecond laser or a computerized femto-system (e.g., by using the laser beam(s) 136 emitted from the femtosecond laser).

Figure 17:
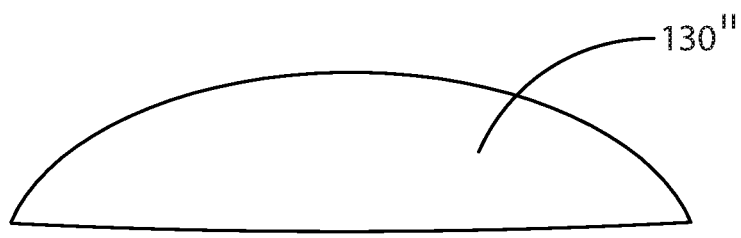
FIG. 17 is a side cross-sectional view illustrating a lens implant that has been formed using a three-dimensional printing technique or a molding technique.

In still another embodiment, as depicted in FIG. 17, the lens implant or inlay 130" is made using three-dimensional (3D) printing technology or a molding technique in order to form the lens implant or inlay 130" into the desired shape, size or thickness. The transparent material of the 3D-printed implant or inlay 130" may be coated with one or more biocompatible polymers and cross-linked prior to the implantation.

In yet another embodiment, after the implantation of an intraocular lens, the remaining refractive error of the eye may be corrected by the implantation of a lens implant or inlay 128 in the cross-linked pocket 116 of the cornea 112, thereby eliminating the need for entering the eye cavity to replace the original intraocular lens.

In still another embodiment, the remaining refractive error of the eye is corrected after an intraocular lens implantation by placing an inlay 128 on the surface of the cornea 112 of the patient while the shape of the cornea 112 is corrected with an excimer laser and wavefront optimized technology so that the patient is provided instant input on its effect on his or her vision. In this embodiment, an inlay similar to a contact lens is placed on the cornea 112 that, after correction, matches the desired refractive correction of the eye, and then, subsequently, the inlay 128 is implanted inside the cross-linked corneal pocket 116.

In yet another embodiment, the implant or inlay 128 may be ablated with an excimer laser for implantation in the cross-linked pocket 116, or after cross-linking the exposed corneal stroma in LASIK surgery.

In still another embodiment, a small amount of hyaluronic acid or a viscous fluid is injected into the pocket 116 prior to the implantation of the implant or inlay 128 so as to simplify the insertion of the implant or inlay 128 in the corneal pocket 116.

In yet another embodiment, the implant or inlay 128 is prepared having four marking holes of 0.1-2 millimeter (mm) in diameter in the inlay periphery at an equally sized distances so that the implant 128 may be rotated with a hook, if desired, after the implantation as needed to match the axis of an astigmatic error of the eye during the surgery as measured simultaneously with a wavefront technology system, such as an Optiwave Refractive Analysis (ORA) system or Holos® system, which are commercially available for measurement of astigmatism or its axis.

In still another embodiment, the implant or inlay 128 is located on the visual axis and may provide 1 to 3 times magnification for patients whose macula is affected by a disease process needing magnifying glasses for reading, such as in age-related macular degeneration, macular edema, degenerative diseases of the retina, etc. Because these eyes cannot be used normally for reading without external magnifier glasses, providing magnification by a corneal implant to one eye assists the patients in being able to read with one eye and navigate the familiar environment with their other eye.

In yet another embodiment, the surface of the cornea 112 is treated after surgery in all cases daily with an anti-inflammatory agent, such as steroids, nonsteriodal anti-inflammatory drugs (NSAIDs), immune-suppressants, such as cyclosporine A or mycophenolic acid, anti-proliferative agents, antimetabolite agents, or anti-inflammatory agents (e.g., steroids, NSAIDS, or antibiotics etc.) to prevent inflammatory processes after the corneal surgery, inlay implantation or crosslinking, while stabilizing the integrity of the implant 128 and preventing future cell growth in the organic implant or the adjacent acellular corneal tissue. In this embodiment, the medication is injected in the corneal pocket 116 along with the implantation or the implant 128 is dipped in the medication first, and then implanted in the cross-linked corneal pocket 116.

In still another embodiment, a cross-linked corneal inlay is placed over the cross-linked corneal stroma after a LASIK incision, and is abated to the desired size with an excimer laser using a topography guided ablation. By means of this procedure, the refractive power of the eye is corrected, while simultaneously providing stability to an eye prone to conceal ectasia postoperatively after a LASIK surgery. Then, the LASIK flap is placed back over the implant.

Figure 18:
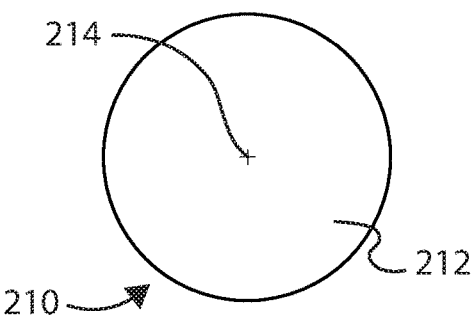
FIG. 18 is a front view of a cornea of an eye, according to yet another embodiment of the invention.

Yet another illustrative embodiment of a corneal lenslet implantation procedure with a cross-linked cornea is shown in FIGS. 18-23. In general, the procedure illustrated in these figures involves initially making an intrastromal square pocket surrounding the visual axis of the eye, and then, after forming the initial square pocket, a three-dimensional circular portion of diseased or weak stromal tissue is cut, removed, and replaced with a circular implant which fits into the circle that borders the four sides of the square. A front view of the cornea 212 of the eye 210 with the centrally-located visual axis 214 is illustrated in FIG. 18. Advantageously, in the illustrative embodiment of FIGS. 18-23, corneal tissue removal around the visual axis is greatly facilitated, and nearly perfect centration of the lens implant or inlay 220 about the visual axis is possible because the lens implant 220 fits within a depressed circular recess at the bottom of the pocket 216. As such, the undesirable decentering of the lens implant is prevented.

Figure 19:
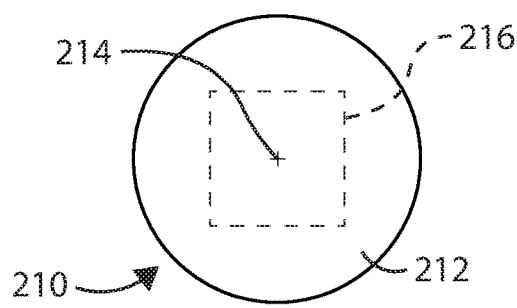
FIG. 19 is another front view of the cornea of the eye of FIG. 18, wherein a square-shaped intrastromal pocket has been formed in the cornea of the eye.

Initially, in FIG. 19, the forming of an intrastromal square-shaped pocket 216 surrounding the visual axis 214 (represented by a plus sign) in the cornea 212 of the eye 210 is diagrammatically illustrated. In particular, as shown in the illustrative embodiment of FIG. 19, the square-shaped pocket 216 is formed by making a two-dimensional intrastromal incision in the cornea 212 of the eye 210 using a femtosecond laser (i.e., the incision is cut in the cornea 212 using the laser beam(s) emitted from the femtosecond laser).

Figure 21:
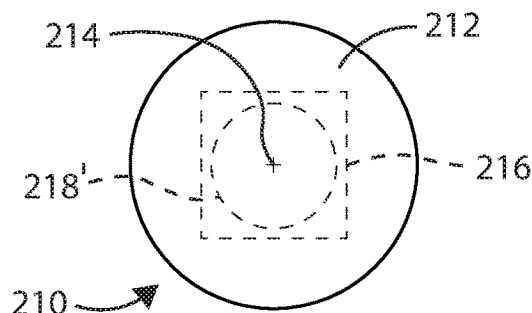
FIG. 21 is still another front view of the cornea of the eye of FIG. 18, wherein a circular three-dimensional portion of tissue having second diameter has been removed from the area within the square-shaped intrastromal pocket, the second diameter of the circular three-dimensional portion of tissue in FIG. 21 being larger than the first diameter of the circular three-dimensional portion of tissue in FIG. 20.
Figure 20:
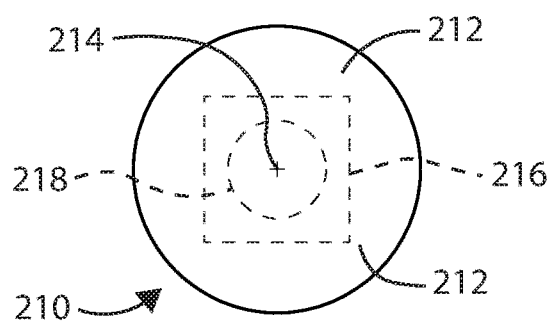
FIG. 20 is yet another front view of the cornea of the eye of FIG. 18, wherein a circular three-dimensional portion of tissue having a first diameter has been removed from the area within the square-shaped intrastromal pocket.

Then, in FIG. 20, the removal of a three-dimensional circular portion 218 of diseased or weak stromal tissue in the cornea 212 of the eye 210 is diagrammatically illustrated. In particular, as shown in the illustrative embodiment of FIG. 20, the three-dimensional circular stromal tissue portion 218 has a first diameter, which is less than a width of the square-shaped pocket 216 so that the three-dimensional circular stromal tissue portion 218 is disposed within the boundaries of the square-shaped pocket 216. The three-dimensional circular stromal tissue portion 218' depicted in FIG. 21 is generally similar to that illustrated in FIG. 20, except that the three-dimensional circular stromal tissue portion 218' depicted in FIG. 21 has a second diameter that is slightly larger than the first diameter of the three-dimensional circular stromal tissue portion 218 in FIG. 20. As such, the periphery of the three-dimensional circular stromal tissue portion 218' depicted in FIG. 21 is disposed closer to the square-shaped pocket 216, but still within the confines of the square-shaped pocket 216. In the illustrative embodiment, the three-dimensional circular stromal tissue portion 218, 218' may be removed using forceps or micro-forceps. In an exemplary embodiment, the diameter of the circular stromal tissue portion 218, 218' that is removed from the cornea 212 is between approximately 5 millimeters and approximately 8 millimeters, inclusive (or between 5 millimeters and 8 millimeters, inclusive).

In an alternative embodiment of the corneal lenslet implantation procedure, three (3) sequential cuts may be made in the stromal portion of the cornea 212 of the eye 210 using a femtosecond laser in order to form the pocket. First, a lower circular cut or incision centered about the visual axis (i.e., a lower incision with the patient in a supine position) is made using the femtosecond laser. Then, a second vertical cut is made above the lower incision using the femtosecond laser to form the side(s) of a circular cutout portion. Finally, a third square or circular cut (i.e., an upper incision) is made above the vertical cut using the femtosecond laser. In the illustrative embodiment, the lower incision is parallel to the upper incision, and the vertical cut extends between lower incision and the upper incision. In this alternative embodiment, the three-dimensional circular stromal tissue cutout portion bounded by the lower incision on the bottom thereof, the vertical cut on the side(s) thereof, and the upper incision on the top thereof is removed from the cornea 212 of the eye 210 using a pair of forceps. A cavity formed by the upper incision facilitates the removal of the three-dimensional circular stromal tissue cutout portion. As described above, the third cut or incision formed using the femtosecond laser may be an upper circular cut that is larger than the lower circular cut, rather than an upper square cut that is larger than the lower circular cut.

Figure 22:
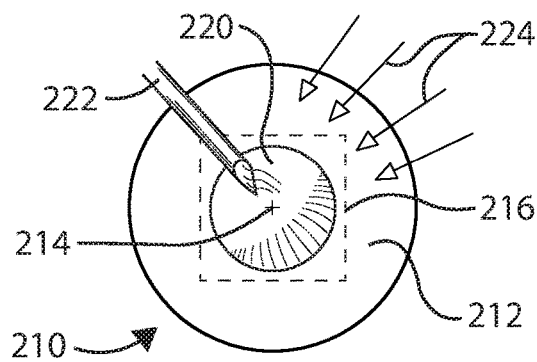
FIG. 22 is yet another front view of the cornea of the eye of FIG. 18, wherein a circular lens implant has been implanted in the area where the circular three-dimensional portion of tissue has been removed, and wherein a photosensitizer is being injected into the pocket in the cornea of the eye.

Turning to FIG. 22, after the three-dimensional circular stromal tissue portion 218, 218' is removed, a photosensitizer is applied inside the pocket 216 so that the photosensitizer permeates the tissue surrounding the pocket 216. The photosensitizer facilitates the cross-linking of the tissue surrounding the pocket 216. In the illustrative embodiment, the photosensitizer is injected with a needle 222 inside the stromal pocket 216. In one or more embodiments, the photosensitizer or cross-linker that is injected through the needle 222 inside the stromal pocket 216 comprises riboflavin, and/or a liquid suspension having nanoparticles of riboflavin disposed therein. Preferably, the cross-linker has between about 0.1% riboflavin to about 100% riboflavin therein (or between 0.1% and 100% riboflavin therein). Also, in one or more embodiments, an excess portion of the photosensitizer in the pocket 216 may be aspirated through the needle 222 until all, or substantially all, of the excess portion of the photosensitizer is removed from the pocket 216 (i.e., the excess cross-linker may be aspirated through the same needle 222 so that the pocket 216 may be completely emptied or substantially emptied).

Next, turning again to the illustrative embodiment of FIG. 22, shortly after the photosensitizer is applied inside the pocket 216, the cornea 212 of the eye 210 is irradiated from the outside using ultraviolet (UV) radiation 224 so as to activate cross-linkers in the portion of the tissue surrounding the three-dimensional pocket 216, and thereby stiffen the cornea 212, prevent corneal ectasia of the cornea 212, and kill cells in the portion of the tissue surrounding the pocket 216. In the illustrative embodiment, the ultraviolet light used to irradiate the cornea 212 may have a wavelength between about 370 nanometers and about 380 nanometers (or between 370 nanometers and 380 nanometers). Also, in the illustrative embodiment, only a predetermined anterior stromal portion of the cornea 212 to which the photosensitizer was applied is cross-linked (i.e., the surrounding wall of the corneal pocket 216), thereby leaving an anterior portion of the cornea 212 and a posterior stromal portion of the cornea 212 uncross-linked. That is, in the illustrative embodiment, the entire corneal area inside the cornea 212 exposed to the cross-linker is selectively cross-linked, thereby leaving the anterior part of the cornea 212 and the posterior part of the stroma uncross-linked. The portion of the cornea 212 without the cross-linker is not cross-linked when exposed to the UV radiation. In an alternative embodiment, the cornea 212 may be irradiated using wavelengths of light other than UV light as an alternative to, or in addition to being irradiated using the ultraviolet (UV) radiation 224 depicted in FIG. 22. Also, microwave radiation may be used synergistically or additively to correct non-invasively the remaining refractive error(s) of the cornea. In addition, in an alternative embodiment, the ultraviolet (UV) radiation may be applied after the implantation of the lens implant 220 to perform the crosslinking, rather than before the implantation of the lens implant 220 as described above. Further, rather than applying the ultraviolet (UV) radiation from outside the cornea 212, the stromal tissue of the pocket 216 may be irradiated from inside by means of a fiber optic, before or after the implantation of the lens implant 220.

Figure 23:
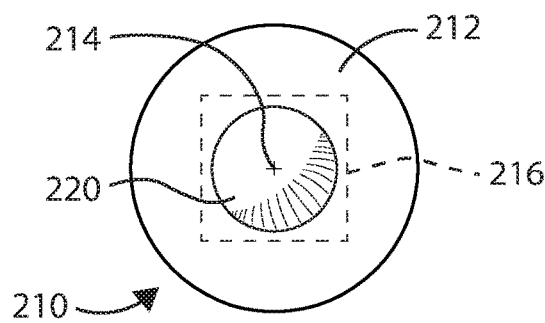
FIG. 23 is still another front view of the cornea of the eye of FIG. 18, wherein the circular lens implant is shown in the area where the circular three-dimensional portion of tissue was removed.

Now, with combined reference to FIGS. 22 and 23, it can be seen that, before or after the wall of the corneal pocket 216 has been stiffened and is devoid of cellular elements by the activation of the cross-linkers, a circular lens implant 220 is inserted into the circular recess at the bottom of the pocket 216 formed by the three-dimensional circular stromal tissue cutout portion 218, 218' that was removed. That is, the circular lens implant 220 fits within the periphery of the circular recess that borders the four sides of the squared-shaped pocket 216. In particular, in the illustrated embodiment, the circular lens implant 220 is inserted through a small incision, and into the circular recess at the bottom of the pocket 216 using forceps or microforceps. In the illustrative embodiment, the flexible lens implant 220 may be folded, inserted through the small incision, placed inside the circular recess at the bottom of the pocket 216, and finally unfolded through then small incision. In one or more embodiments, the lens implant 220 that is inserted inside the pocket 216 in the cornea 212 is flexible and porous. Also, in one or more embodiments, the lens implant 220 may comprise a hybrid lens implant with an organic outer portion and a synthetic inner portion. The organic outer portion of the hybrid lens implant may be made from a transparent, hydrophilic organic polymer, while the synthetic inner portion of the hybrid lens implant may be made from a transparent, gas permeable, porous flexible polymer. For example, the transparent, hydrophilic polymer forming the organic outer portion may be formed from collagen, chitosan, poloxamer, polyethylene glycol, or a combination thereof (or any other transparent hydrophilic coating which can be deposited over the entire lens surface), while the flexible polymer forming the synthetic inner portion of the hybrid lens implant may be formed from silicone, acrylic, polymetacrylate, hydrogel, or a combination thereof.

Advantageously, the lens implant 220 of the aforedescribed illustrative embodiment always remains perfectly centered around the visual axis 214 of the eye 210, and will not move because it is disposed within the circular recess at the bottom of the pocket 216. As explained above, the lens implant 220 may be formed from an organic material, synthetic material, polymeric material, and combinations thereof. The lens implant 220 may replace either a diseased tissue or create a new refractive power for the eye 210, as explained hereinafter.

In the illustrative embodiment, the lens implant 220 may correct the refractive errors of the eye 210. The refractive error correction may be done by the lens implant 220 having a curvature that changes the corneal surface of the cornea 212. Alternatively, the lens implant 220 may have a different index of refraction that corrects the refractive power of the cornea 212. In the illustrative embodiment, the lens implant 220 may have the appropriate shape to reshape the cornea 212 or the dioptric power to nullify the remaining spheric or astigmatic error of the eye. More particularly, in one or more embodiments, the lens implant 220 may have one of: (i) a concave anterior surface to correct myopic refractive errors (i.e., a minus lens for correcting nearsightedness), (ii) a convex anterior surface to correct hyperopic refractive errors (i.e., a plus lens for correcting farsightedness), or (iii) a toric shape to correct astigmatic refractive errors.

In the illustrative embodiment, the irradiation of the cornea 212 using the ultraviolet (UV) radiation 224 only activates cross-linkers in the portion of the stromal tissue surrounding the three-dimensional pocket 216, and only kills the cells in the portion of the tissue surrounding the pocket 216, so as to leave only a thin layer of cross-linked collagen to prevent an immune response and rejection of the lens implant 220 and/or encapsulation by fibrocytes, while preventing post-operative dry eye formation. In addition to preventing encapsulation of the lens implant 220 by fibrocytes, the cross-linking of the stromal tissue surrounding the pocket 216 also advantageously prevents corneal haze formation around the lens implant 220. That is, the cross-linking of the stromal tissue surrounding the lens implant 220 prevents formation of myofibroblast from surrounding keratocytes, which then convert gradually to fibrocytes that appear as a haze, and then white encapsulation inside the cornea, thereby causing light scattering in front of the patient's eye.

In the further illustrative embodiments described hereinafter, the cornea is cross-linked soon after the initial corneal transplant where a suture is placed around the implant to keep the implant in place until the tissue heals between the host and the corneal transplant, before the graft and often the suture itself can act as a foreign body inducing an immune response with neovascularization of the corneal transplant which will be rejected and become scarred. For example, in the aforedescribed embodiments, the cross-linking may be performed between two and three months after transplantation of the corneal graft or prosthesis in order to allow the transplantation area time to heal before the cross-linking procedure is performed.

Figure 24:
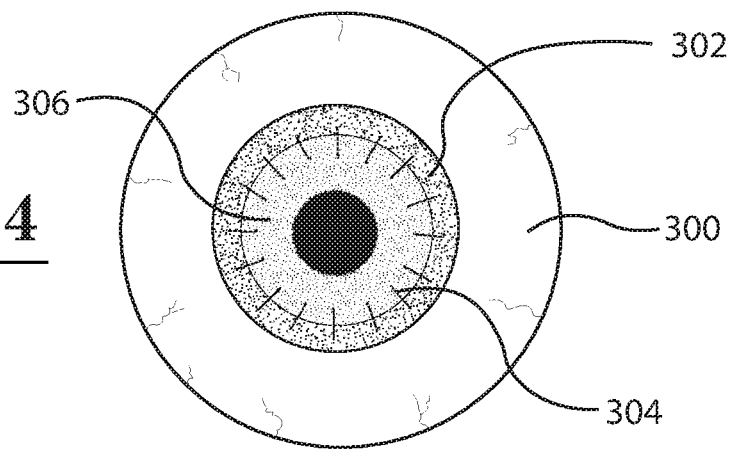
FIG. 24 is a front view of an eye where a corneal graft has been implanted in the cornea of the eye, according to still another embodiment of the invention.
Figure 25:
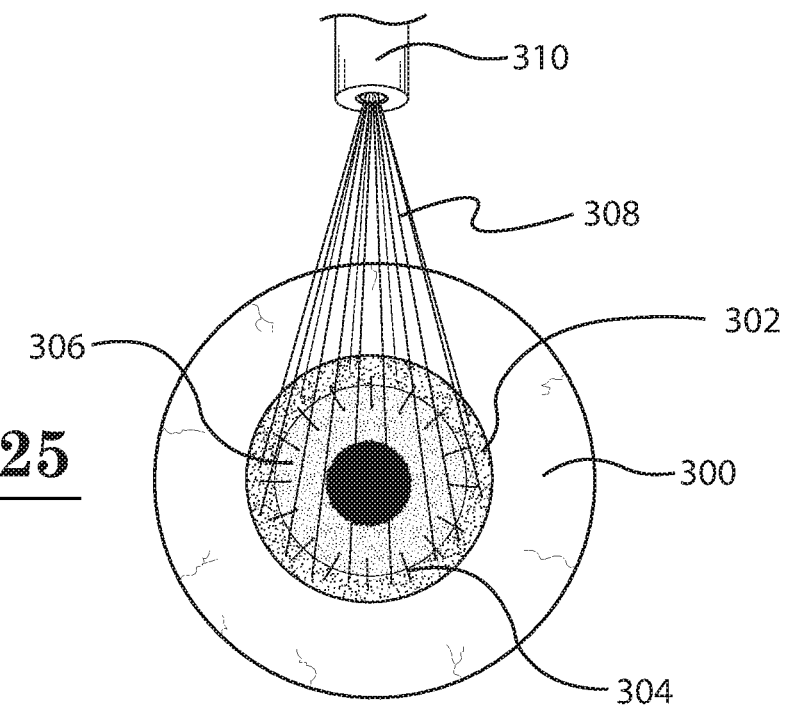
FIG. 25 is another front view of the eye of FIG. 24, wherein the application of ultraviolet radiation is being illustrated following the administration of a cross-linking agent or photosensitizer to the cornea of the eye.

A fifth illustrative embodiment is depicted in FIGS. 24 and 25. In this illustrative embodiment, shortly after corneal transplantation (see FIG. 24) the remaining peripheral host cornea 302 of the eye 300, the suture 304 and the transplant (i.e., the corneal graft 306) is treated with drops of 0.05-1% or more of riboflavin, CPP/nanoparticles, physiological solution or the use of another photosensitizer or cross-linking agent, that is applied to the cornea 302 for a period of a few minutes to 30 minutes. Then, the entire cornea 302 is irradiated with a UV laser 310 emitting ultraviolet radiation 308 of 370-400 nm wavelength, 1-30 mw/cm2 for a desired time of 1-30 minutes, depending on the concentration of the photosensitizer and the power of the laser light to cross-link the corneal collagen and damage the keratocytes in it, in at least one-third of the front thickness of the host cornea and the transplant to prevent an immune response to the transplant and its rejection (refer to FIG. 25).

Figure 26:
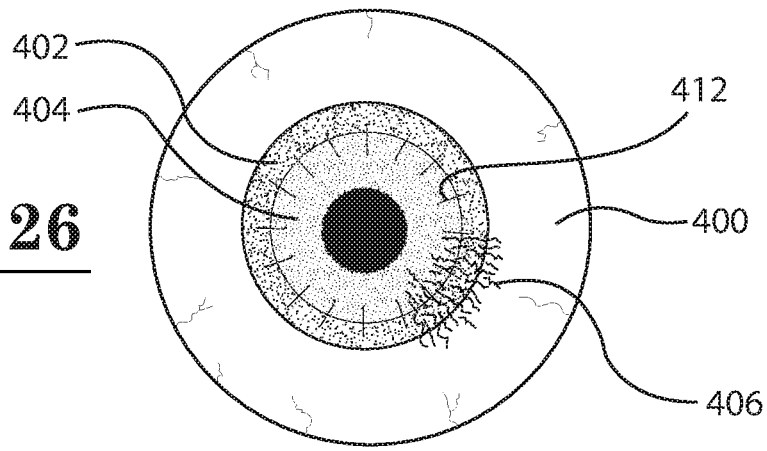
FIG. 26 is a front view of an eye where a corneal graft has been implanted in the cornea of the eye and neovascularization has occurred, according to yet another embodiment of the invention.
Figure 27:
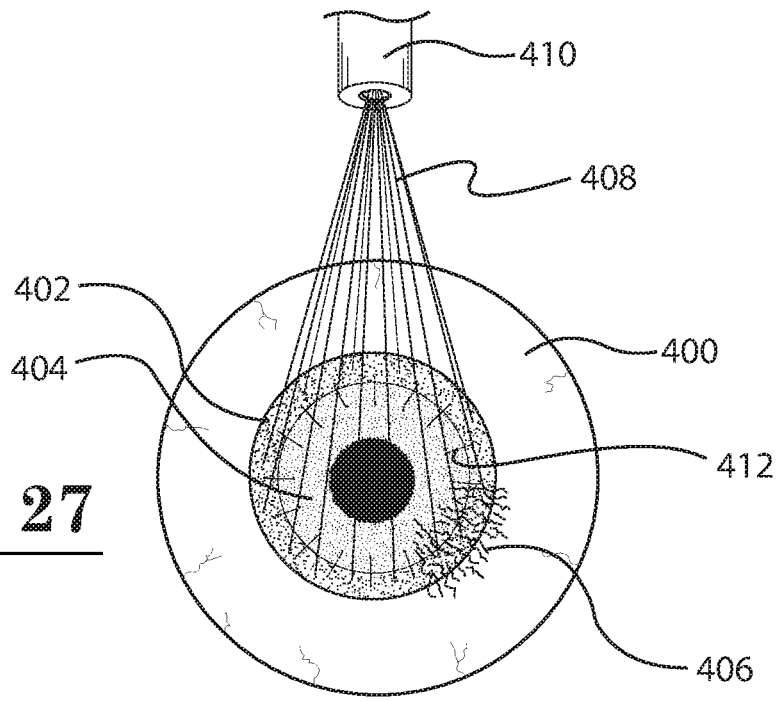
FIG. 27 is another front view of the eye of FIG. 26, wherein the application of ultraviolet radiation is being illustrated following the administration of a cross-linking agent or photosensitizer to the cornea of the eye.

A sixth illustrative embodiment is depicted in FIGS. 26 and 27. In this illustrative embodiment, the neovascularization 406 has started or has reached the edges of the transplanted cornea 404 with sutures 412 (see FIG. 26), one applies riboflavin or another photosensitizer to the anterior part of the cornea 402 of the eye 400 prior to the cross-linker molecule diffusing to the posterior corneal layers and the corneal endothelial cells under observation with a slit lamp, then the cornea 402 is irradiated with UV light 408 from a UV laser 410 as described previously to cross-link at least one half of the anterior thickness of the cornea 402.

Figure 28:
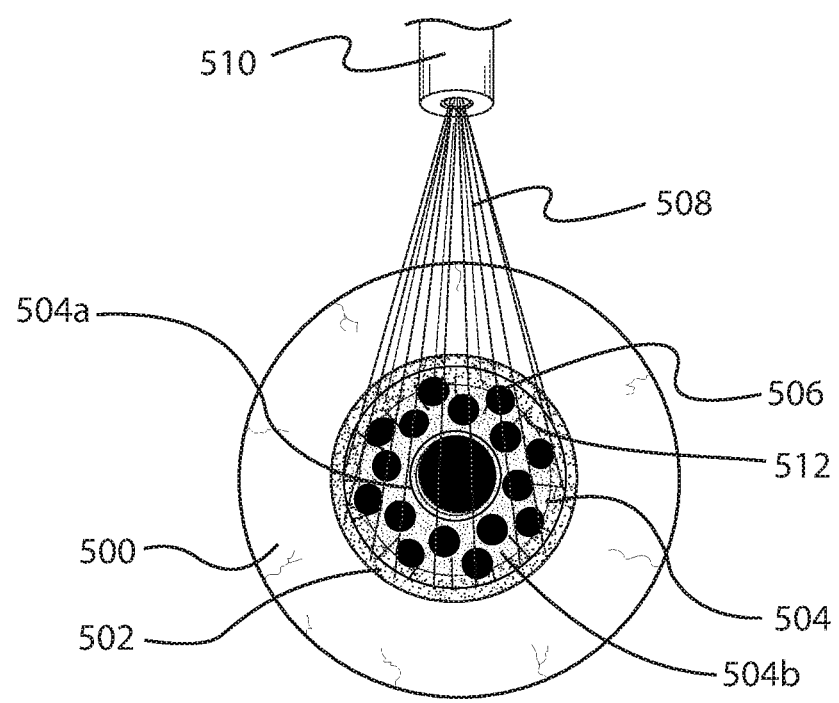
FIG. 28 is a front view of an eye where a keratoprosthesis lens has been implanted in the cornea of the eye and the cornea of the eye is being irradiated with ultraviolet radiation following the implantation, according to still another embodiment of the invention.
Figure 29A:
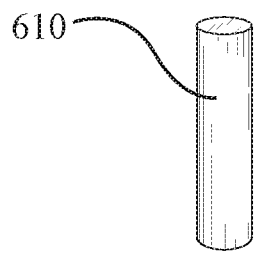
FIG. 29A illustrates a first exemplary shape for the drug delivery implant described herein, which is in the form of a rod-shaped implant.
Figure 29B:
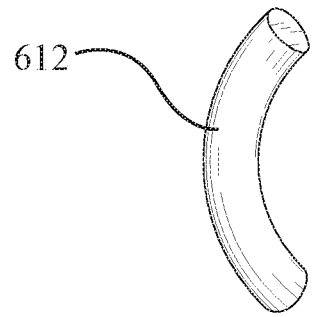
FIG. 29B illustrates a second exemplary shape for the drug delivery implant described herein, which is in the form of a curved implant.
Figure 29C:
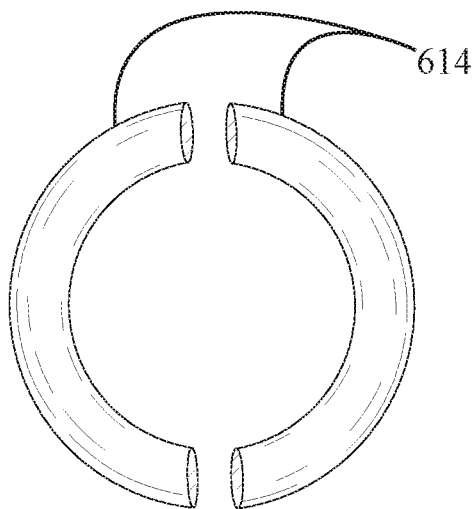
FIG. 29C illustrates a third exemplary shape for the drug delivery implant described herein, which is in the form of a two-part semi-circular implant.
Figure 29D:
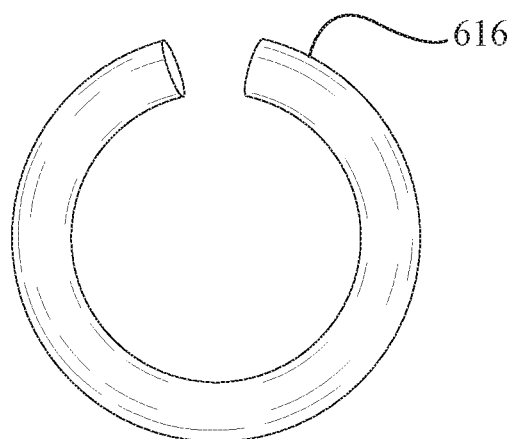
FIG. 29D illustrates a fourth exemplary shape for the drug delivery implant described herein, which is in the form of a one-part semi-circular implant.

A seventh illustrative embodiment is depicted in FIG. 28. In this illustrative embodiment, the repeated corneal transplant has led to a cloudy vascularized cornea 502 in which no corneal transplantation can be considered, the cornea 502 of the eye 500 is prepared for implantation of a keratoprosthesis lens 504 by removing the center part of the opaque cornea 502 by a trephine, thus creating a central opening in the cornea 502, and then a circular pocket in the remaining peripheral cornea is produced horizontally with a knife or laser so as to produce an anterior and a posterior flap around the central opening in the remaining part of the peripheral cornea, in which a prosthetic lens 504 with a central portion 504a and a peripheral flange 504b is implanted. As shown in FIG. 28, the peripheral flange 504b of the prosthetic lens 504 is provided with a plurality of apertures or holes 506 disposed therethrough for allowing the aqueous humour fluids of the eye to provide nutrients to the donor graft stroma. The riboflavin drops or nanoparticle suspension of riboflavin with or without CPP are applied to penetrate the front of the cornea 502 and the posterior corneal flap, followed a few anchoring 8-0 or 10-0 nylon sutures 512 to hold the prosthetic lens 504 in place, then followed by UV radiation 508 from a UV laser 510 of the entire cornea 502, except the lens 504 which is covered with a piece of tissue paper to prevent the light from getting inside the eye 500, thereby preventing vascular growth in the prosthesis 504 from the front and its side or fibrous tissue growth to the back side of the prosthesis 504 that could block the light reaching the retina (refer to FIG. 28).

Next, illustrative corneal crosslinking procedures with enhanced penetration of the crosslinking agent will be described. The process of crosslinking can be very time consuming in which the penetration of the cross-linker (e.g., riboflavin or any other cross-linker) is applied as drops to the corneal tissue for about 15-30 minutes to penetrate typically a depth of 150-200 microns of the anterior corneal stroma. Considering that corneal crosslinking often requires UV radiation for a period of 30 minutes, the operation takes at least between 30-60 minutes to perform. Also, riboflavin does not penetrate the cell membrane well. In the above-described embodiments, because the purpose is to reduce and eliminate the potential of corneal transplant rejection by the survived host corneal epithelial cells or the host stromal cells that produce cytokines against the transplanted cornea and vice versa, it is desirable to eliminate the cellular component of the host cornea or the transplanted cornea, or both, while maintaining the host corneal endothelial cells intact. Since the corneal endothelial cells, in general, are not affected if the riboflavin is applied over the corneal surface through which it penetrates inside the stroma, it is desirable to enhance cellular penetration of the cross-linker, and simultaneously penetration through the corneal stroma, which is made of collagen. Although the procedures described above can be used with standard riboflavin or any other crosslinking solution, a technique and formulation for expediting the cell penetration of riboflavin and the cross-linking of the cornea for corneal crosslinking and elsewhere in the body is very desirable.

In one or more embodiments, cell penetrating peptides are used that comprise the short peptide lysine or arginine, which are known as cell penetrating peptides (CPP) and activatable-cell penetrating peptides (ACPP). CPP and ACPP may be conjugated to dendrimers (ACPPDs) or other nanoparticles (e.g., riboflavin) or any other cross-linkers. The ACPP may be labeled with a polycationic CPP. ACPP and CPP may be naturally-occurring or artificially constructed protein segments (<30 amino acids) rich in arginine, lysine, cysteine, histidine, ornithine, etc.; preferably .alpha.-helices and about 17-amino acids. The ACPP and CPP may include a penetration accelerating peptide sequence (Pas) or an INF7 fusion peptide sequence. CPP and/or ACCP can be linked to cargoes either covalently or non-covalently. Nanoparticles may be delivered by cell-penetrating peptides comprised of nona-arginine and a penetration accelerating sequence. Also, nona-arginine may be used to facilitate the delivery of the riboflavin cross-linker into cells via multiple pathways. Exemplary, but not limiting ACPP and CPP may include transportan, penetratin, TAT, VP22, MAP, KALA, ppTG20, proline-rich peptides, MPG-derived peptides, Pep-1, nona-arginine, and the carboxy-terminal tail of TFPI-2, polyproline helices having cationic amino acids and/or cationic-functionalized amino acids within the helix). Nanoparticles may be coated or otherwise associated with organic or non-organic biodegradable compounds, aliphatic biodegradable polymers, as needed. The nanoparticles may comprise organic nanoparticles, non-organic nanoparticles, synthetic nanoparticles, or non-synthetic nanoparticles.

In one embodiment, riboflavin or other cross-linkers may be linked to, associated with, complexed or conjugated with nanoparticles using linking agents and methods including but not limited to the following: amino groups, carboxyl groups, S—S deprotected sulfhydril groups in biomolecules, carbodiimide conjugation, sulfosuccinimidylsuberyl linkage, synthetic tripyrrole-peptide linkage, NHS-esters and other esters, etc.

In one embodiment, the riboflavin or a cross-linker conjugated to dendrimers (ACPPDs) is applied to a cornea which has developed neovascular tissue, where the penetration of the riboflavin is very minimal in the endothelial cells or the neovascular tissue, so that subsequent UV radiation will not damage these cells or close the neovascular tissue of the cornea. Dendrimers and other types of nanoparticles do not need to have an antibody attached to them as long as they are applied topically for the crosslinking of the cornea. Although, nanoparticles do need to have a specific antibody attached to them if they are injected in the circulation of the patient for targeting a tumor.

In one embodiment, the cross-linker is conjugated with nanoparticles in the form of dendrimers or functionalized dendrimers conjugated with CPP or ACPP and administered locally, topically or injected in body cavity, to be absorbed by normal or abnormal tissue or tumor with their neovascular tissue and subsequently cross-linked by UV radiation or other laser wavelength absorbed by the cross-linker, not only damaging the neovascular tissue, but also the tumor cells, as an example. Also, the cross-linker conjugated with the dendrimers or functionalized dendrimers conjugated with CPP or ACPP may be applied to a surface lesion/tumor on the skin, mucosa or conjunctiva of the eye or inside a body cavity.

In one embodiment, the nanoparticles carrying riboflavin or another cross-linker are made of lactic acid, glycolic acid, or polycaprolactone and conjugated with a cell specific or organism specific antibody to attach to their cell membrane receptors.

In one embodiment, the nanoparticles are made of lactic acid, glycolic acid, polycaprolactone, or chitosan, or are in the form of dendrimers, and are conjugated with riboflavin, CPP and antibodies to target specific cells, such as tumors of neovascular cells, and to attach to the cell membrane receptors of these cells or to one or more organisms and to penetrate the cell walls of specific cells or organisms, thus carrying the photosensitizer or riboflavin inside the cell, while activated with a light or UV light, thereby crosslinking the cytoplasmic proteins and kill the cells or the organism.

In one embodiment, the photosensitizer is in the form of drops, and the drop solution or suspension of nanoparticles or dendrimers comprises between about 0.05% and about 1% riboflavin or a photosensitizer therein.

In one embodiment, the photosensitizer or riboflavin is in the form of drops or suspension of nanoparticles, and the drop solution comprises between about 0.0005% and about 5% riboflavin therein.

In one embodiment, riboflavin or the cross-linker solution may have ethylenediaminetetraacetic acid (EDTA) or Disodium Edetate Dihydrate 0.1 w/w %, Sodium Chloride 0.4 w/w %, Polycarbophil 0.95 w/w %, Octoxynol 40 (70% Solution), 2N NaOH (active dissolution @pH 7.9), q.s. to adjust pH to about 7.4-7.7 as desired, Mannitol 0.15 w/w %, Sodium thiosulfate 0.3 w/w %, Water q.s. to 100%. The riboflavin or the cross-linker solution may have an osmolarity of about 300 mOsm/L. The riboflavin or the cross-linker solution may also contain a cell penetrating agent (e.g., CPPs or ACPPs). In addition, the riboflavin or the cross-linker solution may be provided with or without a poloxamer and with or without dextran.

In one embodiment, the cross-linker is applied through a circular gel with the desired diameter of 1 millimeters (mm) to 15 millimeters (mm) or more to be placed on the surface of the cornea or other surfaces so that the cross-linker penetrates the desired area of the cornea selectively, etc.

In one embodiment, the gel has a thickness of 0.01 mm to 3 mm or more.

In one embodiment, the diameter of the gel is 5-10 mm.

In one embodiment, the gel is circular with an opening of 1-8 mm.

In one embodiment, the gel is made of an organic or synthetic material.

In one embodiment, the gel is made from cellulose derivatives.

In one embodiment, the gel is soaked with the photosensitizer, such as riboflavin or another chemical, at a desired concentration that can diffuse from it inside the tissue within the desired time.

In one embodiment, the circular gel fits on the surface of the cornea or another desired surface and has strategically made holes to selectively release the photosensitizer in that area, so that during the crosslinking, only specific areas are selectively cross-linked, while the other areas are left alone to have specific effect either in the refractive power, elasticity on the cornea or for specific selective implantation of an implant.

In one embodiment, the cross-linker or riboflavin/CPP are conjugated with functionalized nanoparticles, such as acrylic or acrylic derivatives or crystalline silicon or other organic transparent nanoparticles, to enhance cell penetration and penetration of the nanoparticles through the corneal stroma to kill the stromal cells and entrap the acrylic or crystalline silicon nanoparticle in the cross-linked stromal collagen and inside the cells after irradiation with UV radiation applied externally of through a fiber optic and crosslinking their cytoplasmic proteins and the collagen. Additionally, the corneal stroma and nanoparticles's index of refraction can be changed in the same session or later, using a femtosecond or multi-photon laser and a Shack-Hartmann unit to achieve a perfect refractive power for the cornea.

In one embodiment, a corneal inlay is soaked in a solution having a cross-linker or riboflavin/CPP are conjugated with coated nanoparticles, such as acrylic or acrylic derivatives or crystalline silicon nanostructure or organic transparent nanoparticles, to enhance cell penetration and penetration of the nanoparticles through the corneal stroma to kill the stromal cells and entrap the acrylic or crystalline silicon nanoparticle in the cross-linked stromal collagen and inside the cells after irradiation with UV radiation applied externally before implanting inside a corneal pocket or after implantation inside the stromal pocket using a fiber optic and crosslinking their cytoplasmic proteins where the corneal stroma and subsequently the refractive index of the inlay and the cornea with the nanoparticles can be changed using a femtosecond or multi-photon laser and a Shack-Hartmann unit to achieve a perfect refractive power for the cornea or modifying it for astigmatic, presbyopic, myopia, or hyperopia correction.

In one embodiment, the corneal inlay is prepared from a 3-D stromal tissue culture or an eye bank eye cornea where the inlay is soaked in a solution having a cross-linker or riboflavin/CPP are conjugated with PEGylated nanoparticles, such as acrylic or acrylic derivatives or crystalline silicon nanostructure or organic transparent, organic nanoparticles to enhance cell penetration and penetration of the nanoparticles through the corneal stroma to kill the stromal cells and entrap the acrylic nanoparticle or crystalline silicon in the cross-linked stromal collagen and inside the cells after irradiation with UV radiation applied externally before implanting inside a corneal pocket or after implantation inside the stromal pocket using a fiber optic and crosslinking their cytoplasmic proteins where the corneal stroma and subsequently the refractive index of the inlay or the cornea with the nanoparticles can be changed using a femtosecond or multi-photon laser and a Shack-Hartmann unit to achieve a perfect refractive power for the cornea.

In one embodiment, the cross-linker or riboflavin/CPP are conjugated with antibody coated nanoparticles or dendrimers, to reach specific cells targeted to kill after irradiation with UV radiation applied externally of through a fiber optic and crosslinking their cytoplasmic proteins, etc.

In one embodiment, the targeted cells are tumor cells.

In one embodiment, the tumor cells are located on the skin or mucosa.

In one embodiment, the riboflavin/CPP conjugated with antibody coated nanoparticles are injected inside the body cavity where the nanoparticles are attached to the tumor cells, then treated with UV radiation brought in using a fiber optic crosslinking their cytoplasmic proteins, etc.

In one embodiment, the riboflavin/CPP conjugated with antibody coated nanoparticles are administered intravenously to reach an internally located tumor and to attach to their cell membranes and kill them after locally administered UV radiation.

In one embodiment, the tumor is in the mouth, nose, throat, eye, conjunctiva, or lid of the eye, or lung and can be reached with a UV laser with a fine fiber optic to irradiate the tumor and kill them by crosslinking their cytoplasmic proteins, etc.

In one embodiment, the lesion is an infected ulcer of the cornea, skin or mucosa, nasal, throat, etc. that can be treated by topical application of the riboflavin/CPP or ACPP conjugated with antibody coated nanoparticles to kill the bacteria, viruses, fungi, protozoal infections treated with UV radiation applied through a fiber optic and crosslinking their cytoplasmic proteins, etc.

In one embodiment, the lesion is an infected ulcer of the cornea, skin or mucosa, nasal, throat, etc. that can be treated by topical application of the riboflavin/CPP or ACPP conjugated with antibody coated nanoparticles or dendrimers to kill the bacteria, viruses, fungi, protozoal infections treated with UV radiation applied through a fiber optic and crosslinking their cytoplasmic proteins, etc.

In one embodiment, the ulcer is an infected corneal ulcer treated by topical application of the riboflavin/CPP or ACPP conjugated with antibody coated nanoparticles or dendrimers to kill the bacteria with UV radiation applied through a fiber optic or an external UV light and crosslinking their cytoplasmic proteins, etc. as described before.

In one embodiment, the ulcer is an infected skin or mucosal ulcer treated by topical application of the riboflavin/CPP or ACPP conjugated with PEGylated nanoparticles/dendrimers to kill the bacteria, with UV radiation applied through a fiber optic or an external UV light by crosslinking their cytoplasmic proteins, etc., as described before.

In one embodiment, the keratoprosthesis 504 described above is coated with biocompatible nanoparticles, such as gold or silica, or a combination thereof, etc. in a manner that does not cover the central optical lens to prevent rejection.

In one embodiment, the riboflavin nanoparticle/dendrimer and CPP is used as a surface coating for any intracorneal implantation followed with UV radiation to kill the cells surrounding it by crosslinking their cytoplasmic proteins etc.

In one embodiment, the riboflavin nanoparticle or dendrimers and CPP is administered after extracapsular lens removal followed by administration of CPP/cross-linker conjugated with polyethylene glycol (PEG) coated nanoparticles in the capsular bag, then followed by lens implantation where the CPP enhances the penetration of the riboflavin into the lens epithelial cells and kills them by crosslinking their cytoplasmic proteins etc., thereby preventing capsular opacification.

In one embodiment, a glaucoma stent surface is coated with biocompatible nanoparticles, such as gold or silica, or a combination thereof, etc. to prevent rejection of the stent, then coated with CPP/riboflavin nanoparticles or dendrimers prior to the implantation of the glaucoma stent and then irradiated with UV radiation after the implantation to kill the cells by crosslinking their cytoplasmic proteins, etc. around the stent and prevent ingrowth of the cells blocking the stent and prevent ingrowth of the cells blocking the stent using a fiber optic.

In one embodiment, a cardiac/vascular stent is coated with biocompatible nanoparticles, such as gold or silica, or a combination thereof, etc. to prevent rejection, then coated with CPP/riboflavin nanoparticles or dendrimers prior to the implantation of the vascular stent and irradiated with UV radiation after the implantation to kill the cells by crosslinking their cytoplasmic proteins, etc. around the stent and preventing ingrowth of the cells blocking the stent using a fiber optic.

It is readily apparent that the aforedescribed corneal transplant procedures and inlay implantation procedures offer numerous advantages. First, the implementation of the aforedescribed corneal transplant procedures reduces the likelihood that the implanted cornea will be rejected by the patient. Secondly, the aforedescribed corneal transplant procedures enable the clarity of the transplanted cornea to be preserved. Finally, the aforedescribed corneal transplant procedures reduce the likelihood that the transplanted cornea will be invaded by migrating cells, such as migrating cells that might initiate an immune response such as macrophage, lymphocytes or leucocytes or vascular endothelial cells. These types of migrating cells are discouraged by the cross-linked corneal collagen which does not provide an easily accessible tissue to invade. In addition, the use of abovedescribed tissue adhesives reduces the surgical procedure significantly. Moreover, the aforedescribed corneal lenslet implantation procedures modify the cornea so as to better correct ametropic conditions. Furthermore, the corneal lenslet implantation procedures described above prevent the lens implant from moving around inside the cornea once implanted, thereby ensuring that the lens implant remains centered about the visual axis of the eye. In addition, the aforedescribed inlay implantation procedures prevent an immune response to the corneal inlay and to prevent a rejection of the corneal inlay by the patient.

Illustrative embodiments of a drug delivery implant and methods using the same will now be described hereinafter. In accordance with the various embodiments described herein, in order to provide the medication to the anterior and posterior part of the eye with a slow release drug system, it is required to create an immune privileged space inside the cornea to keep the cellular response away and prevent production of cytokine by them, and position the device outside the central visual axis so that the device would not interfere with the patient's vision.

In the embodiments described herein, the device is placed in the far corneal periphery so that it will not affect the vision or visual field of the patient, and so that it has created a so-called artificial "immune-privilege" which does not generate an immune response from the body while fluid, soluble medications or nano-particulates and micro-particulates can travel through it. See, for example, FIGS. 38A-45B.

Because of the location of the implant inside the cornea, the released medication bypasses the epithelial barrier of the cornea, while providing medication in a slow manner by diffusion to the anterior part of the cornea, to the sclera, to the conjunctival tissue, and to the posterior segment of the eye including the retina, choroid, and the optic nerve head. This technique can provide similar immune-privileged spaces in other part of the body so that devices implanted there are not encapsulated.

Figure 37:
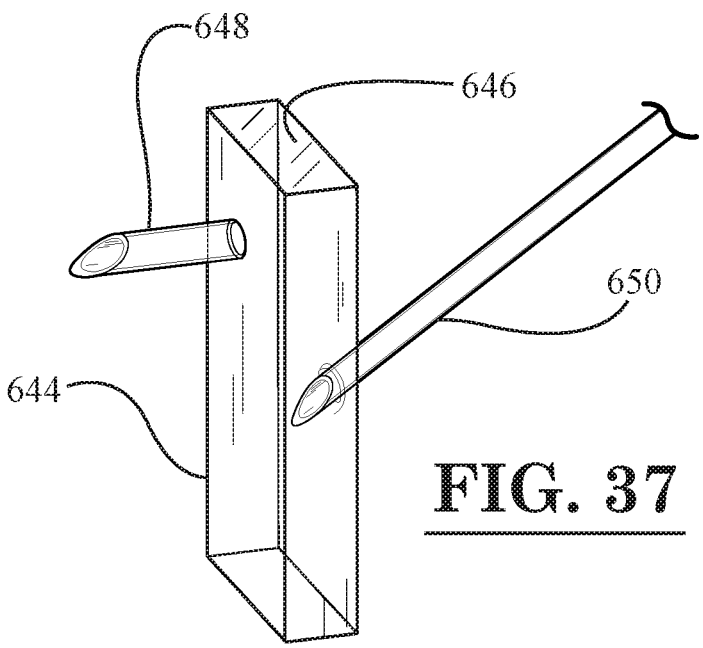
FIG. 37 illustrates yet another exemplary form of the drug delivery implant described herein, wherein the tubular implant comprises a needle for tissue penetration and the tubular implant is capable of being penetrating by a needle for taking liquid biopsies.

The drug delivery system of the embodiments described herein may be constructed so that it can have direct access to the anterior chamber, if needed, for both obtaining repeatedly a fluid biopsy from the eye or deliver medication(s) directly inside the eye in a fast or slow release manner, or for reducing the intraocular pressure of the eye by creating a minor flow through a porous implanted stent or tube through the corneal limbus without inducing a fibrous encapsulation of the stent. The stent can ameliorate also corneal dryness caused by dry eye syndrome. The stent can also be equipped with a pressure sensor indicating directly the intraocular pressure and communicating it with a radiofrequency device to outside the eye to a receiver or a processor. As one example, as shown in FIG. 37, the implant 644 may comprise a closed end 646 and a needle 648 for tissue penetration so that the implant 644 is capable of being used for taking liquid biopsies. In addition, stem cells or other cells can reside in, for example, a tubular implant, while having access to the oxygen and nutrients through the artificial barrier in an appropriately prepared corneal pocket. However the porous tubular implant permits these cells to migrate elsewhere in the eye or remain in place without being attacked by body's cellular response. Because the cellular body immune response is dependent on the production of the cells close to the implant or a foreign body to be taken up by the dendritic cells of the body at that location by creating a cell free space around the implant made of transparent amorphous cross-linked collagen. The invention of the embodiments described herein has eliminated the incentive for a Major Histocompatibility Complex (MHC) to occur. Because these MHC are present on the cell surface of the body cells to be activated in the production of an immune response. The release of theses cytokines activates the cellular immune system of the body to either eliminate the threat or isolate the device from the body completely by fibrocytes, thereby building a dense membrane (i.e., scar) around the implant. However, the cross-linked collagen permits the diffusion of water and small molecules permitting the needed growth factors from the incorporated stem cells placed inside the tubular implant needed for survival and the health of the cornea, retina etc.

Though this mechanism is very effective and useful, it affects the function of an implant that usually either releases a needed medication or measures or controls the release of a medication (e.g., measuring the blood glucose level and/or releasing insulin according to the glucose level found in the blood, etc.).

In order to isolate an implant in the body while preventing the immune cell to gain access to the device or build a membranous scar tissue around it, a method has been developed to isolate the implant in the body by killing all the cells adjacent to an implant, while maintaining a fluid-filled area around the implant or creating a barrier out of the surrounding tissue containing collagen and cross-linking the tissue in vivo. This barrier protects the implant from the antigen presenting dendritic cells in the tissue, while permitting the soluble medication or nano-sized particulate material to pass through the barrier so as to treat a pathological process in the body. One can also monitor the level of the analytes in the tissue fluid (e.g., aqueous fluid levels of glucose), which is a representative of the blood glucose level in the blood, from which it is originated. Aqueous level of most if not analytes found in the blood and could be used effectively to provide information on the health or disease processes affecting the eye or the body as a whole.

In the embodiments herein, implantation of a drug delivery device is described for the release or monitoring and controlling of a disease process in the eye, while crosslinking the tissue around the implant or implants (if more than one implant is provided). In any of the embodiments described herein, a plurality of drug delivery implants may be used (e.g., for delivering different medications), rather than a single drug delivery implant.

The technology described herein may be applied for any other device implantation in the body regardless of the location in the body. One of the benefits of the technology is that, if the device needs to be replaced, it can be done easily without dealing with the scar tissue formation that otherwise forms and makes the removal or replacement of the implant very complex because the tissue adhesions that usually forms between the tissue and the device.

One can use this concept described herein for diagnosis or therapy in diseases affecting the cornea, a metabolic disorder, genetic disorder, glaucoma, an infection affecting the eye or another portion of the body, a disease or disorder affecting the front or the back part of the eye or the conjunctiva or lens, an aging process, such as dry eye formation, retinal diseases including infective processes, genetic diseases requiring gene therapy (e.g., retinitis pigmentosa, etc. or metabolic disorders such as diabetes, etc.).

In one embodiment, if the media is clear, a two dimensional intrastromal corneal incision is created that is subsequently converted into a pocket in the corneal stroma using a femtosecond laser or a mechanical cutting system. The femtosecond laser passes through the clear media of the cornea. When the laser beam is focused inside the cornea, one can produce a two-dimensional cut or a three-dimensional cut around a thin part of the tissue that is removed to desired space, shape, depth, and location.

In another embodiment, in opaque elastic tissue (e.g., skin), one can use a knife or a syringe needle ending in a sharp cutting tip to cut a pocket in the tissue. If needed, the incision simultaneously involves removal of a three-dimensional tissue surrounding the surgical pocket to create some additional space for the implant using a similar cutting instrument, in the skin or soft tissue. In general, a cut creates a flexible three-dimensional space that can be filled with an implant. The implant is placed inside the needle and can be expelled from the needle by the syringe into the space created by knife.

In one or more embodiments, an injectable anesthetic (e.g., lidocaine or Bupivacaine) in a desired non-toxic preparation or concentration of 0.1-2% or more in a physiologic solution with, but preferably without, a preservatives, is injected in the corneal pocket to anesthetize the cornea postoperatively for a period up to 8-12 hours (e.g., if a PRK procedure is contemplated or after a corneal inlay implantation to prevent pain sensation completely in the postoperative period). This eliminates subjecting the entire corneal epithelium or the conjunctival epithelial cells to the damaging effect of topical anesthesia, which delays corneal re-epithelialization or conjunctival epithelial cells. Generally, the topical preservatives present in the topical anesthesia damages the cells that are bathed in them, and at times affects the regeneration of these cells (i.e., corneal epithelial or conjunctival cells) if applied frequently. Also, it may produce addiction to the topical anesthesia for eliminating the pain sensation caused by the loss of the corneal epithelial cells, whereas the injectable anesthetic does not damage the epithelial cells, including the nerve cells or their axons, except for blocking temporarily the neuronal transmission.

In one or more embodiments, the collagen cross-linker is mixed with the intracorneal locally injectable anesthetic, and injected simultaneously or sequentially in the corneal pocket.

In one or more embodiments, the pocket is filled with a biocompatible implant or implants (if more than one implant is provided) made of organic or non-organic material, or a mixture of it, and the implant is used for drug delivery. The implant may further be coated with a biocompatible material, such as collagen, elastin, polyethylene glycol, biotin and streptavidin, etc., as known in the art, or a composition thereof, to make the implant more biocompatible. The implant and/or the coating can be cross-linked with a cross-linker with the desired thickness and shape before or after implantation.

In one or more embodiments, the diameter of the corneal pocket can be 0.1 to 4 millimeters (mm), as needed. Only flat implants need a larger space with more than 0.2 mm. As shown in FIG. 38A-45B, the pocket can be circular, semi-circular, C-shaped, doughnut-shaped, rectangular, or any other shape.

In one or more embodiments, the implant or implants (if more than one implant is provided) can be located at a desired distance from the Bowman's membrane or from the corneal periphery, that is located away from the center of the visual axis (i.e., the implant may be off-centered, or ring-shaped in the peripheral cornea). See, for example, FIGS. 38A-45B.

In one or more embodiments, the implant or implants (if more than one implant is provided) is made to the desired shape, and size in diameter and length that fits with ease inside the corneal pocket without exerting pressure on the corneal tissue (i.e. without bulging it).

In one or more embodiments, a photosensitizer or cross-linker, such as riboflavin, is injected at the desired concentration in a biocompatible fluid or a viscous fluid prior to the implantation of the implant. However, it can be also administered simultaneously with the implant in the corneal pocket sufficiently to cover the internal wall of the pocket for a desired duration so that it penetrates at least 20 micron or wider, taking 5-30 seconds after injection prior to the cross-linking of the cornea, which prevents cell proliferation, encapsulation, or rejection of the implant while preserving an acellular barrier.

In one or more embodiments, ultraviolet (UV) radiation at the desired power (e.g., 1 to 4 mW/mm$^2$) and duration of 1-15 minutes, as needed, depending on the concentration of the photosensitizer or other radiation if another cross-linker is used (e.g., visible or infrared (IR) or another wave length) is applied externally to activate the photosensitizer in the corneal pocket, and to cross-link the collagen of the corneal stroma surrounding the corneal pocket, thereby killing only the cells located within the cross-linked cornea while preventing encapsulation of the drug implant while providing a physical stability to the cornea and preventing the wall of the pocket from adhering together or to the implant. This permits the implant to be replaced, if needed, with another implant with ease.

In one or more embodiments, the implant is coated with an organic material, such as collagen, dipped in a photosensitizer, or the implant can be coated with nanoparticles of the photosensitizer and implanted in the corneal pocket and ultraviolet (UV) radiation is applied with the desired power and duration using a painting technique using a small diameter fiber optic or other radiation with another wave length is applied if another cross-linker is used, externally or internally inside the pocket via a fiber optic to activate the photosensitizer in the corneal pocket and to cross-link the collagen of the corneal stroma surrounding the corneal pocket, thereby killing all cells located within the cross-linked cornea and cross-link the implant simultaneously. The corneal cross-linking prevents implant encapsulation with fibrous tissue, but provides a physical stability to the cornea without gluing the wall of the pocket together or to the implant.

In one or more embodiments, an injection of a small amount of hyaluronic acid in the pocket simplifies insertion of the drug implant in the corneal pocket.

In one or more embodiments, the drug implant has a tube-like structure with a size of 0.01 to 3 micron diameter holes in its wall, or having one micron or larger-sized holes for diffusion of fluid across it.

In one or more embodiments, the implant can be silicone, acrylic, methacrylate, hydroxyethyl methacrylate (HEMA), cross-linked organic or any other biocompatible transparent or non-transparent material, metallic or non-metallic, or a mixture thereof or coating other polymers, such as collagen or elastin with the desired thickness of 2 microns or more, as needed.

In one or more embodiments, the implant is made of various drug delivery polymers, such as polylactic acid or polyglycolic acid, or a combination thereof or polycaprolactone, or chitosan or other organic materials that can deliver the medication at a certain concentrations and dissolve within time ranging from 3-12 months or more.

In one or more embodiments, the biodegradable or non-biodegradable implant can be replaced with another one as before or a non-biodegradable material, but having biocompatible material or coating where the drug release occurs either through the small holes in the body of the implant at a certain rates depending on the size of the holes, or from one or both ends of the implant for drug delivery, as needed.

In one or more embodiments, the implant is a porous biodegradable polymer.

In one or more embodiments, the material inside the tubular implant is liquid, nanoparticles, suspension, powder, porous polymeric drug, etc.

In one or more embodiments, the implant is made using 3-D printing technology to the desired shape, size and/or coated with more biocompatible polymer(s) and cross-linked prior to the implantation, or it is implanted in a cross-linked pocket.

In one or more embodiments, the cross-linked corneal implant can be loaded with one or multiple medications needed for a short biocompatible drug delivery, or prophylactically to prevent an infection, or other used therapeutically medications to treat a disease process (e.g., inflammation, intraocular pressure (IOP), neovascularization, infection, or a cytokine, etc.).

In one or more embodiments, an organic cross-linked material can be used as above for a short term drug delivery of 1 to 4 weeks.

In one or more embodiments, an organic cross-linked material can be used as above for a short term drug delivery of 5 to 50 weeks or longer.

Figure 34:
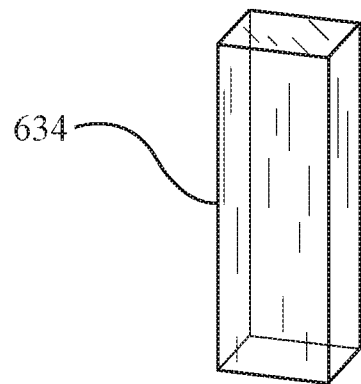
FIG. 34 illustrates still another exemplary form of the drug delivery implant described herein, wherein the implant is in the form of a rectangular flat tube.
Figure 38A:
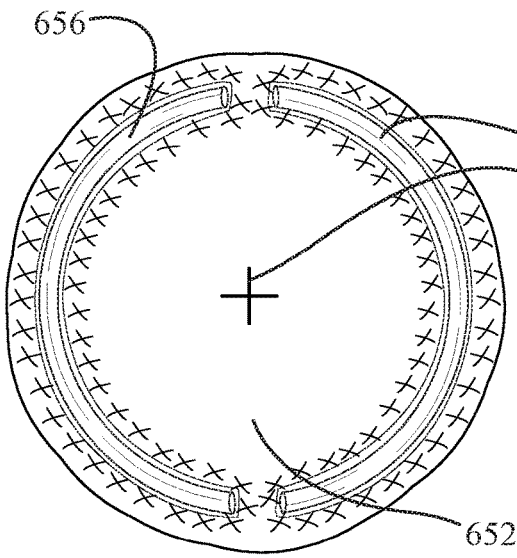
FIG. 38A is a front view of a cornea of an eye illustrating a two-part semi-circular drug delivery implant disposed in a cross-linked pocket in the peripheral portion of the cornea that is spaced apart from the central visual axis of the eye so as not to obstruct the central portion of the eye.
Figure 38B:
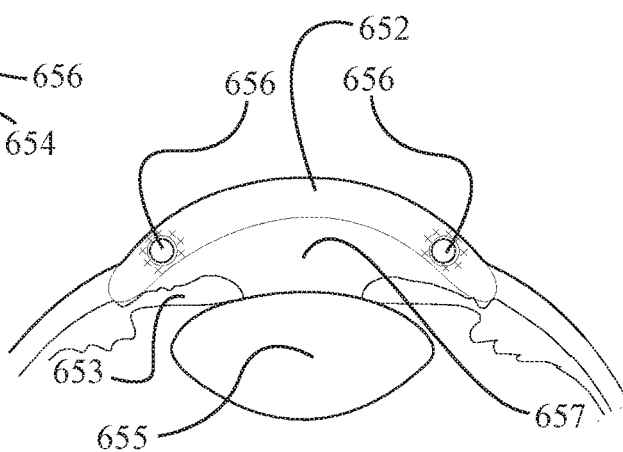
FIG. 38B is a partial side cross-sectional view of the eye of FIG. 38A illustrating the two-part semi-circular drug delivery implant disposed in the cross-linked pocket in the peripheral portion of the cornea.
Figure 39A:
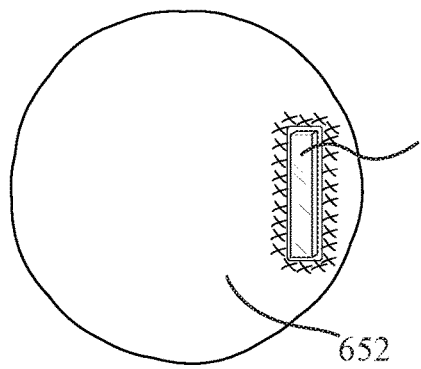
FIG. 39A is a front view of a cornea of an eye illustrating a generally linear drug delivery implant disposed in a cross-linked pocket in the peripheral portion of the cornea that is spaced apart from the central visual axis of the eye so as not to obstruct the central portion of the eye.
Figure 39B:
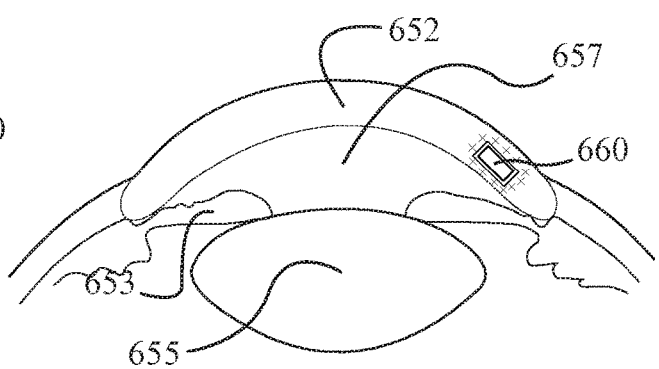
FIG. 39B is a partial side cross-sectional view of the eye of FIG. 39A illustrating the generally linear drug delivery implant disposed in the cross-linked pocket in the peripheral portion of the cornea.

In one or more embodiments, the implant is a C-shaped flexible or semi-flexible structure, and can be implanted in the prepared corneal pocket according to the size or the shape of the implant (e.g., centered around the visual axis having a string shape, rod-like shape, or flat shape), while removing a small 3-D tissue from the stroma for the pocket formation to provide space for the implant for drug delivery to the cornea or the anterior chamber, trabecular meshwork, conjunctiva, or diffusing toward the posterior segment, such as the retina, choroid or the optic nerve of the eye. As shown in FIGS. 29A-29D, the drug delivery implant may be rod-shaped 610, C-shaped 612, two-part semi-circular 614, or one-part semi-circular 616. Also, as illustrated in FIG. 34, the implant may also be in the form of a rectangular flat tube 634. In FIGS. 38A and 38B, a two-part semi-circular drug delivery implant 656 disposed in a cross-linked pocket in the peripheral portion of the cornea 652 that is spaced apart from the central visual axis 654 of the eye so as not to obstruct the central portion of the eye. As shown in FIG. 38B, the two-part semi-circular drug delivery implant 656 is disposed adjacent to the anterior chamber 657 of the eye, and anteriorly with respect to the iris 653 and lens 655 of the eye. In FIGS. 39A and 39B, a generally linear drug delivery implant 660 is disposed in a cross-linked pocket in the peripheral portion of the cornea 652.

Figure 44A:
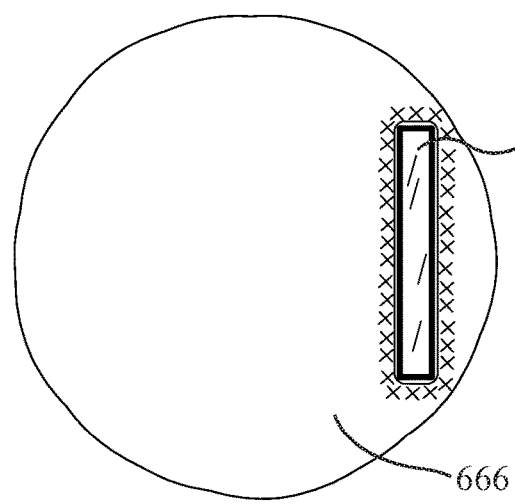
FIG. 44A is a front view of a cornea of an eye illustrating a generally linear drug delivery implant disposed in a cross-linked pocket in the peripheral portion of the cornea.
Figure 44B:
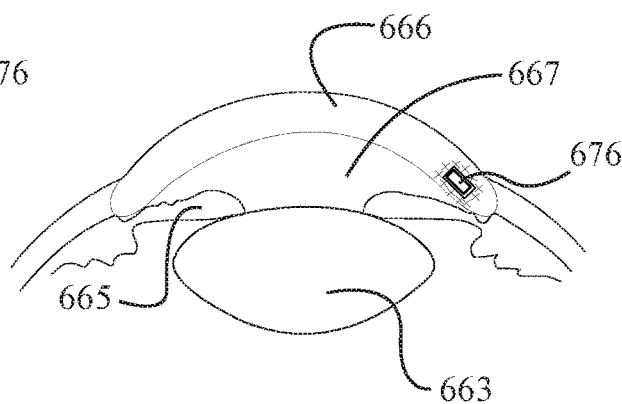
FIG. 44B is a partial side cross-sectional view of the eye of FIG. 44A illustrating the generally linear drug delivery implant disposed in the cross-linked pocket in the peripheral portion of the cornea.

Turning to FIGS. 41A and 41B, it can be seen that an eye generally includes a lens 663, an iris 665, cornea 666, an anterior chamber 667, a pupil 668, and a limbus 670. In FIGS. 42A and 42B, a one-part semi-circular drug delivery implant 672 is shown disposed in a cross-linked pocket in the peripheral portion of the cornea 666. In FIGS. 43A and 43B, a doughnut-shaped or ring-shaped drug delivery implant 674 is shown disposed in a cross-linked pocket in the peripheral portion of the cornea 666. In FIGS. 44A and 44B, a generally linear drug delivery implant 676 is shown disposed in a cross-linked pocket in the peripheral portion of the cornea 666.

In one or more embodiments, the implant is inserted in the corneal pocket through a small external incision made into the corneal pocket.

In one or more embodiments, the pocket itself can be filled with biodegradable nanoparticles for drug delivery to the entire ocular structures from the cornea to the optic nerve, and all tissues in between. The medication(s) can be anti-inflammatory, anti-infective, immune-suppressants, AntiVEGFs, biologics, Anti-PDGF, Anti IL-6, Rho kinase inhibitors, nerve growth factors, anti-glaucoma medications, gene(s) delivery in conjugation with viral or non-viral nanoparticles, such as nanoparticles, quantum dots, biodendrimers, etc. coated with polyethylene glycol (PEG) or cell penetrating agents along with an antibody to the specific tissue. This permits the genes or medications to be delivered after their migration out of the implant and the corneal pocket and to attach to the targeted cells in the cornea, conjunctiva, trabecular meshwork, retinal ganglion cells or photoreceptors, retinal and optic glial or nerve cells or their axons etc.

In one or more embodiments, the one or more medications in the drug implant may be anti-inflammatory agents, such as steroids, Dexamethasone, NSAIDS, Anti IL-17, Anti IL-6 and other Anti-ILs or antibiotics, fluoroquinolones, macrolides, cephalosporin A, vancomycin, aminoglycosides, penicillin and its derivatives or combination of antibiotics, etc., anti-virals, ganciclovir, valcyclovir, etc., anti-fungals, amphotericine B, etc., Anti-VEGFs, Avastin, lucentis, Aflilbercept, Anti-IL-6, anti-parasitic, etc., or other anti-inflammatory agents, such as NSAIDs after any corneal surgery and act therapeutically to various diseases affecting the conjunctiva (e.g., dry eye), immune-suppressants, such as cyclosporine A, Mycophenolic acid, anti-proliferative agents, anti-metabolite agents, in uveitis, choroiditis or other medications, such as anti-glaucoma medication or combination of medications, gene delivery, DNA, RNA, siRNA etc. along with viral or non-viral delivery vehicles and CRISPR-cas9 mediated homology-independent targeted integration (HITI) or homology directed repair (HDR) to modify the genetic components of various diseases of the eye.

In one or more embodiments, repeated crosslinking of the pocket can be performed as needed to prevent new cellular ingrowth and adhesion around the implant from the corneal tissue so that the implant's barrier is maintained, and the implant can be removed or replaced as needed (e.g., if the eye needs another or a combined medication to regulate disease process, such age related macular degeneration, glaucoma, uveitis, choroiditis or an infectious process of any origin).

In one or more embodiments, the peripheral cross-linked pocket is used to insert or inject medications needed to treat a corneal disease or glaucoma or a disease of the posterior segment. The medication can be in a form of nanoparticles, microspheres, lipid coating or PEG, streptavidin, biotin coating, etc., micelles, liposomes, thermosensitive chitosans, etc.

In one or more embodiments, one can inject or implant in the peripheral corneal pocket large-sized flexible, semi-solid or porous or solid rod, flat or tube or any shape and size polymeric material that can be absorbed with time and the medication is released slowly to the cornea or the anterior chamber of the eye or diffuses to the back of the choroid or retina and optic nerve.

In one or more embodiments, the diameter of these rod or flat-shaped shape implants can vary between 10 microns to 1 millimeter (mm) in diameter or larger with a length of 1 to 50 mm or longer.

Figure 36:
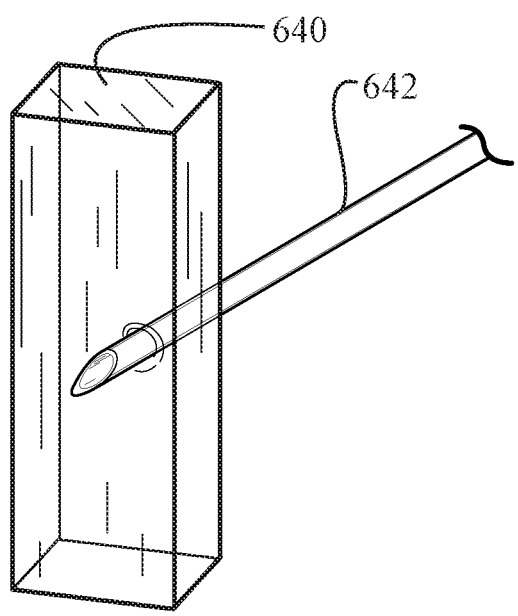
FIG. 36 illustrates still another exemplary form of the drug delivery implant described herein, wherein the implant is in the form of a rectangular tube that is refillable by injection.

In one or more embodiments, the porous tube can be made of semi-permeable non-biodegradable material that permits only the diffusion of the fluid/medication, etc. in and out of the tube, implanted in the peripheral cross-linked pocket. In these one or more embodiments, the tube can be refilled with medication as needed. For example, as shown in FIG. 36, the implant 640 in the form of a rectangular tube is refillable by injection with a needle 642.

In one or more embodiments, the drug implant tube contains stem cells, embryonic stem cells, ciliary hormone producing cells, or other hormone or factors producing stem cells, neuronal or glial stem cells, Mesnchymal stem cells, trabecular meshwork stem cells, limbal stem cells, modified skin stem cells, etc. in a biocompatible fluid that permits nutrition to reach the cells injected in the tube where the cells are immortalized to produce one or the other medication, growth factors, such as ciliary neurotrophic growth factor, RPE growth factor, nerve growth factors, anti-VEGFs, or other medications needed.

In one or more embodiments, the non-biodegradable tube with pores for drug and cell delivery is implanted in a cross-linked pocket with an implant in any part of the body for medication and cell delivery for various medications and functions.

Figure 32:
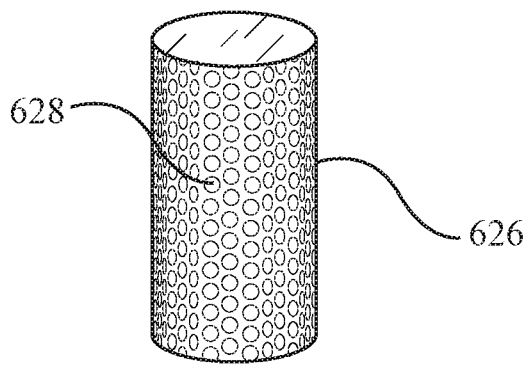
FIG. 32 illustrates another exemplary form of the drug delivery implant described herein, wherein the implant is tubular-shaped with holes formed in the side thereof.
Figure 33:
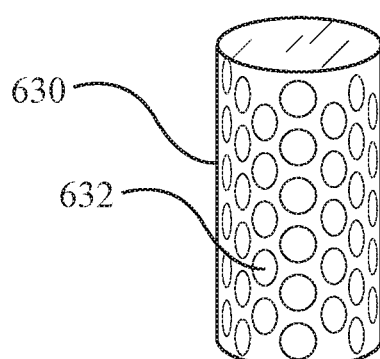
FIG. 33 illustrates yet another exemplary form of the drug delivery implant that is similar to that which is depicted in FIG. 32, except that the tubular-shaped implant of FIG. 33 has larger-sized holes formed in the side thereof.

In one or more embodiments, the implant is coated with biocompatible polymer(s) that is used for delivery of stem cells with medication in a corneal pocket. The implant has larger diameter holes of 5 microns and more in its wall permitting the cells to escape from the tubular implant into any tissue (e.g., corneal pocket containing stem cells, embryonic stem cells, ciliary body factor producing stem cells, neuronal or glial stem cells, Mesenchymal stem cells, trabecular meshwork stem cells, Limbal stem cells, modified skin stem cells, etc. in a biocompatible fluid) that permits nutrition to reach the cells injected in the tube where these cells can grow and pass through the holes of the implant and move toward a tissue. In FIG. 32, the tubular implant 626 has small holes 628 disposed in the circular peripheral side thereof, whereas the tubular implant 630 in FIG. 33 has large holes 632 disposed in the circular peripheral side thereof.

In one or more embodiments, the implant contains stem cells, embryonic stem cells, cilliary body hormone producing stem cells, neuronal or glial stem cells, Mesenchymal stem cells, trabecular meshwork stem cells, limbal stem cells, modified skin stem cells, etc. in a biocompatible fluid that permits nutrition to reach the cells injected in the tube along with Rho kinase inhibitors or Nerve growth factors to stimulate their regeneration and migration of theses cell and repair the pathology in the tissue.

In one or more embodiments, genetically modified cells are used to produce needed enzymes and medications. The combination of cross-linking of the cornea and killing the corneal cells and lack of vessels in the corneal makes it a suitable place for these cells in the tube implant to survive inside the tube without being attacked by the cellular body's response, thereby creating an immune privileged space for these cells to survive and produce medications needed locally or systemically (e.g. in many genetic diseases of the cornea such as Fuchs dystrophy, etc.).

In one or more embodiments, the pocket can be filled with a polymeric material that can become more semisolid, or becomes a gel, and contains medication for slow release of medication.

In one or more embodiments, the medication can be injected in the peripheral pocket along with corneal stem cells from the limbus or genetically modified skin stem cells, embryonic or pluripotential stem cells, or mesenchymal stem cells grown in the culture for implantation, in cases of cell loss of endothelium, or in genetically caused corneal opacification, such as macular dystrophy or trauma.

In one or more embodiments, the stem cells are mesenchymal stem cells injected in the corneal pocket along with ROCK inhibitors to replace or repair a cloudiness of the cornea.

In one or more embodiments, the stem cells are nerve cells to induce regeneration of the damaged corneal nerve (e.g., in diabetic patient) and after traumatic corneal injuries or after LASIK surgery.

In one or more embodiments, all tubular drug implants or devices are replaceable with ease.

In one or more embodiments, the tube can be refilled with medication to be used as slow release drug delivery that releases the drug in the cornea and anterior of the posterior segment of the eye.

In one or more embodiments, the tube is used for taking fluid samples from the eye.

In one or more embodiments, one creates an intrastromal corneal pocket in the peripheral cornea involving 2-4 mm 4-8 mm in width areas involving the cornea and the anterior sclera after bleaching out the peripheral conjunctival capillaries with a low dose of vasoconstrictive medication such as 0.5%-1% phenylephrine applied locally with a Q-tipped applicator using a femtosecond laser.

In one or more embodiments, a small knife can be used to create a pocket in the cornea or elsewhere under the skin etc. if needed.

In one or more embodiments, the pocket width is more toward the corneal side than the scleral side or vice versa. The circumferential extent of the pocket can be 1 degree to 360 degrees of the corneal periphery (see FIGS. 38A, 38B, 42A, 42B, 43A, and 43B).

In one or more embodiments, using a small incision to access the intrastromal incision, one uses a curved probe to separate the corneal adhesion for injection of a photosensitizer cross-linker, such as riboflavin, at the desired concentration of 0.5%-4% in a biocompatible fluid, such as a physiological saline solution, etc. or suspension of particulates in a volume of 0.01 milliliters (ml) to 1 milliliter (mm) as needed only for the extent of the corneal pocket to cover the internal walls of the pocket for a desired duration that the photosensitizer penetrates at least 20 microns and beyond the corneal pocket in the corneal stroma to isolate that localized area of the cornea from the rest so that it does not respond with cell migration into the surrounding implant and so that it avoids tissue bounding together or to the implant.

In one or more embodiments, 0.01 ml to 0.1 ml of 0.02-2% lidocaine or bupivacaine solution can be injected alone or along with the photosensitizer in the corneal pocket to anesthetize the cornea for the next 1-15 hours, thereby eliminating pain sensation or discomfort of the surgery, and dry eye after surgery.

In one or more embodiments, the width of the corneal pocket can be 1-3 mm as needed. The peripheral corneal pocket can be circular, semi-circular, C-shaped, doughnut-shaped, straight, curved, or any other shape.

In one or more embodiments, the cross-linked pocket can be located at a desired distance from the Bowman's membrane in the corneal periphery.

In one or more embodiments, the ultraviolet (UV) radiation or other appropriate wavelength of light at the desired power 0.5-50 mW/Cm2 and duration of 1-15 minutes, or other radiation with another wave length is applied externally in a stationary pattern or as a continuous painting/oscillatory technique with a focused small sized spot of 1-4 mm and a high energy to cover the width of the pocket, or on a painting oscillatory fashion entering the corneal pocket with a small diameter fiber optic and to activate the photosensitizer in the corneal pocket and crosslink the collagen of the corneal stroma surrounding the corneal pocket, and preventing the wall from adhering to itself or to a future implant, while providing a physical stability to the wall of the corneal pocket and preventing cell migration and rejection of an implant.

In one or more embodiments, ultraviolet (UV) radiation at the desired power in a stationary or focused light for a duration of 10 seconds to 15 minutes for the stationary radiation, or for a duration of 10 seconds to 20 minutes for the painting approach, depending on the power of the radiation and the length of the pocket used (or other radiation with another photosensitizer and wave length) is applied externally or via a fiber optic inserted inside the pocket to activate the photosensitizer and cross-link the collagen of the corneal stroma surrounding the corneal pocket while preventing cell migration, encapsulation, or rejection of the implant and protecting the anterior corneal stroma and the stem cells.

In one or more embodiments, the corneal pocket is three-dimensionally cut in order to remove a part of the stroma and create a space for the implant.

In one or more embodiments, the wall of the corneal pocket can absorb the photosensitizer from the implant after it is dipped in a photosensitizer solution or the implant is coated with nanoparticles of the cross-linker and placed in the corneal pocket to leak out, which is then followed by UV radiation at the desired power and duration or other radiation with another wave length applied externally or internally via a fiber optic to activate the photosensitizer in the corneal pocket and cross-link the collagen surrounding the implant. This technique provides a physical stability to the cornea preventing adhesion or gluing the implant to the surrounding tissue and preventing fibrous ingrowth or encapsulation or rejection of the implant, which can lead to implant rejection. This makes it possible to exchange the implant when needed without much trauma to the cornea surrounding the implant.

In one or more embodiments, the photosensitizer is conjugated to the surface of the implant having a polymeric coating, such as collagen, that releases the photosensitizer (e.g., riboflavin) from the implant once it is exposed to the water content of the tissue in the corneal pocket surrounding it. The riboflavin is released and stains the wall of the implant which is subsequently cross-linked with UV light. This prevents tissue adhesion between the implant and the corneal tissue and maintains a potential space between the corneal wall and the implant, thereby preventing activation of an immunologic response or neovascular tissue response by releasing from the tissue vascular endothelial cell factors (VEGF) in response to a foreign implant. The cross-linking process can be repeated as needed every 6 months to a year or more as needed. The cross-linking of the collagen protects the implant containing particulate medication(s), which releases the drug for a long time, and prevents the pocket from being invaded by the immune cellular elements and keeps the lumen of the tube shaped implant open.

In one or more embodiments, during the cross-linking, the corneal pocket remains pristine not allowing cell traffic or access to the pocket surrounded by the cross-linked amorphous collagen or other cross-linked tissues located in that area.

In one or more embodiments, the crosslinking can be repeated again in the postoperative period after implantation by injecting a cross-linker in the corneal pocket through a needle inside the wall of the pocket, which diffuses readily through the potential space around the implant and the wall of the pocket, and then is irradiated with UV light from the outside.

In one or more embodiments, the implant can be made of silicone, acrylic, methacrylate, HEMA, metallic or non-metallic, synthetic, organic, polymeric biodegradable, etc., coated with another or a biocompatible polymeric materials or a mixture thereof or coated with, for example, collagen or elastin, formed with a desired thickness of 2 microns to 100 microns, and conjugated with a cross-linker or the cross-linker is injected in the potential pocket space in the tissue and is cross-linked.

In one or more embodiments, the implant is made by the use of 3-D printing technology with the desired material, shape, size or thickness, transparent or non-transparent organic or non-organic or a mixture of them, a material such as collagen elastin, synthetic polymers can be coated again with riboflavin nanoparticles with one or more biocompatible polymer(s), and cross-linked with UV light prior to or preferably after implantation.

Figure 30:
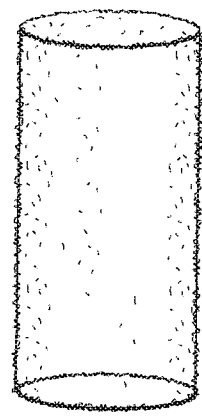
FIG. 30 illustrates an exemplary coated drug delivery implant, wherein the drug delivery implant is coated with a polymer and a photosensitizer.

In one or more embodiments, the implant is coated with a collagen polymer to a desired thickness or in combination with another polymer, such as polyvinyl alcohol, chitosan, polycaprolactone, etc., conjugated with riboflavin or another cross-linker and cross-linked before or after implantation in a preformed pocket with an appropriate wavelength of light or UV radiation to cross-link the polymeric coating inside the body allowing the cross-linker to be released in the tissue, and then cross-link the tissue surrounding the implant in order to, after implantation, release the incorporated medication from the implant slowly without inciting cellular attraction or encapsulation of the implant which inhibits a release of the medication(s) from the implant that is unpredictable. For example, as shown in FIG. 30, the implant 618 is coated with a polymer and/or a photosensitizer.

In one or more embodiments, the non-biodegradable flexible porous tube made of polymeric material or a non-organic compound in combination with cross-linked organic polymer coating is filled with microspheres, drug nanoparticles incorporated in a polymeric material, such as polylactic glycolic acid, chitosan, liposomes, polycaprolactone, or lipid-coated nanoparticles, etc. containing the medication so as to release the medication slowly from the tube implant.

In one or more embodiments, the implant can serve as a reservoir that releases the medications though the pores of 1 to 3 microns in diameter in its wall, and then can be refilled repeatedly by injecting in the tubular implant the medication through a 33-34 gauge needle through the cornea surrounding the tube.

In one or more embodiments, the implant releases immunosuppressive agents, such as cyclosporine, calcineurin inhibitors, mycophenolic acid, tacrolimus, siraliums, steroids, MPP inhibitors, NSAIDs, antimetabolytes, polycolonal antibodies, monocolonal antibodies, TNF inhibitors, Fingolimod, antibiotics, intraocular pressure (IOP) lowering agents, such as Rho kinase inhibitors, Fasudil, and other agents, pilocarpine, prostaglandin analogues, Brimonidine, etc., anti-virals, Anti-VEGFs, biologics, or neuroprotective releasing medication. The medications being released as needed at concentrations of nanograms or micrograms or mg/per hour depending on the polymeric material size of the holes, length of the polymer, etc.

In one or more embodiments, the implant can be positioned at any place in the body to control a function or release a medication without being encapsulated by the surrounding tissue, due to the cross-linking of the polymeric coating or the pocket being cross-linked prior to the implantation, while the medication can be an anti-VEGF, neuroprotective agents, such as nerve growth factors, Rho kinase inhibitor such as Fasudil, antibiotics, antiproliferative agents, anti-inflammatory agents, etc. at a non-toxic, beneficial concentration.

In one or more embodiments, the implant is made using 3-D printing technology to the desired shape, size or thickness from any material coated with collagen, elastin, or made of collagen, elastin, etc. or synthetic polymers which are further coated with more biocompatible polymer(s), such as acrylic, organic, etc., which are cross-linked prior to the implantation or coated with a cross-linker or the crosslinking nanoparticles are done subsequent to its release in the tissue prior to radiation with the UV light. In another embodiment, the implant is formed from glass using 3-D printing technology (i.e., the implant is 3-D printed glass).

In one or more embodiments, the implant is implanted in another part of the eye, such as under the conjunctiva, under the sclera, in the retina or sub-retinal space, under the skin using an implant containing medications such as Botox, or in other parts of the body using an implant which is coated with collagen to a desired thickness, dipped in a photosensitizer or has photosensitizer nanoparticles, such as riboflavin, etc. or the photosensitizer is injected surrounding the implant and implanted in desired location, such as under or over the sclera in the choroid, under the conjunctiva, etc. Then, ultraviolet (UV) radiation or another wavelength of light is used to cross-link the tissue at the desired power and duration depending on what technique is used. In these conditions, a focused UV or another wavelength of light is applied externally, in a painting oscillatory fashion only to the desired areas or internally through a fiber optic, etc. to activate the photosensitizer in the surrounding tissue where the implant is located. The cross-linked collagenous tissues surrounding the implant prevent creating an adhesion between the tissue and the implant or gluing the wall of the pocket together or to the implant. The cross-linked collagenous tissues surrounding the implant also have these additional benefits: (1) it is easier to replace the implant if needed, (2) fibrous ingrowth or encapsulation is prevented, (3) it permits injection of the cross-linker again to repeat the cross-linking process if needed, and (4) it prevents rejection of the implant and contributes to the slow release of the medication from the implant. Also, these implants can act as a shunt for glaucoma, or drainage shunt for cerebrospinal fluid, or other part of the body, such as a bladder neck for urine if the drainage system is provided with a unilateral valve that only opens when the bladder pressure increases to certain level, etc.

In one or more embodiments, the injection of a small amount of hyaluronic acid or other viscous fluid in the pocket simplifies the inserting of the implant in the peripheral corneal pocket or a pocket created in another tissue.

In one or more embodiments, the implant can be a biodegradable polymer carrying various medications and can be replaced.

In one or more embodiments, the implant is a tube-like structure having a thickness or diameter of 0.02 millimeters (mm) to 0.4 millimeters (mm) in one direction and up to 8 mm in another (flat) width, and being 1-60 mm long covering the entire corneal periphery without pressing the corneal tissue in any direction. The implant may be filled with a medication(s), a fluid, or a combination of them.

In one or more embodiments, the tube is not biodegradable having holes made in the wall of the tube with 0.2 to 3 microns in diameter, or 5 microns to 500 microns in diameter, to permit diffusion of the medications or cells placed in it to produce desired needed proteins, hormones, nerve growth factors, or other products needed for other body cell survival, such as cornea, retina, brain, etc.

In one or more embodiments, the tube has holes that are 5 to 15 microns in diameter so as to permit stem cells to exit the tube. The tube can be biodegradable implanted in a lightly cross-linked corneal pocket permitting, for example, stem cells to proliferate and/or migrate to the cornea. The stem cells can be obtained from limbal stem cells or mesenchymal stem or skin and cultured cells prior to the injection in the cornea or in another part of the body.

In one or more embodiments, the device is implanted in the wall of the vitreous cavity with one end closed and one end open to the vitreous cavity, or the implant can be under the retina or it can penetrate both the retina and the choroid and permit release of medication or the cells.

In one or more embodiments, the implant is implanted in the tissue surrounding the eye, on the face, etc. with one end closed and one end open to the tissue. The implant can be removed after the drug is released, and then replaced.

In one or more embodiments, the repeated crosslinking of the tissue surrounding the pocket can be performed as needed to prevent cellular ingrowth, and the implant can be removed and replaced as needed (e.g. in age related macular degeneration) to maintain delivery of the anti-glaucoma medication, anti-VEGFs, immunosuppressive or anti-inflammatory agents, or nerve growth factors, or Rho kinase inhibitors.

In one or more embodiments, the peripheral cross-linked pocket is used to insert or inject medications needed to treat a corneal disease, glaucoma, or a disease of the posterior segment. The medication can be in a form of nanoparticles, microparticles, micelles, liposomes, chitosans, polycaprolactone as nanoparticles, dendrimers, etc.

Figure 31A:
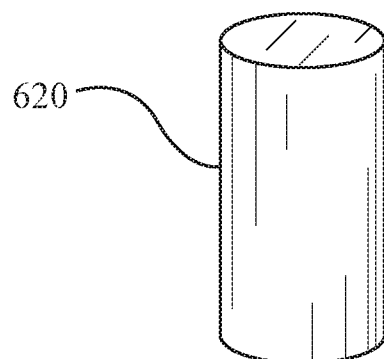
FIG. 31A illustrates a first exemplary form of the drug delivery implant described herein, which is in the form of a solid tubular implant.
Figure 31B:
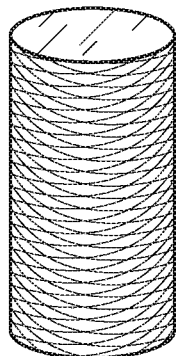
FIG. 31B illustrates a second exemplary form of the drug delivery implant described herein, which is in the form of a porous tubular implant.
Figure 31C:
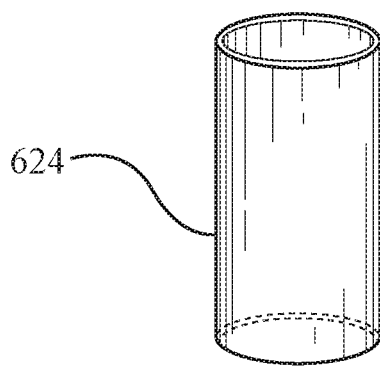
FIG. 31C illustrates a third exemplary form of the drug delivery implant described herein, which is in the form of a tubular implant with open ends.
Figure 35:
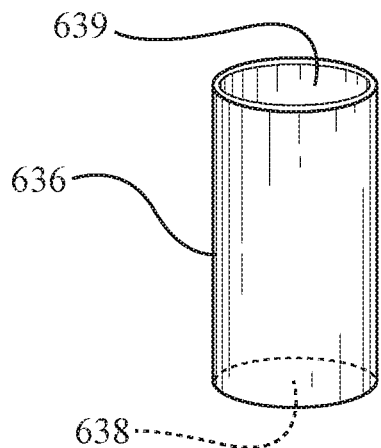
FIG. 35 illustrates yet another exemplary form of the drug delivery implant described herein, wherein the implant is in the form of a semi-solid or silicone tubular implant with one closed end and one open end.

In one or more embodiments, one can inject or insert an implant in the peripheral corneal pocket that is in the form of a large-sized flexible, semi-solid or solid, porous or solid rod-shaped implant, a flat implant, or tube-shaped implant that contains medication, or any shape and size polymeric material that can be absorbed with time and the medication is released slowly to the cornea or the anterior chamber of the eye or diffuses through the anterior chamber or through the sclera to the back of the eye, for treatment of the choroidal or retina and optic nerve diseases. As shown in FIGS. 31A-31C, the implant may be in the form of a solid implant 620, a porous implant 622, or a solid tubular implant 624 with an open end. Also, as shown in FIG. 35, the implant may be in the form of a semi-solid or silicone tubular implant 636 with one closed end 638 and one open end 639.

In one or more embodiments, the diameter of the rod or flat-shaped implant can have a length of 1 microns to a few millimeters (mm), or the length can be 1 to 40 millimeters (mm) or longer.

In one or more embodiments, the non-biodegradable tube is open-ended so that the medication exits only from one or both ends of the tube.

In one or more embodiments, the medication can be released for a duration of from 3 months to 3 or more years, such as when containing nanoparticles of fluoroquinolone dexamethasone, diclofenac, etc., and the implant can be replaced or removed if the desired effect has been achieved or reinjected in the corneal pocket.

In one or more embodiments, the tube is closed ended, but has pores for diffusion of the medication. For example, refer to the implants 626, 630 in FIGS. 32 and 33.

In one or more embodiments, the implant can be placed near any joint in the body and the cross-linking is done using ultraviolet (UV) radiation through the skin or through the fiber optic as described for localized drug delivery.

In one or more embodiments, the porous tube can be made of semipermeable non-biodegradable material that permits only the diffusion of fluid/medication, etc. in and out of the tube, and the tube is implanted in the peripheral cross-linked corneal pocket, wherein the tube can be refilled with medication as needed via an injection using a 33-34 gauge needle. For example, refer to FIG. 36.

In one or more embodiments, the tube contains cells in a biocompatible fluid that permits nutrition to reach the cells which are injected in the tube where the cells are immortalized to produce one or more medications, growth factors, such as a ciliary neurotrophic growth factor, RPE growth factor, nerve growth factors, anti-VEGFs, or other medications needed.

In one or more embodiments, the implant contains genetically modified cells producing other needed enzymes and medications. The combination of crosslinking of the cornea produces a wall of amorphous, acellular collagen and the corneal location that lacks vessels provides a suitable place for these cells in the tube implant to survive and produce medications as needed, which otherwise would have to be given repeatedly either locally or systemically, and in many genetic diseases of the cornea, such as Fuchs dystrophy, the cells have to be injected in the subconjunctival space where the cells could be attacked by the normal cellular body's immune response. The cross-linked pocket with the implant creates an immune-privileged space in the cornea or elsewhere for these cells to survive. For example, refer to FIGS. 38A-45B.

In one or more embodiments, the medication in the implant can be in any form or composition, such as antibiotics, anti-inflammatory, immune suppressants, anti-glaucoma medication, anti-vascular proliferation, stimulatory, such as Rho inhibitors. The polymers can be made of bio-degradable compounds, such as polylactic, polyglycolic acid or a combination of them, polycaprolactone, etc.

In one or more embodiments, the corneal cross-linked pocket contains a tubular implant filled with particulate immunosuppressive agents, such as cyclosporine etc., that release the medication at a constant, but low concentration of micrograms as needed. The medication diffuses in the cornea, sclera, and/or conjunctiva, thus eliminating the burning sensation of topical cyclosporine drops and the need for daily drop admiration in dry eye syndromes, or after refractive surgery or other diseases.

In one or more embodiments, the medication can be injected in the peripheral pocket along with corneal stem cells taken from the limbus or genetically modified stem cells and grown in the culture for implantation.

Figure 40A:
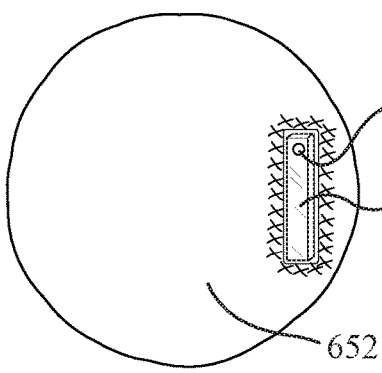
FIG. 40A is a front view of a cornea of an eye illustrating a tubular drug delivery implant disposed in a cross-linked pocket in the peripheral portion of the cornea, wherein the implant comprises a needle fluidly coupling the implant to the anterior chamber of the eye.
Figure 40B:
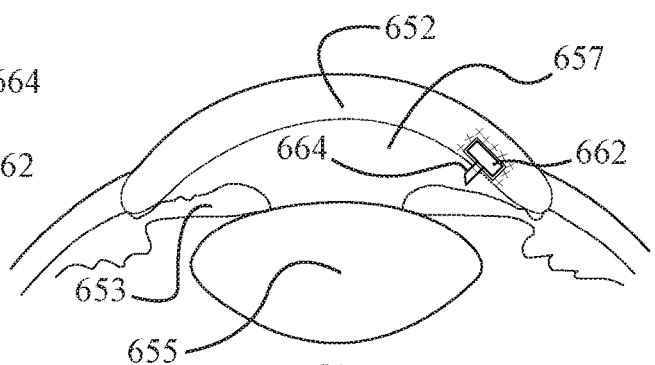
FIG. 40B is a partial side cross-sectional view of the eye of FIG. 40A illustrating the tubular drug delivery implant with the needle extending into the anterior chamber of the eye.
Figure 45A:
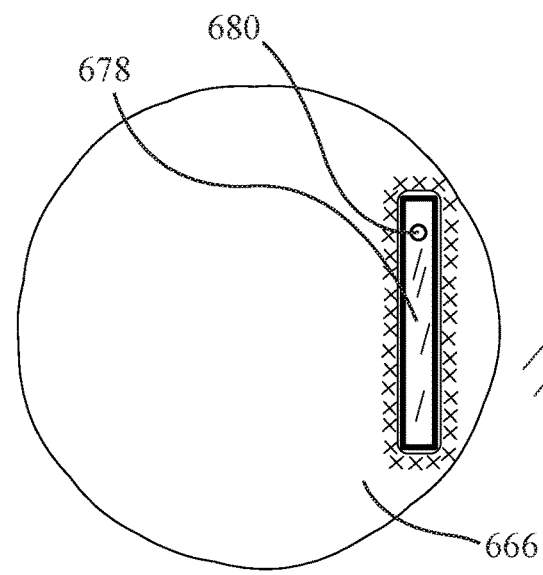
FIG. 45A is a front view of a cornea of an eye illustrating a drug delivery implant disposed in a cross-linked pocket in the peripheral portion of the cornea, wherein the implant comprises a needle fluidly coupling the implant to the anterior chamber of the eye.
Figure 45B:
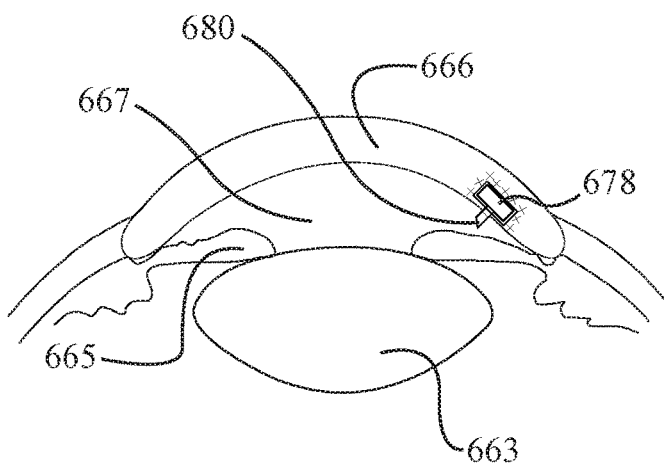
FIG. 45B is a partial side cross-sectional view of the eye of FIG. 45A illustrating the tubular drug delivery implant with the needle extending into the anterior chamber of the eye with the aqueous fluid of the eye.

In one or more embodiments, as shown in FIGS. 40A and 40B, a non-biodegradable implant tube 662 as described herein is implanted in the cross-linked corneal pocket of the cornea 652 of the eye with iris 653 and lens 655, and the implant tube 662 is connected to the anterior chamber 657 with the aqueous fluid via a thin 23-34 gauge needle 664, where biomarkers such as VEGFs, glucose, and analytes, etc. are present both inside the aqueous and the tube system made of soft silicone. Similarly, as depicted in FIGS. 45A and 45B, an implant 678 is implanted in the cross-linked corneal pocket of the cornea 666 of the eye with iris 665, and the implant 678 is connected to the anterior chamber 667 with the aqueous fluid via a needle 680. The implants 662, 678 can be penetrated with a 30-34 gauge needle from outside and the aqueous can be aspirated in a volume of less than 0.50 microliters repeatedly over a long period of time without causing a collapse of the anterior chamber. The volume of the anterior chamber is 25 times more than the sample fluid taken. The minimal amount of aqueous fluid withdrawn will be replaced by the eye in less than 10 minutes. This provides a means of obtaining easily a fluid biopsy repeatedly from the eye without penetrating the entire cornea or the eye wall directly with the complication of iris or lens injury and retinal injury. The fluid sample can be examined in chronic disease processes, such as uveitis for biomarker of a disease, viral infection that persist in the eye long after the body has healed, such as Ebola, Zika, Herpes viruses or other viral diseases or non-viral infections that can be detected and treated appropriately. The biomarkers can be obtained from the implanted tube, and can provide valuable information on many metabolic diseases of the body or the eye, a systemic disease (e.g., Alzheimer disease), age related macular degeneration, glucose level, or other analytes (e.g., diabetes) in diabetic retinopathy and other slow progressive degenerative eye diseases, tumors, infection, uveitis, poisoning or drug overdose, etc.

In one or more embodiments, a plurality of implants are implanted in the cornea of the eye. In these one or more embodiments, each of the implants is used for a different purpose. For example, a first one of the implants may be in form of a corneal drug delivery implant used for delivering one or more medications to the eye, as described above. A second one of the implants may be used for taking liquid biopsies from a portion of the eye, as described herein (e.g., extracting a liquid biopsy of the aqueous fluid from the anterior chamber of the eye). A third one of the implants may be used for stem cell delivery and/or gene therapy in the manner described above. A fourth one of the implants may be used for measuring the intraocular pressure of the eye of the patient (e.g., intracorneal implant comprising a pressure sensor). That is, the fourth implant may contain a pressure sensor configured to measure an intraocular pressure of an eye and to output a signal based on the measured intraocular pressure of the eye, the pressure sensor configured to be implanted in a cornea of the eye; a processor operatively coupled to the pressure sensor, the processor configured to generate intraocular pressure data based upon the signal outputted by the pressure sensor; and a transmitter device operatively coupled to the processor, the transmitter device configured to transmit the intraocular pressure data generated by the processor to a remote receiver located outside of the eye, the transmitter device configured to be implanted in the cornea of the eye. In addition to the pressure sensor, the third implant may further comprise a needle configured to penetrate a posterior portion of the cornea of the eye, the needle configured to open into the anterior chamber of the eye so as to measure the intraocular pressure of the eye without obstructing vision through the central cornea.

In one or more embodiments, one can measure the amount of VEGF present in the aqueous providing information on the disease progression requiring treatment (e.g., anti-VEGFs or no treatment). Anti-VEGFs or another medication can be administered directly in the tube to reach the posterior segment avoiding repeated intraocular injection through the sclera, without having the risk of retinal detachment or lens injury. As another example, liquid biopsy of aqueous in a patient with diabetic retinopathy, where the retina is in need of treatment with the laser coagulation, provides the information regarding whether the disease process is under the control or not.

In one or more embodiments, for the first time one can obtain from the aqueous biopsy, instant information needed for the doctor to diagnose a disease process at the bedside and be able to follow the process over a long period of time with ease.

In one or more embodiments, nanoparticles carrying other medications can be delivered as slow release nanoparticles from the tube in the anterior chamber to treat glaucoma for a long period of time, thereby eliminating the need for repeat therapy. These medications may include pilocarpine, prostaglandin analogues for treatment of glaucoma, Rho kinase inhibitors, or neuroprotective agents or Brimonidine, etc.

In one or more embodiments, the implanted tube is filled with desired medications, as described above, and is coated with collagen or albumin loaded with riboflavin particles that are diffused after implantation in the pocket. The ultraviolet (UV) radiation used for cross-linking permits the diffusing of the medication from the implant as a slow release device, and prevents vascular growth around the implant containing the medication.

In one or more embodiments, the implanted tube can be 100 microns to 1 millimeters (mm) in diameter and 4 mm to 40 mm long, or less than 100 micron in diameter and no longer than a few millimeters in length. The implanted tube may be filled with any desired medication to be implanted in any tissue and cross-linked after implantation.

Methods disclosed hereinafter include administering Wnt inhibitors either alone, or in combination with Rho inhibitors, or one or more Wnt inhibitors with the dendrimers or liposomes, or (alpha)-cyclodextrin, (beta)-cyclodextrin, (gamma)-cyclodextrin, hydroxypropyl-b-cyclodextrin (bHPCD that are useful for alleviating the effects of conditions that are caused by acute or chronic inflammatory processes, such as chronic inflammatory dry eye disease, diabetes, optic nerve neuritis, scleritis, keratitis, chronic Meibomian gland inflammation, and uveitis.

In one embodiment, Wnt inhibitors or Rho kinase inhibitors with the dendrimers or liposomes, or as nano- or microparticles with (alpha)-cyclodextrin, (beta)-cyclodextrin, (gamma)-cyclodextrin, hydroxypropyl-b-cyclodextrin (bHPCD are used as topical drops, spray, ointment, gel, or a non-toxic injectable formulation under the conjunctiva, in the corneal pocket, or in the vitreous to treat the dry eye syndrome or mucosal inflammatory diseases, such as uveitis, optic nerve neuritis, diabetic macular edema, cystoid macular edema after cataract surgery, macular edema in uveitis, vasculitis, Behçet's disease, sarcoidosis, multiple sclerosis, lichen planus, chronic joint disease arthritis, chronic choroiditis, plantar fasciitis, pars planitis, scleritis, iritis, and/or scleritis gingivitis.

A method of treating dry eye with deficiency of aqueous production which is associated often with the Meibomian gland disease, affecting about 7% to 34% of all Americans, pathophysiology of chronic dry eye disease including a cycle of inflammation involving both innate and adaptive immune responses is also disclosed herein.

In one embodiment, dry eye syndrome (DES) or keratoconjunctivitis sicca, a disease affecting tear production leading to damage to the corneal surface, associated often with disturbance of Meibomian gland, lachrymal gland, conjunctival goblet cells, nasolacrimal duct and pain sensation is treated by Wnt inhibitors or Rho kinase inhibitors used as topical drops, ointment, gel, non-toxic injectable formulation such as nano- or microparticles with (alpha)-cyclodextrin, (beta)-cyclodextrin, (gamma)-cyclodextrin, hydroxypropyl-b-cyclodextrin (bHPCD).

In one embodiment, the method used for treatment of the eye utilizes over the counter physiological saline solutions with some other components to affect the inflammatory component of the dry eye or improve on the composing of the tear film, such as tear film osmolarity, or adding lipids, mucin, etc. Other topical medication include TheraTears® (Advanced Vision Research), Refresh® and Celluvisce® (Allergan), Tears Natural® and Bion Tears® (Alcon), GenTeal® and HypoTears® (CIBA Vision), each of which contain electrolytes and has varying pH levels, osmolarities, Restasis® (0.05% cyclosporine, Allergan), and Xiidra® (5% lifitegrast, Shire), which attacks the inflammatory process by a different mechanism than cyclosporine. Most of these medications are applied as a drop to maintain the conjunctival wetness as needed usually 1-3 drops during the day or ointment at night most of these medications may be used in combination with Rock inhibitors, such as Fasudil, or Wnt inhibitors.

In one embodiment, the Rock inhibitors not only reestablishes the tear production by reducing the conjunctival inflammatory cytokines and inflammatory response, but enhances the nerve fibers to grow and reestablish the function of conjunctival goblet cells to produce mucin, which is essential for tear film lubrication. RHO associated protein Kinase (Rock) is a kinase belonging to the family of serine-threonine Kinase involved in regulating the shape and the cytoskeleton of the cells, it is an important regulator of cell migration, stimulates PTEN phosphatase activity, leading to uncontrolled cell division in cancer. Rock is active in inflammatory processes, cancer, diabetes, and many neurodegenerative diseases such as dry or wet form of age related macular degeneration. Therefore, Rock inhibitors inhibit inflammatory processes.

In one embodiment, Rock inhibitors may be used in combination with functionalized nanoparticles of polycaprolactone, polylactic or polyglycolic acid, as nano- or microparticles with (alpha)-cyclodextrin, (beta)-cyclodextrin, (gamma)-cyclodextrin, hydroxypropyl-b-cyclodextrin (bHPCD etc. to reduce the inflammation during immune therapy or thermoimmune therapy.

In one embodiment, a potent ROCK inhibitor administered systemically, locally, as an implant, orally, topically as functionalized nanoparticles, microparticles, dendrimers or such as bioavailable Fasudil hydrochloride, inhibitor of cyclic nucleotide dependent- and Rho-kinases GSK 269962 is used. In one embodiment, potent and selective ROCK inhibitor GSK 429286, Selective Rho-kinase (ROCK) inhibitor H1152 dihydrochloride, or Botox, Wnt inhibitors, and brimonidine are used as an implant for slow release of the medication.

In one embodiment, selective Rho-kinase (ROCK) inhibitor Glycyl H 1152 dihydrochloride, or another selective Rho-kinase (ROCK) inhibitor is administered as a topical ointment, drop, or gel. Also, a more selective analogue of H1152, that is cell-permeable, a selective Rho-kinase inhibitor OXA 06 dihydrochloride, a potent ROCK inhibitor PKI1447 dihydrochloride, potent and selective ROCK inhibitor antitumor SB 772077B, a potent Rho-kinase inhibitor, vasodilator SR 3677 dihydrochloride, a potent, selective Rho-kinase (ROCK) inhibitor TC-S7001, a potent and highly selective ROCK inhibitor, orally active Y-27632 dihydrochloride or Botox also may be administered as nano- or microparticles with (alpha)-cyclodextrin, (beta)-cyclodextrin, (gamma)-cyclodextrin, hydroxypropyl-b-cyclodextrin (bHPCD).

In one embodiment, ROCK inhibitors include, but are not limited to, Fasudil, Ripasudil, RK1-1447, Y-27632, GSK429286A, Y-30141, etc. They may be administered in a polymer, an implant, microparticles or nanoparticles, or porous silicone implant, etc. They may also contain poly (amidoamine) (PAMAM), poly(amidoamine-organosilicon) (PAMAMOS), poly(propyleneimine) (PPIO), poly(caprolactone), poly(lactic acid) (PLA), polylactic-co-glycolic acid (PLGA); may be tecto, multilingual, chiral, hybrid, amphiphilic, micellar, multiple antipen peptide, and Frechet-type dendrimers; may be functionalized microparticles or nanoparticles with an antibody and/or a ligand for a receptor or covalent coupling to one or more of cell penetrating peptides (CPP), arginine-CPP, cysteine-CPP, polyethylene glycol (PEG), biotin-streptavadin, and/or acetyl cysteine or as nano- or microparticles with (alpha)-cyclodextrin, (beta)-cyclodextrin, (gamma)-cyclodextrin, hydroxypropyl-b-cyclodextrin (bHPCD).

In one embodiment, ROCK inhibitors include, but are not limited to, Fasudil, Ripasudil, RK1-1447, Y-27632, GSK429286A, Y-30141, etc. They may be administered in a suspension, or solution over the cornea or injected inside the corneal channel provided with a femtosecond laser as nano- or microparticles with (alpha)-cyclodextrin, (beta)-cyclodextrin, (gamma)-cyclodextrin, hydroxypropyl-b-cyclodextrin (bHPCD).

In one embodiment, the implant may be a C-shaped or ring-shaped flexible implant with a diameter of the implant of 20 microns to 200 microns or more, with a length of 1-12 mm and if it is circular with the diameter of 3-8 mm or less than the diameter of the lens capsule after cataract extraction without exerting any pressure or tension on the lens capsule or expanding it. In one embodiment, the polymeric material can be or porous silicone implant etc. They may also contain poly(amidoamine) (PAMAM), poly(amidoamine-organosilicon) (PAMAMOS), poly(propyleneimine) (PPIO), poly (caprolactone), poly(lactic acid) (PLA), polylactic-co-glycolic acid (PLGA); may be tecto, multilingual, chiral, hybrid, amphiphilic, micellar, multiple antipen peptide, and Frechet-type dendrimers; may be functionalized microparticles or nanoparticles with an antibody and/or a ligand for a receptor or covalent coupling to one or more of cell penetrating peptides (CPP), arginine-CPP, cysteine-CPP, polyethylene glycol (PEG), biotin-streptavadin, and/or acetyl cysteine or as nano- or microparticles with (alpha)-cyclodextrin, (beta)-cyclodextrin, (gamma)-cyclodextrin, hydroxypropyl-b-cyclodextrin (bHPCD).

In one embodiment, the implant is injected in the cornea or scleral pocket using a 20 gauge or 25 gauge or 27 gauge or 30 gauge needle.

Figure 46:
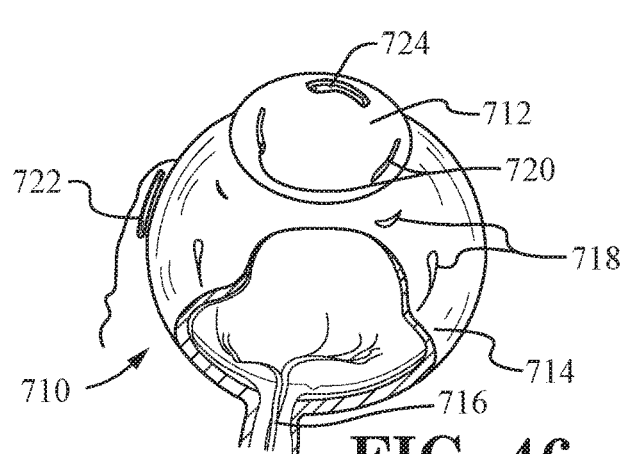
FIG. 46 is a cutaway perspective view of an eye with a drug delivery implant disposed in a pocket formed in the corneal stroma of the eye.
Figure 47:
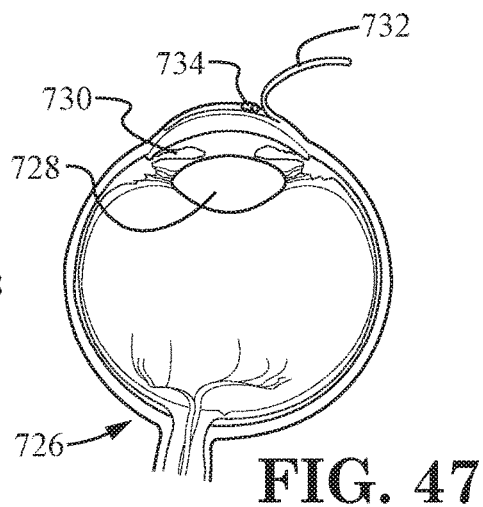
FIG. 47 is a cross-sectional view of an eye illustrating the formation of a corneal LASIK flap in the eye.
Figure 48:
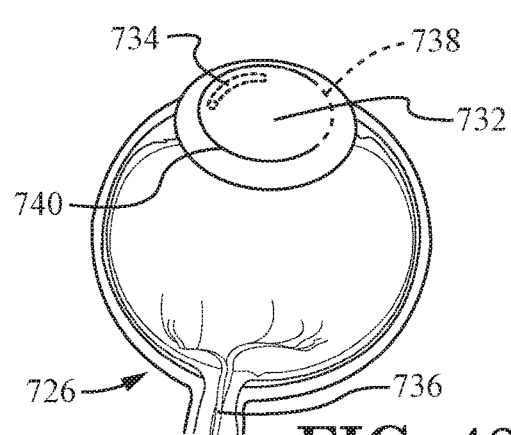
FIG. 48 is a cutaway perspective view of the eye of FIG. 47, wherein a drug delivery implant has been placed under the corneal LASIK flap.

In one embodiment, one or more corneal pockets 720 are produced in the corneal stroma 712 of an eye 710 with a femtosecond laser or a small knife (see FIG. 46) or one or more scleral pockets 718 are formed in the sclera 714 of the eye 710 or under the conjunctiva and the implant 724 carrying Rho inhibitors, Wnt inhibitors, Fingolimod, or antibiotics, is placed in the pocket 718 or 720. As shown in FIG. 46, a subconjunctival implant 722 may also be implanted in the eye 710 with optic nerve 716. In another embodiment, a femtosecond laser flap or a flap formed by a knife is created in the corneal stroma of an eye 726 as a LASIK flap 732 and after correcting the refractive error either with an excimer laser or an inlay, then an implant 734 is placed under the corneal flap 732 (see FIGS. 47-48). As shown in FIGS. 47 and 48, the eye 726 with lens 728, iris 730, and optic nerve 736 comprises a corneal drug delivery implant 734 disposed in the stromal tissue underneath the LASIK flap 732. FIG. 48 illustrates the eye 726 after the flap 732 has been replaced. In FIG. 48, the attached area of the flap 732 is represented by the dashed line 738, while the flap incision is represented by the solid line 740. In yet another embodiment, a corneal pocket is created with femtosecond laser and an inlay is placed inside the pocket to correct refractive error of the eye followed with implantation of an implant in the pocket for drug delivery and the implant carrying Rho inhibitors, Wnt inhibitors, Fingolimod, or antibiotics as nano- or microparticles with (alpha)-cyclodextrin, (beta)-cyclodextrin, (gamma)-cyclodextrin, hydroxypropyl-b-cyclodextrin (bHPCD), etc.

Figure 49:
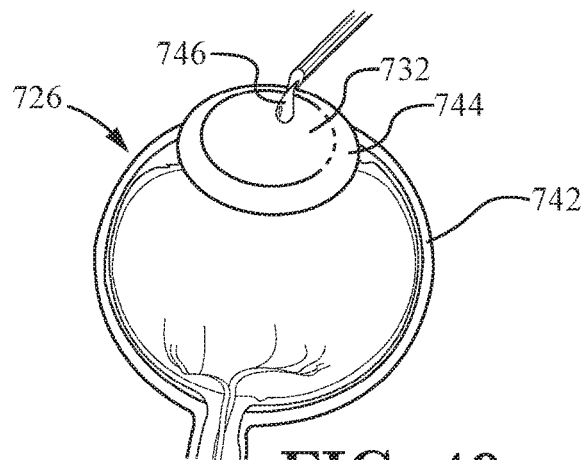
FIG. 49 is a cutaway perspective view of an eye illustrating the application of a medication to the cornea of the eye by drops.

In another embodiment, after refractive surgery, the polymeric medication is applied either as a drop 746 or spraying to the cornea 744 of eye 726 with sclera 742 (see FIG. 49).

Figure 50:
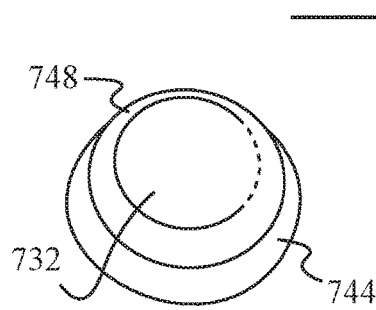
FIG. 50 is a front view of a cornea of an eye illustrating a polymeric contact lens containing a medication disposed on the cornea of the eye after the eye has undergone refractive surgery or a traumatic corneal injury.

In yet another embodiment, after refractive surgery or traumatic corneal injury, a soft polymeric contact lens 748 carrying medication is placed over the cornea 744 to protect it and treat it with medication (see FIG. 50), and the implant carrying Rho inhibitors, Wnt inhibitors, Fingolimod, or antibiotics, Fasudil, brimonidine, etc. with (alpha)-cyclodextrin, (beta)-cyclodextrin, (gamma)-cyclodextrin, hydroxypropyl-b-cyclodextrin (bHPCD).

Figure 51:
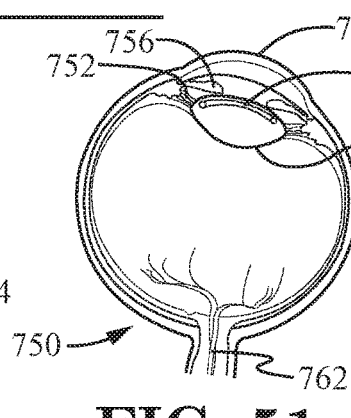
FIG. 51 is a cross-sectional view of an eye illustrating an intracapsular drug delivery implant after the eye has undergone cataract surgery.

In another embodiment, the polymeric drug delivery implant 760 has a C-shape or has a ring or a curved shape and is placed in the lens capsule 754 of an eye 750 without expanding or putting tension or pressure on the capsule and the implant 760 carrying Rho inhibitors, Fasudil, or Wnt inhibitors, Fingolimod, or antibiotics, an agent to lower the intraocular pressure (IOP), NSAIDs, with as nano- or microparticles and/or with (alpha)-cyclodextrin, (beta)-cyclodextrin, (gamma)-cyclodextrin, hydroxypropyl-b-cyclodextrin (bHPCD, etc. The polymeric implant 760 can be placed, either before or after the intraocular lens (IOL) implantation. The drug delivery implant 760 never covers the view of the patient (see FIG. 51). In FIG. 51, it can be seen that eye 750 with lens zonules 752, lens capsule 754, iris 756, and cornea 758 comprises an intracapsular C-shaped or ring-shaped drug delivery implant 760 that has been inserted into the lens capsule 754 after cataract surgery on the eye 750.

Figure 52:
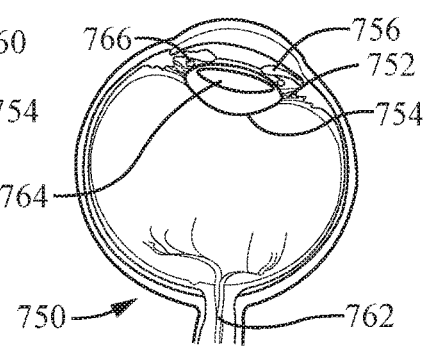
FIG. 52 is a cross-sectional view of an eye illustrating a drug delivery implant that has been placed on the lens capsule of the eye after the eye has undergone cataract surgery.

In one embodiment, an implant 766 (e.g., a C-shaped or ring-shaped drug delivery implant 766) is placed over the lens capsule 754 before the crystalline lens is removed or can be placed on the lens zonules 752 after cataract extraction and intraocular (IOL) lens 764 implantation (see FIG. 52), and the implant carrying Rho inhibitors, or Wnt inhibitors, or Fingolimod, or antibiotics or an agent to lower IOP, such as prostaglandin analogues, NSAIDs, etc.). In FIG. 52, it can be seen that eye 750 with lens zonules 752, lens capsule 754, iris 756, optic nerve 762, and retina 768 comprises an intracapsular C-shaped or ring-shaped drug delivery implant 766 disposed over the lens zonules 752.

In one embodiment, the polymeric material is administered to the vitreous before or after removal of the vitreous for both visualization and delivery of medication to the eye, and the implant carrying either Rho inhibitors, or Wnt inhibitors, or Fingolimod, or antibiotics, NSAIDs, etc. as nano- or microparticles with (alpha)-cyclodextrin, (beta)-cyclodextrin, (gamma)-cyclodextrin, hydroxypropyl-b-cyclodextrin (bHPCD).

Figure 53:
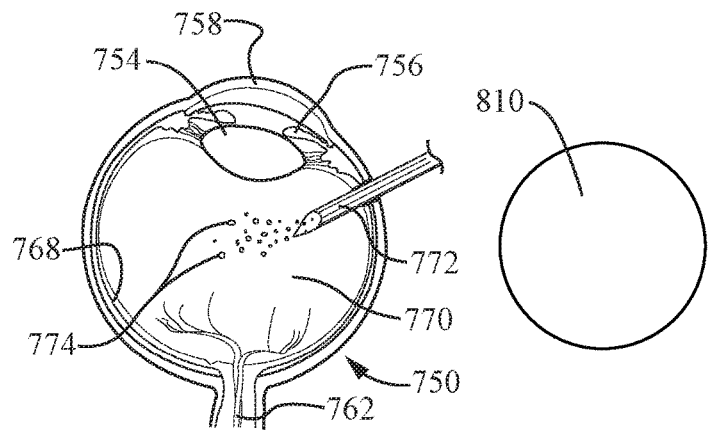
FIG. 53 is a cross-sectional view of an eye illustrating intravitreal administration of a medication by injecting the medication along with microparticles or nanoparticles.

In one embodiment, the polymeric drug delivery carrier can be nanoparticles or microparticles or up to one mm in diameter injected as nano- or microparticles with (alpha)-cyclodextrin, (beta)-cyclodextrin, (gamma)-cyclodextrin, hydroxypropyl-b-cyclodextrin (bHPCD) compound in the eye cavity or in the pocket created in the cornea or sclera or under the conjunctiva to place an implant. For example, as shown in FIG. 53, nanoparticles or microparticles 774 carrying one or more medications may be injected into the vitreous cavity 770 of an eye 750 using a needle 772. In FIG. 53, it can be seen that eye 750 with lens capsule 754, iris 756, cornea 758, optic nerve 762, and retina 768 is being treated with nanoparticles or microparticles 774 carrying one or more medications that are injected into the vitreous cavity 770.

In one embodiment, the implant is visible by the nature of the medication it carries or may be transplanted such as implants (if more than one implant is provided) and comprises one or more medications selected from the group consisting of immunosuppressive agents, calcineurin inhibitors, mycophenolic acid, tacrolimus, siraliums, steroids, MPP inhibitors, NSAIDs, antimetabolytes, polycolonal antibodies, monocolonal antibodies, TNF inhibitors, Rho inhibitors, Wnt inhibitors, Fingolimod, antibiotics, Brimonidine an intraocular pressure (TOP) lowering agents, pilocarpine, prostaglandin analogues, anti-virals, anti-VEGFs, biologics, neuroprotective medications, and combinations thereof as a preparation to penetrate the tissue and the cells using as nano- or microparticles with (alpha)-cyclodextrin, (beta)-cyclodextrin, (gamma)-cyclodextrin, hydroxypropyl-b-cyclodextrin (bHPCD).

In one embodiment, aqueous tear-deficient dry eye, occurring as a result of not enough tears being produced due to a dysfunction of the lacrimal glands, is treated with Wnt inhibitors or Rho kinase inhibitors as topical drops, ointment, gel, or a non-toxic injectable formulations as nano- or microparticles with (alpha)-cyclodextrin, (beta)-cyclodextrin, (gamma)-cyclodextrin, hydroxypropyl-b-cyclodextrin (bHPCD) for tissue and cell penetration and slow release.

In one embodiment, the Wnt inhibitors compound that is used includes FH535, IWP-2, PNU-74654, IWR-lendo, IWR-exo, demethoxycurcumin, sulforaphane and vitamin D, CCTO36477, KY02111, WAY-316606, SFRP, IWP, LGK974, C59, Ant1.4Br/Ant 1.4Cl, ivermectin, niclosamide, apicularen and bafilomycin, XAV939, XAV939, G007-LK and G244-LM, NSC668036, SB-216763, gemtuzumab, and akinumab as nano- or microparticles with (alpha)-cyclodextrin, (beta)-cyclodextrin, (gamma)-cyclodextrin, hydroxypropyl-b-cyclodextrin (bHPCD because of their hydrophilic and hydrophobic nature.

In one embodiment, patients with moderate-to-severe dry eye having both elements of evaporative dry eye and aqueous tear-deficient dry eye, and that are on topical medications for other diseases, such as glaucoma, drops, or antibiotics containing preservative that over time damage the conjunctival goblet cells and other cells and induce dry eye syndrome, are treated with Wnt inhibitors or Rho kinase inhibitors as topical drops, ointment, gel, or a non-toxic injectable formulation or as nano- or microparticles with (alpha)-cyclodextrin, (beta)-cyclodextrin, (gamma)-cyclodextrin, hydroxypropyl-b-cyclodextrin (bHPCD) to release medication slowly without causing irritation of the conjunctiva or the cornea.

In one embodiment, administration of Wnt inhibitors, such demethoxycurcumin, sulforaphane and vitamin D, or Rho kinase inhibitors, such as Fasudil derivatives, is done as topical drops, a gel, a non-toxic injectable formulation, or as nano- or microparticles with (alpha)-cyclodextrin, or (beta)-cyclodextrin, or (gamma)-cyclodextrin, hydroxypropyl-b-cyclodextrin (bHPCD) or injectable Botox, 1-100 units as needed, administered locally at multiple locations with the same formulation having nano- or microparticles with (alpha)-cyclodextrin, or (beta)-cyclodextrin, or (gamma)-cyclodextrin, hydroxypropyl-b-cyclodextrin (bHPCD or Rock inhibitors molecules at doses of 1 picogram (pg) to nanograms to a few micrograms as a slow release delivery system.

In one embodiment, patients who are on topical medications for other diseases, such as glaucoma, drops or antibiotics containing preservatives and over time damage the conjunctival goblet cells and other cells and induce dry eye syndrome, or patients with dry eye and glaucoma are treated either by implanting matrices polylactic acid or poly glycolic acid, polyanhydride, or as nano- or microparticles with (alpha)-cyclodextrin, or (beta)-cyclodextrin, or (gamma)-cyclodextrin, hydroxypropyl-b-cyclodextrin (bHPCD) or chitosan polymers under the conjunctiva with slow release polymers containing either Wnt inhibitors or Rock inhibitors, such as Botox or Fasudil derivatives, releasing the medication over months or years locally at multiple locations to release the non-toxic doses of the medications from 1 picogram (pg) to 1 nanograms (ng) or more each day.

In one embodiment, patients who develop dry eye as a result of systemic medication, such as in cancer patients developing dry eye after administration of checkpoint inhibitors in cancer immune therapy, are treated either by Wnt inhibitors or Rock inhibitors with slow release polymers containing either Wnt inhibitors, such as demethoxycurcumin, CCTO36477, KY02111, WAY-316606, SFRP, IWP, LGK974, C59, Ant1.4Br/Ant 1.4Cl, nitazoxanide (NTZ) ivermectin, niclosamide, sulforaphane and vitamin D, or Rock inhibitors, such as Botox or Fasudil derivatives, etc., releasing the medication over months or years locally at multiple locations to release the non-toxic doses slow release medications from 1 picogram to 10 nanograms each day or more using nano- or microparticles with (alpha)-cyclodextrin, or (beta)-cyclodextrin, or (gamma)-cyclodextrin, hydroxypropyl-b-cyclodextrin (bHPCD).

In one embodiment, the Sjorgen syndrome is associated with low salivary flow, lymphocytic infiltration of the lacrimal gland and salivary gland auto antibodies in serum, rheumatoid factor, connective tissue diseases, such as Sjogren's syndrome, to the list of immune-related adverse events that can develop during cancer treatment with immune checkpoint inhibitors are treated with Rock inhibitors and Wnt inhibitors at non-toxic concentrations of sulforaphane and vitamin D, CCTO36477, KY02111, WAY-316606, SFRP, IWP, LGK974, C59, Ant1.4Br/Ant 1.4Cl, nitazoxanide (NTZ), ivermectin, niclosamide, or Rock inhibitors such as Botox or Fasudil etc., releasing the medication slowly over months or years locally at multiple locations to release the non-toxic doses slow release medications from 1 pg to 10 ng each day locally using as nano- or microparticles with (alpha)-cyclodextrin, or (beta)-cyclodextrin, or (gamma)-cyclodextrin, hydroxypropyl-b-cyclodextrin (bHPCD) for slow release and tissue penetration.

In one embodiment, the patients being treated have a dry eye syndrome unassociated with SS (non-SS KCS) with a sensation of foreign body in the eyes, photophobia, excessive tearing, ocular irritation and pain. Other symptoms are increased tear film osmolality, decrease in tear breakup time, increase in the conjunctival enzymes metalloproteinase 9 and 17, and changes in impression cytology of the conjunctival cells. These patients are treated with Rock inhibitors, such as injectable Botox, 1-10 units or in combination with metalloproteinase inhibitors doxycycline, low molecular with weight heparin, lovenox, and dexamethasone at concentration of 0.1%-5% as polymeric implant or as nano- or microparticles with (alpha)-cyclodextrin, or (beta)-cyclodextrin, or (gamma)-cyclodextrin, hydroxypropyl-b-cyclodextrin (bHPCD).

In one embodiment, when inflammation is one of the mechanisms that causes damage to the ocular surface in dry eye disease seen in autoimmune diseases such as Sjögren's syndrome, and rheumatoid arthritis and neuropathic disorders, optic nerve neuritis, papillitis, scleritis, uveitis, inflammatory, infectious, chemical, traumatic diseases, etc., the patients are treated with injectable Rock inhibitors, such as Botox or Fasudil derivatives, conjugated with slow release polymer, such as porous silicone, etc. releasing the medication over months or years locally at multiple locations as the non-toxic doses slow release medications months to a year at concentration of 1 picogram to 10 nanograms each day.

In one embodiment, the pathological conditions resulting in dry eye include pemphigus and Sjogren's syndrome, which affect the eye by either damaging the conjunctival cells responsible for maintaining the wetness of the cornea and the conjunctiva, or by damaging the lacrimal glands of the eye and/or the meibomian glands of the eye lid or other pathological conditions resulting in dry eye include hypolacrimation, alacrima, Stevens-Johnson syndrome, marginal blepharitis pemphigus, ocular pemphigoid, scleritis, or diabetes are treated with Rock inhibitor Fasudil, Botox, etc. at a picogram to nanogram concentration or in combination with metalloproteinase inhibitors, doxycycline 0.1%-5% solution, low molecular weight heparin 0.1%-5% solution, or dexamethasone 0.1-2% solution in combination with MTOR inhibitors at 0.1%-5% solution or as nano- or microparticles with (alpha)-cyclodextrin, or (beta)-cyclodextrin, or (gamma)-cyclodextrin, hydroxypropyl-b-cyclodextrin (bHPCD) solution or suspension.

In one embodiment, the dry eye of patients occurring in post-corneal surgery (including but not limited to post-LASIK surgery or PRK) with surgical damage to the corneal nerves, other conditions resulting in dry eye including the aging process, environmental factors (e.g., dry home and/or work environments), and extended use of visual display terminals (e.g., employment, recreation) are treated with Rock inhibitors, or in combination with metalloproteinase inhibitors, low molecular with heparin, or Wnt inhibitors or Rock inhibitor, such as Botox, 1-100 units administered locally at multiple locations, small doses or Rock inhibitors molecule, Fasudil and its derivatives, etc., at doses of 1 nanogram (ng) to a few micrograms (µg) as slow release polymer or as nano- or microparticles with (alpha)-cyclodextrin, or (beta)-cyclodextrin, or (gamma)-cyclodextrin, hydroxypropyl-b-cyclodextrin (bHPCD).

In one embodiment, the dry eye can also occur after cataract surgery and refractive surgery (i.e., the LASIK procedure or PRK) and photorefractive keratectomy, smile procedure, partial or complete corneal transplants, which are the majorities of present refractive surgery where these procedures are performed, but dry eye is more common with LASIK where the superficial nerves are cut, and where the eye dries out because the corneal reflex is affected and the eye subsequent to these surgeries becomes dry while many eyes experience regeneration of the nerves, but it takes about one year or more to achieve it all. Patients with these conditions are treated with Rock inhibitors, or in combination with metalloproteinase inhibitors, low molecular with heparin, or Wnt inhibitors or Rock inhibitors, such as Botox, 1-100 units administered locally over the cornea as drops 1-4 times daily or injectable preparation at multiple locations, small doses or Rock inhibitors molecule, such as Fasudil or its derivatives, etc., at doses of 1 nanogram or a few micrograms as slow release non-toxic preparation or as nano- or microparticles with (alpha)-cyclodextrin, or (beta)-cyclodextrin, or (gamma)-cyclodextrin, hydroxypropyl-b-cyclodextrin (bHPCD).

In one embodiment, patients with paresis or paralysis of the fifth or seventh cranial nerves causing dry eye as a result of interfering with proper lid closure are treated with Rock inhibitors, such as Botox, 1-10 units administered topically over the cornea at multiple locations, small doses or Rock inhibitors molecule Fasudil, or its derivatives, etc. at doses of 1 nanogram to a few micrograms as topical ointment, drop, gel, etc.

In one embodiment, Wnt signaling is involved in the control of stem cell proliferation. Wnt mutation causes developmental defects in many disease processes including inflammation and cancer, wet form of age related macular degeneration, laser surgery, diabetic macular edema retinal vascular occlusion.

In one embodiment, the Wnt inhibitors compounds used are: FH535, IWP-2, PNU-74654, IWR-lendo. IWR-exo, nitazoxanide (NTZ), demethoxycurcumin, sulforaphane and vitamin D, CCTO36477, KY02111, WAY-316606, SFRP, IWP, LGK974, C59, Ant1.4Br/Ant 1.4Cl, Ivermectin, Niclosamide, apicularen and bafilomycin, XAV939, XAV939, G007-LK and G244-LM, NSC668036, SB-216763, gemtuzumab, akinumab Wnt inhibitors administered as nano- or microparticles with (alpha)-cyclodextrin, or (beta)-cyclodextrin, or (gamma)-cyclodextrin, hydroxypropyl-b-cyclodextrin (bHPCD).

In one embodiment, the oral doses for the Wnt inhibitor niclosamide is 1 to 2 g tablet once, or to repeat in 7 days, if needed.

In one embodiment, the small molecule Fasudil, a rock inhibitor Fasudil (HA-1077), a selective RhoA/Rho kinase (ROCK) inhibitor, or Y-27632, small molecule inhibitor of ROCK1 and ROCK2, Botulinum toxin a is rock inhibitor marketed under the brand names Botox, Dysport, Myobloc, Xeomin, etc. Botulinum toxin, all having good penetration into the cornea, and do not increase intraocular pressure or cause cataracts and may be dissolved in an organic solvent such as DMSO or alcohol or sterol, lanosterol, squalene, and/or squalamine, or containing a polyanhydride, poly (glycolic) acid, poly(lactic) acid, or polycaprolactone polymer or as nano- or microparticles with (alpha)-cyclodextrin, or (beta)-cyclodextrin, or (gamma)-cyclodextrin, hydroxypropyl-b-cyclodextrin (bHPCD) for the treatment of the lid, conjunctiva, lacrimal gland corneal diseases and glaucoma.

In one embodiment, Fasudil is used as a single, oral 40-80 milligram (mg) dose orally as two 40 mg Fasudil tablets are administered.

In one embodiment, the methods include administering Wnt inhibitors, either alone or in combination with Rho inhibitors, orally, locally by injection or drops, spray or ointment for alleviating the effects of conditions that result in lack of moisture or wetness in the eye.

In one embodiment, Rho inhibitors, may be administered orally, locally by injection or drops, spray or ointment for alleviating the effects of conditions that result in lack of moisture or wetness in the eye, such as the inflammatory conditions resulting in dry eye including pemphigus and Sjogren's syndrome, which affect the eye by either damaging the conjunctival cells, or by damaging the lacrimal glands of the eye and/or the meibomian glands of the eye lid.

In one embodiment, the required treatment of Rho inhibitors such as Botox in 1-2 units, may be administered locally by injection or drops, spray or ointment or as nano- or microparticles with (alpha)-cyclodextrin, or (beta)-cyclodextrin, or (gamma)-cyclodextrin, hydroxypropyl-b-cyclodextrin (bHPCD for inflammatory processes resulting in dry eye including hypolacrimation, alacrima, xerophthalmia, Stevens-Johnson syndrome, pemphigus, ocular pemphigoid, marginal blepharitis, nerve pain, diabetes, and/or post-corneal surgery after cutting the corneal nerves (including but not limited to post-LASIK surgery or PRK or corneal inlay). Other conditions resulting in dry eye include the aging process, environmental factors (e.g., dry home and/or work environments), and extended use of visual display terminals (e.g., employment, recreation, etc.).

In one embodiment, the required treatment of Rho inhibitors, such as Botox in 1-2 units, may be administered locally by injection or drops, spray or ointment or as nano- or microparticles with (alpha)-cyclodextrin, or (beta)-cyclodextrin, or (gamma)-cyclodextrin, hydroxypropyl-b-cyclodextrin (bHPCD for chronic inflammatory processes, lichen planus, arthritis, psoriasis, and plantar fasciitis.

In one embodiment, inhibition of Wnt signaling or ABC transporters by RNA interference may be a valuable therapeutic strategy in dry eye including hypolacrimation, alacrima, xerophthalmia, and Stevens-Johnson syndrome, pemphigus, where the Wnt inhibitors administered as nano- or microparticles with (alpha)-cyclodextrin, or (beta)-cyclodextrin, or (gamma)-cyclodextrin, hydroxypropyl-b-cyclodextrin (bHPCD).

In one embodiment, a number of Rock inhibitors are used in non-toxic doses in combination with functionalized nanoparticles, conjugated with polymeric coating, such as chitosan, polyanhydride, cyclodextrin as a potent ROCK inhibitor; bioavailable Fasudil hydrochloride, inhibitor of cyclic nucleotide dependent- and Rho-kinases GSK 269962, potent and selective ROCK inhibitor GSK 429286, selective Rho-kinase (ROCK) inhibitor H1152 dihydrochloride, selective Rho-kinase (ROCK) inhibitor Glycyl H 1152 dihydrochloride, selective Rho-kinase (ROCK) inhibitor, more selective analogue of H1152, Cell-permeable, selective Rho-kinase inhibitor OXA 06 dihydrochloride, potent ROCK inhibitor PKI1447 dihydrochloride, potent and selective ROCK inhibitor, antitumor SB 772077B, potent Rho-kinase inhibitor, vasodilator SR 3677 dihydrochloride, potent, selective Rho-kinase (ROCK) inhibitor TC-S7001, potent and highly selective ROCK inhibitor, orally active Y-27632 dihydrochloride and may be dissolved in an organic solvent such as DMSO or alcohol or sterol, lanosterol, squalene, and/or squalamine, or in nano- or microparticles with (alpha)-cyclodextrin, or (beta)-cyclodextrin, or (gamma)-cyclodextrin, or hydroxypropyl-b-cyclodextrin (bHPCD) or containing a polyanhydride, poly(glycolic) acid, poly(lactic) acid, or polycaprolactone polymer to reduce the inflammation processes in the eye, retina, choroid, sclera, lid, conjunctiva, or other mucosal diseases, or in the mouth.

In one embodiment, small molecule Wnt inhibitor PKF118-310, the Wnt/β-catenin pathway inhibitor and Fasudil, a rock inhibitor Fasudil (HA-1077), a selective RhoA/Rho kinase (ROCK) inhibitor, or Y-27632, small molecule inhibitor of ROCK1 and ROCK2, etc. may be dissolved in an organic solvent such as DMSO or alcohol or sterol, lanosterol, squalene, and/or squalamine, or containing a polyanhydride, poly(glycolic) acid, poly(lactic) acid, or as nano- or microparticles with (alpha)-cyclodextrin, or (beta)-cyclodextrin, or (gamma)-cyclodextrin, hydroxypropyl-b-cyclodextrin (bHPCD) or polycaprolactone polymer to release non-toxic medication slowly at desired concentration to the eye.

In one embodiment, early management includes, the use of lubricants, artificial tear substitutes, ointment, gel, or emulsion. Topical anti-inflammatory agents, topical rock inhibitors, anti-interleukin (IL1) TNF-alfa TNF-α, hyaluronic acid, low molecular heparin 0.1-5% solution alone or in combination with, metalloproteinase inhibitors doxycycline 0.1-5% solution immunosuppressive agent or inhibitor mycophenylic acid as local or systemic therapy.

In one embodiment, topical Rock inhibitors are applied to the cornea as drops or spray or subconjunctival injection as a slow release compound combined with chitosans or in nano- or microparticles with (alpha)-cyclodextrin, or (beta)-cyclodextrin, or (gamma)-cyclodextrin, hydroxypropyl-b-cyclodextrin (bHPCD in 0.1 microgram/ml to 40 microgram/ml or more for topical application.

In another embodiment, the Rock inhibitors are coated with the slow release polymers, such as lactic acid and/or glycolic acid at a concentration of 200 nanograms to 1 micrograms/ml or more and administered, topically, subconjunctival or inside the eye subcutaneously inside the plantar fascia in the joint, etc. using nano- or microparticles with (alpha)-cyclodextrin, or (beta)-cyclodextrin, or (gamma)-cyclodextrin, hydroxypropyl-b-cyclodextrin (bHPCD) for slow release and tissue penetration with or without cell penetrating agents.

In another embodiment, the Rock inhibitors are released from a polymeric explant or implant either placed over or under the conjunctiva and sutured to the sclera to release, e.g., Fasudil, etc. at concentrations of 0.01 microgram/ml to 40.0 microgram/ml or more per day.

In one embodiment, the Rock inhibitors release, after placement in the upper or lower cul-de-sack of the conjunctiva or as a slow release punctal plaque or implanted subconjunctivally, at a rate of 1 picogram to a 10 nanograms/day of the medication or delivered as nano- or microparticles with (alpha)-cyclodextrin, or (beta)-cyclodextrin, or (gamma)-cyclodextrin, hydroxypropyl-b-cyclodextrin (bHPCD) injection.

In one embodiment, the Rock inhibitors release, after placement of an implant or as nano- or microparticles with (alpha)-cyclodextrin, or (beta)-cyclodextrin, or (gamma)-cyclodextrin, hydroxypropyl-b-cyclodextrin (bHPCD) in the suprachoroidal space, inside the eye, behind the eye, inside the gingiva, subcutaneously in plantar fascia, or as a slow release polymeric plaque or implanted to release medication at a rate of 1 picogram to a 10 nanograms/day of the non-toxic medication.

In another embodiment, the nanoparticles or dendrimers are conjugated with Rock inhibitors and chitosan delivered as a slow release system that can be released as a temperature sensitive polymer that melts at 42-43 degrees used with a warm compressor over or under the lid, or light thermal application, or the use of a compressive focused ultrasound applied to lid, conjunctiva or cornea or the lid releasing 1 picogram to a 10 nanograms/day of the medication.

In one embodiment, the Rock inhibitors or Wnt inhibitors are delivered as nano- or microparticles with (alpha)-cyclodextrin, or (beta)-cyclodextrin, or (gamma)-cyclodextrin, hydroxypropyl-b-cyclodextrin (bHPCD) with simultaneous application of amniotic membrane and slow release nanoparticles applied post corneal surgery, such as LASIK, or corneal inlay cataract corneal transplant, or cataract surgery and lens implantation or any other corneal surgical intervention, scleritis, retinitis, vitreoretinal surgery, diabetic retinopathy, macular edema, at 10 picograms to 20 nanograms of medication per day.

In one embodiment, the Rock inhibitors or Wnt inhibitors are delivered with simultaneous application of amniotic membrane and low molecular weight heparin slow release nanoparticles applied post corneal surgery, such as LASIK, cataract, or cataract surgery and lens implantation, after retinal surgery, vitreous surgery, corneal transplant uveitis scleritis or chemical injury to the cornea or conjunctiva at concentrations of 0.001 micrograms/ml to 40 micrograms/ml or more or topical or subconjunctival Botox, at 1-100 units or topical at 1-5 units or more in a physiological solution of Botox, or similar preparations.

In one embodiment, the Rock inhibitors or Wnt inhibitors are delivered with simultaneous application of low molecular weight heparin (levonox) with other medications, such as tetracycline, Doxycycline or metalloproteinase inhibitors, dexamethasone 0.1%-1% concentration as slow release polymeric nanoparticles or liposomes applied post corneal surgery such as LASIK, PRK, cataract, corneal transplant, uveitis, scleritis or thermal or chemical injury to the cornea or conjunctiva, e.g., Fasudil derivatives, etc., at 0.1 micrograms/ml to 40 micrograms/ml or more, or Botox at 1-3 units as nano- or microparticles with (alpha)-cyclodextrin, or (beta)-cyclodextrin, or (gamma)-cyclodextrin, hydroxypropyl-b-cyclodextrin (bHPCD) solution or suspension.

In one embodiment, after LASIK or cataract surgery and lens implantation or any refractive surgery or cataract surgery, Rock inhibitors at doses of 0.1 micrograms/ml to 40 micrograms/ml or more for topical application or Wnt inhibitor can be injected as nano- or microparticles with (alpha)-cyclodextrin, or (beta)-cyclodextrin, or (gamma)-cyclodextrin, hydroxypropyl-b-cyclodextrin (bHPCD) in the corneal pocket or in the anterior chamber, or applied as drops in the post-operative period to replace prednisolone or other steroids, or NASIDs, and encourage regrowth of the cut neurons in the cornea.

In one embodiment, after LASIK or any refractive surgery or cataract surgery, Wnt inhibitors or, Rock inhibitors such as botulinum toxin (Botox) can be injected under the conjunctiva or applied as drops in the post-operative period to encourage regrowth of the cut neurons in the cornea after LASIK or other corneal surgery at doses of 1 to 10 units of Botox injected under the conjunctiva or 1-2 drops daily at concentration of 10 picograms to 500 picograms of Botox in physiological solution or topically as drops.

In one embodiment, in dry eye syndrome, Rock inhibitors or Wnt inhibitor, such as botulinum toxin (Botox) can be applied as drops or injected subconjunctivally to eliminate the inflammatory component of dry eye at doses of 1-10 units once a month or once every 2 to 3 months with slow release nanoparticle conjugates in biodegradable polymers or as nano- or microparticles with (alpha)-cyclodextrin, or (beta)-cyclodextrin, or (gamma)-cyclodextrin, hydroxypropyl-b-cyclodextrin (bHPCD).

In one embodiment, in dry eye syndrome, Rock inhibitors such as botulinum toxin (Botox), Fasudil, etc. or Wnt inhibitors, such as niclosamide, nitazoxanide (NTZ), ivermectin, FH535, IWP-2, PNU-74654, IWR-lendo. IWR-exo, Demethoxy Curcumin, sulforaphane as nano- or microparticles with (alpha)-cyclodextrin, or (beta)-cyclodextrin, or (gamma)-cyclodextrin, hydroxypropyl-b-cyclodextrin (bHPCD) and vitamin D can be given orally at the tolerated dose or 40 mg Fasudil or 1 gram niclosamide or 10-100 units of Botox to eliminate the inflammatory component of dry eye, sulforaphane at 400 micrograms and Vitamin D 3000-5000 IU.

In one embodiment, the Rock inhibitors, such as Fasudil derivatives at concentrations or 10 picograms to 10 nanograms to 1 microgram per drop Botox solution of 0.1 units of Botox can be administered with small molecule WNT inhibitors or a low concentration 1-10 micrograms.

In one embodiment, a topical or subconjunctival or intraocular administration of the Rock inhibitors, such as Fasudil derivatives, etc., at concentrations or 10 picograms to 100 nanograms/0.25 ml or Botox solution of 0.1-1 units can be administered with small molecule WNT inhibitors or a low concentration of sulforaphane and vitamin D to inhibit the inflammatory processes or auto-immune response as nano- or microparticles with (alpha)-cyclodextrin, or (beta)-cyclodextrin, or (gamma)-cyclodextrin, hydroxypropyl-b-cyclodextrin (bHPCD).

In one embodiment, Rock inhibitors are administered with antibody coated nanoparticles conjugated with thermo-sensitive nanoparticles and Adalimumab, a humanized antibody administered topically or subcutaneously at a non-toxic dose.

In one embodiment, Rock inhibitors are administered with antibody coated nanoparticles, dendrimers, liposomes, etc. to the conjunctiva as liposomes or ointment in Meibomian gland inflammation to release medication at a concentration of 1 picogram to 100 units or more picograms/ 0.25 ml to 0.5 ml along with an antibiotic with nano- or microparticles with (alpha)-cyclodextrin, or (beta)-cyclodextrin, or (gamma)-cyclodextrin, hydroxypropyl-b-cyclodextrin (bHPCD).

In one embodiment, Wnt inhibitors or Rock inhibitors, such as Fasudil derivatives, etc. are administered with nanoparticles, dendrimers, thermosensitive polymers conjugated with polylactic or polyglycolic acid or chitosan, microspheres, liposomes, dendrimers, microparticles or nanoparticles, or porous silicone implant and combinations thereof, and they are administered as drops, or injected in the conjunctival or lacrimal glands along with immunosuppressive agents, such as mycophenolic acid, etc. as nano- or microparticles with (alpha)-cyclodextrin, or (beta)-cyclodextrin, or (gamma)-cyclodextrin, hydroxypropyl-b-cyclodextrin (bHPCD).

In one embodiment, topical administrations, subconjunctival injections, sub-tenon injections, suprachroideal injections, intravitreal injections can be combined with small molecule Wnt inhibitors or standard anti-inflammatory agents (e.g., steroids, dexamethasone, etc.) depot, nanoparticle implants, biodegradable or non-biodegradable polymers, NASIDs, Diclofenac, immunotherapy immunosuppressants, etc. to treat inflammatory processes of the lid conjunctiva or the cornea and the lid or throughout the day. For injection, a dose of about 50 picograms/ml to about 200 micrograms/ml may be used as a surgical implant, for example, in a diffusible walled reservoir sutured to the wall of the sclera, or may be contained within an inert carrier, such as microspheres dendrimers, or liposomes, porous silicon oxide microparticles or as nano or microparticles with (alpha)-cyclodextrin, or (beta)-cyclodextrin, or (gamma)-cyclodextrin, hydroxypropyl-b-cyclodextrin (bHPCD) to provide a slow-release drug delivery system.

In one embodiment, a formulation of Wnt or Rock inhibitors is used from the group consisting of topical administration at a concentration of about 50 picograms/ml to less than 1 micrograms/ml, subconjunctival injection at a dose in the range of about 1 picogram/ml to about 200 micrograms/ml, intravitreal injection at a dose in the range of about 0.1 picogram/ml to about 20 micrograms/ml, or retrobulbar injection at a dose in the range of about 2 micrograms/ml to about 200 micrograms/ml in slow release microspheres or dendrimers. In one embodiment, a formulation of Wnt or Rock inhibitors is used comprising intraocularly administering to a patient after corneal surgery at picogram to nanogram concentrations or as nano- or microparticles with (alpha)-cyclodextrin, or (beta)-cyclodextrin, or (gamma)-cyclodextrin, hydroxypropyl-b-cyclodextrin (bHPCD) preparation.

In one embodiment, a formulation of Wnt or Rock inhibitors is used as a composition consisting essentially of Rock inhibitors in a pharmaceutically acceptable formulation and in an amount effective to enhance post-surgical to enhance ocular moisture, nerve regeneration in the patient wherein the composition is administered at a concentrations up to about 10 micrograms/ml by at least one of slow release polycaprolactone, polylactic, or polyglycolic acid, etc. over many months, intraocular administration of the composition or is administered topically at a concentration in the range between about 10 picograms/ml to less than 1 microgram/ml depending on the composition of the medication or as nano- or microparticles with (alpha)-cyclodextrin, or (beta)-cyclodextrin, or (gamma)-cyclodextrin, hydroxypropyl-b-cyclodextrin (bHPCD).

In one embodiment, wherein the polymeric composition is administered by subconjunctival injection at a dose in the range of about 1 picogram/ml to about 20 micrograms/ml, intravitreal injection at a dose in the range of about 1 picogram/0.1 ml to about 20 nanograms/ml, or retrobulbar injection at a dose in the range of about 20 nanograms/ml to about 2 micrograms/ml, as nano- or microparticles with (alpha)-cyclodextrin, or (beta)-cyclodextrin, or (gamma)-cyclodextrin, hydroxypropyl-b-cyclodextrin (bHPCD).

In one embodiment, a formulation of Wnt or Rock inhibitors is used to enhance post-surgical ocular moisture or in papillitis, optic nerve neuritis, uveitis, or scleritis in the patient wherein the composition is administered at a concentration up to about 50 picograms/ml by at least one of intraocular injection, or the composition is administered topically at a concentration in the range between about 50 picograms/ml to less than 1 micrograms/ml as nano- or microparticles with (alpha)-cyclodextrin, or (beta)-cyclodextrin, or (gamma)-cyclodextrin, hydroxypropyl-b-cyclodextrin (bHPCD).

In one embodiment, a formulation of Wnt or Rock inhibitors is used wherein the composition is administered by subconjunctival injection at a dose in the range of about 1 picogram/ml to about 2 micrograms/ml, intravitreal injection at a dose in the range of about 1 nanogram/0.1 ml to about 20 nanograms/ml, or retrobulbar injection at a dose in the range of about 200 nanograms/ml to about 2 micrograms/ml as nano- or microparticles with (alpha)-cyclodextrin, or (beta)-cyclodextrin, or (gamma)-cyclodextrin, hydroxypropyl-b-cyclodextrin (bHPCD).

In one embodiment, a method to treat an ocular condition in a patient comprises intraocularly administering to the patient a pharmaceutically acceptable formulation of a drug selected from the group consisting of Rock inhibitors, such Rock inhibitors as Fasudil or derivatives in nanogram to microgram concentrations in microspheres, dendrimers, physiological solution, botulinum toxin in picogram concentrations in polymeric microspheres or 0.3-5 units injectable, or Wnt inhibitors, such as niclosamide, nitazoxanide (NTZ), ivermectin, nanogram to microgram concentration in microspheres, dendrimers, suspension or another polymer, sulforaphane 10-400 nanograms in microspheres, dendrimers, or as nano- or microparticles with (alpha)-cyclodextrin, or (beta)-cyclodextrin, or (gamma)-cyclodextrin, hydroxypropyl-b-cyclodextrin (bHPCD) or another polymer and Vitamin D taken orally in 1000-5000 IU etc., Fasudil derivatives taken orally 1-40 mg, niclosamide orally in 10-500 mg tablets, sulforaphane in capsule 10-40 mg or more ivermectin taken orally 1-400 mg or more and topical formulation as drops, ointment, or gel in a non-toxic formulation for the patient undergo surgery in the eye for refractive errors, diabetic retinopathy, retinal detachment, or after cataract surgery or refractive surgery for the duration until the eye is free of inflammation and has recovered from the surgery.

In one embodiment, non-toxic doses of Rock inhibitors in an amount up to about 1-200 micrograms/ml effective to treat dry eye or another ocular condition selected from diabetic retinopathy, retinitis pigmentosa, or age related macular degeneration without substantial toxicity and at least one Wnt inhibitor or Rock inhibitor, wherein the composition is administered by at least one of intraocular injection at a concentration up to about 2 picograms/ml, or the composition is administered topically at a concentration in the range between about 1 picograms/ml to less than 10 nanograms/ml as nano- or microparticles with (alpha)-cyclodextrin, or (beta)-cyclodextrin, or (gamma)-cyclodextrin, hydroxypropyl-b-cyclodextrin (bHPCD).

In one embodiment, a formulation of Wnt or Rock inhibitors is used as topical administration at a concentration between about 50 picograms/ml to 200 nanograms/ml, subconjunctival injection at a dose in the range of about 1 picograms/ml to about 20 micrograms/ml in slow release polymer, intravitreal injection at a dose in the range of about 1 picogram/0.1 ml to about 2 micrograms/ml, or retrobulbar injection at a dose in the range of about 1 picograms/ml to about 200 nanograms/ml suspension in slow release polymer depending on the composition of the medication as nano- or microparticles with (alpha)-cyclodextrin, or (beta)-cyclodextrin, or (gamma)-cyclodextrin, hydroxypropyl-b-cyclodextrin (bHPCD) preparation.

In one embodiment, a method to treat an ocular condition in a patient by intraocularly administering a pharmaceutically acceptable formulation of Wnt inhibitors or rock inhibitors in an amount effective to treat the condition. The method provides treatment while avoiding systemic administration of systemic medication. In one embodiment, a sustained release pharmaceutically acceptable formulation is implanted intraocularly in polymeric slow release compound having about 20 nanograms to 1 microgram or more of Fasudil to about 0.1 micrograms to 40 micrograms or 1 milligram of Fasudil or other rock inhibitors implanted in or on the eye and may continuously deliver Fasudil for five or more years.

In another embodiment, a concentration up to about 10 or more micrograms of Rock inhibitors is administered intraocularly without substantial toxicity.

In another embodiment. Fasudil derivatives are taken orally 1-40 mg, niclosamide is taken orally in 10-500 mg tablets, sulforaphane is taken orally in capsule 10-40 mg or more, ivermectin is taken orally 1-400 mg or more, and topical formulations may be administered as drops, ointment, gel in a non-toxic formulation.

In another embodiment, Rock inhibitors at a concentration in the range of about 1 picogram/ml (0.0000000001%) to less than 0.1 micrograms/ml (less than 0.001%) is administered topically. In other embodiments, Fasudil or another Rock inhibitor at a concentration in the range of about 1 nanogram/ml to about 200 micrograms/ml is injected under the conjunctiva, or a concentration in the range of about 1 picogram/0.1 ml to about 200 micrograms/ml is injected in the vitreous, or a concentration in the range of about 20 picograms/ml to about 200 nanograms/ml is injected behind the eyeball as nano- or microparticles with (alpha)-cyclodextrin, or (beta)-cyclodextrin, or (gamma)-cyclodextrin, hydroxypropyl-b-cyclodextrin (bHPCD) preparation.

In one embodiment, the Rock inhibitors, such as Fasudil, etc., or Wnt inhibitors, such as niclosamide, are administered as topical or a spray at non-toxic concentrations of 1 picogram/ml to 20 nanograms/ml in a physiological pH balanced, with osmolarity of 310 to prevent and treat, decrease the time of onset, or lessen the severity of a wide variety of diseases such as lichen planus, ocular conditions, such as retinitis pigmentosa, ocular irritation following corneal surgery (e.g., LASIK surgery), age related macular degeneration, diabetic retinopathy, dry eye disease, scleritis, papillitis, and uveitis, scleritis pars planatis, or vogt-koyanagii syndrome.

In one embodiment, the Rock inhibitors, such as Fasudil, etc., or Wnt inhibitors, such as niclosamide, nitazoxanide (NTZ), are administered as topical or a spray at non-toxic concentrations of 1 picogram/ml to 20 nanograms/m or in an ointment or cream or suspension of microspheres and dendrimers in meibomian gland disease as nano or microparticles with (alpha)-cyclodextrin, or (beta)-cyclodextrin, or (gamma)-cyclodextrin, hydroxypropyl-b-cyclodextrin (bHPCD) preparation.

In one embodiment, the Rock inhibitors, such as Botulinum toxins are administered as topical or a spray at non-toxic concentrations of 1 picogram/ml to 1 nanograms in a cream, ointment, suspension of microspheres or dendrimers, etc. for topical application in lichen planus, nerve damage after LASIK or refractive surgery procedures, or diabetes or wrinkle treatment.

In one embodiment, the Rock inhibitors, such as Fasudil 40-80 mg/kg, etc., or Wnt inhibitors, such as niclosamide, 100-500 mg or ivermectin, 250 mg to 2000 mg are administered orally to prevent and treat, decrease the time of onset, or lessen the severity of a wide variety of diseases, such as optic nerve neuritis, papillitis, variety of idiopathic uveitis, scleritis, or ocular conditions, such as retinitis pigmentosa, ocular irritation following corneal surgery (e.g., LASIK surgery), age related macular degeneration, diabetic retinopathy, dry eye disease, papillitis, or uveitis.

In one embodiment, the Rock inhibitors or Wnt inhibitors are administered as topical or a spray at non-toxic concentrations of 1 picogram/ml to 20 nanograms/ml in a physiological pH balanced solution with osmolality of 310 to treat the corneal nerve cuts after LASIK surgery to decrease inflammatory process and encourage fast regrowth of neurons from the cut end of the corneal nerves and enhance corneal sensation recovery time and prevent dry eye formation.

In one embodiment, the Rock inhibitors (40-80 mg/Kg) or Wnt inhibitors are administered orally after LASIK surgery to decrease inflammatory process and to encourage fast regrowth of neurons from the cut end of the corneal nerves and enhance corneal sensation recovery time and prevent dry eye formation.

Another embodiment of the invention is a method to treat ocular conditions including ocular irritation following corneal surgery, conjunctivitis, canaliculitis or schlemm's canal of the eye, iritis, lacrimal and Meibomian glandes are treated with Rock inhibitors, such as Fasudil or its derivatives in nanogram to microgram concentrations in microspheres, dendrimers, physiological solution, Botulinum toxin in picogram concentrations in polymeric microspheres dendrimers, or 0.3-5 unit injectable, or Wnt inhibitors, such as niclosamide, nitazoxanide (NTZ), ivermectin, nanogram to microgram concentration in microspheres suspension or another polymer, sulforaphane 10-400 nanogram in microspheres, dendrimers, or another polymer and Vitamin D taken orally in 1000-5000 IU, etc.

In one embodiment, a sustained release pharmaceutically acceptable formulation is implanted intraocularly. For example, a matrix containing in the range of between about 0.4 to 1 mg Fasudil can last for ten or more years. In another embodiment, a concentration up to about 1 microgram Fasudil or others Rock inhibitors is administered intraocularly, inside the joint in arthritis, or subcutaneously or sub-gingival injection in lichen planus without substantial toxicity as nano- or microparticles with (alpha)-cyclodextrin, or (beta)-cyclodextrin, or (gamma)-cyclodextrin, or hydroxypropyl-b-cyclodextrin (bHPCD).

In another embodiment, Rock inhibitors at a concentration in the range of about 1 nanogram/ml (0.0000001%) to less than 1 microgram/ml (less than 0.0001%) are administered topically. In other embodiments, Fasudil at a concentration in the range of about 1 nanogram/ml to about 20 microgram/ml is injected under the conjunctiva, or a concentration in the range of about 1 nanogram/0.1 ml to about 200 micrograms/ml is injected in the vitreous, or a concentration in the range of about 20 nanograms/ml to about 20 micrograms/ml is injected in a slow release polymer, such as polycaprolactone or polylactic or glycolic, in the vitreous cavity or behind the eyeball or other part of the body as needed.

In another embodiment, Rock inhibitors at a concentration in the range of about 1 nanogram/ml (0.0000001%) to less than 1 microgram/ml (less than 0.0001%) are administered topically. In other embodiments, Fasudil at a concentration in the range of about 1 nanogram/ml to about 20 micrograms/ml is injected under the conjunctiva, or a concentration in the range of about 1 nanogram/0.1 ml to about 200 microgram/ml is injected in the vitreous, or a concentration in the range of about 20 nanogram/ml to about 20 micrograms/ml is injected in a slow release polymer, such as polycaprolactone or polylactic or glycolic, in the vitreous cavity or behind the eyeball in subconjunctival space, or subcutaneously as needed as nano- or microparticles with (alpha)-cyclodextrin, or (beta)-cyclodextrin, or (gamma)-cyclodextrin, hydroxypropyl-b-cyclodextrin (bHPCD) preparation.

In one embodiment, the non-toxic doses of Wnt inhibitors, Rock inhibitors, or Botox, act as an anti-inflammatory agent. The botulinum toxin or botox preparation may be administered topically to the eye or eye lid, forehead skin at 1 pictogram to 1 nanogram concentrations, 1 pictogram to 5 nanogram concentrations, for example, using drops, an ointment, a cream, a gel, a suspension of microsphere, dendrimers, etc. The agent(s) may be formulated with excipients such as methylcellulose, hydroxypropyl methylcellulose, hydroxypropyl cellulose, the LD50s of any naturally occurring botulinum toxin protein is at 1.3 nanograms per kilogram (abbreviated ng/kg). In a 75 kg (165 lbs.) subjects, the LD50 for botulinum toxin would be 97.5 nanograms if injected directly into a vein or artery. 100 unit vials contains 0.75 nanograms=750 picograms of botulinum toxin A in the entire vial.

In one embodiment, a dose of botulinum toxin in 100-2000 picograms will not be toxic if injected subcutaneously, or 750 picograms (100 units) 1-2 times a month will not be toxic. Higher doses can be used with caution and it would be desirable not to exceed these levels to prevent an immune response to the medication.

In one embodiment, a dose of botulinum toxin in 100-2000 picograms will not be toxic if injected subcutaneously, or 750 picograms (100 units) 1-2 times a month will not be toxic. Higher doses can be used with caution and it would be desirable not to exceed these levels to prevent an immune response to the medication.

In one embodiment, the concentrations 1-20 picograms/Botox in a physiological solution, or up to 30 picograms conjugated with antibody coated nanoparticles would be non-toxic to the body or when conjugated with thermosensitive polymeric coating of the nanoparticles in a physiologic solution or used as drops or injectable or as nano- or microparticles with (alpha)-cyclodextrin, or (beta)-cyclodextrin, or (gamma)-cyclodextrin, hydroxypropyl-b-cyclodextrin (bHPCD) preparation.

In one embodiment, the Wnt inhibitors or Rock inhibitors may be injected into the eye, for example, injection under the conjunctiva or tenon capsule, intravitreal injection, or retrobulbar injection as a slow release nanoparticle. The agent(s) may be administered with a slow release drug delivery system, such as polymers, matrices, microcapsules, nanoparticles or microparticles of porous silicone or other delivery systems formulated from, for example, glycolic acid, lactic acid, combinations of glycolic and lactic acid, liposomes, silicone, as nano- or microparticles with (alpha)-cyclodextrin, or (beta)-cyclodextrin, or (gamma)-cyclodextrin, hydroxypropyl-b-cyclodextrin (bHPCD) or polyanhydride polyvinyl acetate alone or in combination with polyethylene glycol, etc. The delivery device can be implanted intraocularly, in the lens capsule, over the lens in the choroid for example, implanted under the conjunctiva, implanted in the wall of the eye, sutured to the sclera, for long-term drug delivery or injected in the vitreous cavity.

In one embodiment, one uses a composition containing Rock inhibitors, such as Fasudil etc., at a concentration in the range of about 50 picogram/ml (0.000000005%) to about 50 micrograms/ml (0.005%), niclosamide at a concentration in the range of about 50 picograms/ml to about 50 micrograms/ml, or a combination of Fasudil or an immune suppressive agent, such as mycophenolic acid, to achieve a total concentration of both agents of about 50 picogram/ml to about 50 microgram/ml as nano- or microparticles with (alpha)-cyclodextrin, or (beta)-cyclodextrin, or (gamma)-cyclodextrin, hydroxypropyl-b-cyclodextrin (bHPCD). Within this range, the agent(s) has wide safety and efficacy, permitting specific doses or administration protocols to be formulated for specific applications. For example, some patients may prefer once a day administration compared to administration more than once a day, so a higher concentration of agent(s) may be used for these patients.

In another embodiment, Rock inhibitors, such as Fasudil may also be administered by injection. Intraocular injection may be desirable or necessary, for example, for conditions in which topical administration is either not advised or is inadequate, for patients who have difficulty self-administering medications, etc. In one embodiment, the volume injected is less than 0.3 ml. In another embodiment, the volume injected is in the range of about 0.01 ml to about 0.3 ml. For intravitreal administration (injection into the vitreous), Rock inhibitor concentrations in the range of about 1 nanogram/0.1 ml to about 20 microgram/ml (0.002%) may be used without toxicity or adverse side effects.

In another embodiment, niclosamide used in amounts ranging from about 1 nanogram to about 10 micrograms is contained in an aqueous-based cream excipient. In another embodiment, the amount of Fasudil, etc. or other Rock inhibitors ranges from about 1 nanogram to about 10 micrograms, and is contained in an aqueous-based cream excipient. In another embodiment, Fasudil and niclosamide or mycophenolic acid are present in an aqueous-based cream excipient in various proportions. In another embodiment, to achieve a total amount of combined agents of about 1 nanogram to about 10 micrograms, the drug(s) may be incorporated directly into the cream in solution, or may be contained in liposomes or microspheres, dendrimers, either in solution or in an anhydrous form as nano- or microparticles with (alpha)-cyclodextrin, or (beta)-cyclodextrin, or (gamma)-cyclodextrin, hydroxypropyl-b-cyclodextrin (bHPCD). The cream formulation is usually applied to the eye at bedtime, but it may be applied any time throughout the day if the cream does not cause blurred vision. In another embodiment, the agent(s) is formulated as a solution or suspension and is applied topically in the form of eye drops.

In another embodiment, for long term delivery of a Rock inhibitor or a Wnt inhibitor, either alone or in combination, and/or for sustained release, a matrix housing or containing the agent(s) may be implanted into the eye. For example, a reservoir containing in the range of about 1 milligram to about 5 milligrams of agent(s) is estimated to be able to release about 1 microgram agent(s) per day. At such a release rate, continuous, sustained dosing may occur over 1000 to 5000 days. If less than 1 microgram of agent(s) per day is released, sustained dosing may last up to or more than a decade. In one embodiment, less than 50 micrograms/day of agent(s) is released from the matrix. In another embodiment, agent(s) is released form the matrix at a rate in the range of about 50 picogram/day to about 50 micrograms/day. In another embodiment, agent(s) is released from the matrix at a rate in the range of about 1 micrograms/day to about 5 micrograms/day.

In another embodiment, a surgically implanted intraocular device or matrix may be provided with a reservoir container having a diffusible wall of polyvinyl alcohol or polyvinyl acetate or polycprolactone and containing milligram quantities of a Rock inhibitor or Wnt inhibitor, or a combination of them may be implanted in the sclera. As another example, milligram quantities of agent(s) may be incorporated into a polymeric matrix having dimensions of about 1 millimeter (mm) by 2 millimeter (mm), and made of a polymer such as polycaprolactone, poly(glycolic) acid, poly(lactic) acid, or a polyanhydride, or a lipid such as sebacic acid, and may be implanted on the sclera or in the eye.

In another embodiment, as one example of an inert matrix, liposomes may be prepared from dipalmitoyl phosphatidylcholine (DPPC), preferably prepared from egg phosphatidylcholine (PC) since this lipid has a low heat transition. Liposomes are made using standard procedures as known to one skilled in the art. The agent(s), in amounts ranging from picogram to microgram quantities, is added to a solution of egg PC, and the lipophilic drug binds to the liposome.

In another embodiment, the implantable formation may be in the form of a capsule of any of the polymers previously disclosed (e.g., polycaprolactone, poly(glycolic) acid, poly (lactic) acid, polyanhydride) or lipids that may be formulated as microspheres or dendrimers. As an illustrative example, Fasudil may be mixed with polyvinyl alcohol (PVA), the mixture then dried and coated with ethylene vinyl acetate, then cooled again with PVA. Niclosamide bound with liposomes may be applied topically, either in the form of drops or as an aqueous based cream, or may be injected intraocularly as nano or microparticles with (alpha)-cyclodextrin, or (beta)-cyclodextrin, or (gamma)-cyclodextrin, hydroxypropyl-b-cyclodextrin (bHPCD). In a formulation for topical application, the drug is slowly released over time as the liposome capsule degrades due to wear and tear from the eye surface. In a formulation for intraocular injection, the liposome capsule degrades due to cellular digestion, other slow release polymers such as PLA, PGA, Polycaprolactone, microsphere, dendrimers) or as nano- or microparticles with (alpha)-cyclodextrin, or (beta)-cyclodextrin, or (gamma)-cyclodextrin, hydroxypropyl-b-cyclodextrin (bHPCD) are also utilized.

In another embodiment, the time-release administration, however, is formulated so that the concentration released at any period of time does not exceed a toxic amount. This is accomplished, for example, through various formulations of the vehicle (coated or uncoated microspheres, coated or uncoated capsule, lipids, dendrimers, or polymer components, unilamellar or multilamellar structure, and combinations of the above, etc.). Other variables may include the patient's pharmacokinetic-pharmacodynamic parameters (e.g., body mass, gender, plasma clearance rate, hepatic function, etc.). The formation and loading of microspheres, dendrimers, microcapsules, liposomes, etc. and their ocular implantation are standard techniques known by one skilled in the art.

In one embodiment, Rock inhibitors, such as Fasudil, or Botox, etc. or Wnt inhibitors such as niclosamide, alone or in combination with low molecular weight heparin and metalloproteinase inhibitors, such as doxycycline, tetracycline, etc. can be used at non-toxic concentrations with or without dexamethasone, for dry eye or lichen planus or pemphigus or Stevens-Johnson syndrome, lesions of the mucosa, or skin or other inflammatory diseases of the retina, cornea, conjunctival sclera or optic nerve neuritis, scleritis, uveitis in an appropriate physiological solution or ointment, as nano- or microparticles with (alpha)-cyclodextrin, or (beta)-cyclodextrin, or (gamma)-cyclodextrin, hydroxypropyl-b-cyclodextrin (bHPCD), etc.

In one embodiment, the intravenous solution form of Rock inhibitors or Wnt inhibitors may be diluted to achieve the indicated concentration using 0.9% NaCl or 5% dextrose, or an organic solvent such as dimethyl sulfoxide (DMSO) or sterol, lanosterol, squalene, and/or squalamine. Intraocular administration may be any of the routes and formulations previously described. For injection, either a solution, emulsion, suspension of a liquid, capsular formulation of microspheres, dendrimers, or liposomes, as nano- or microparticles with (alpha)-cyclodextrin, or (beta)-cyclodextrin, or (gamma)-cyclodextrin, hydroxypropyl-b-cyclodextrin (bHPCD), etc. may be used.

In one embodiment, Rock inhibitors or Wnt inhibitors or Botox may be injected subconjunctivally to treat uveitis at a dose in the range of about 1 picogram/ml to about 200 picograms/ml, or intravitreally at a dose of about 1 gram/0.1 ml to about 200 picograms/ml. In one embodiment, the dose is about 50 picograms/0.1 ml. To treat scleritis involving the anterior sclera, Rock inhibitors or Wnt inhibitors or Botox may be administered topically as nano- or microparticles with (alpha)-cyclodextrin, or (beta)-cyclodextrin, or (gamma)-cyclodextrin, or hydroxypropyl-b-cyclodextrin (bHPCD).

In one embodiment, Rock inhibitors or Wnt inhibitors or Botox may be injected to treat scleritis involving the posterior sclera, may be administered by retrobulbar injection at a dose in the range of about 20 picogram/ml to about 800 picograms/ml or more and dissolved in DMSO or a very low concentration of alcohol or sterol, lanosterol, squalene, and/or squalamine.

In one embodiment, to treat neuritis or papillitis, Rock inhibitors may be administered by retrobulbar injection at a dose in the range of about 200 picogram/ml to about 800 nanograms/ml of Fasudil and its derivatives, etc.

In one embodiment, to treat neuritis or papillitis, Rock inhibitors (e.g., Fasudil) may be administered orally at a dose in the range of about 40-80 milligrams of Fasudil tablets, etc. or one time niclosamide 1-2 grams orally.

In one embodiment, the ocular solutions contain at least one Rock inhibitor or Wnt inhibitor such as sulforaphane and provide anti-inflammatory, anti-cell proliferation, anti-cell migration effects if given orally with Vitamin D, topically as dendrimer or microsphere delivery or an injectable non-toxic preparation.

In one embodiment, the solution or suspension is administered intraocularly after cataract surgery before insertion of a replacement intraocular lens, resulting in reduced postoperative inflammation, which may eliminate the need for a steroid therapy.

In one embodiment, the solution may be one that is invasively administered, for example, an irrigation or volume replacement solution containing at least one Rock inhibitor, such as Botox, or Wnt inhibitor.

In one embodiment, the solution may be one that is non-invasively or topically administered in the form of drops, ointments, gels, creams, etc. and may include eye lubricants and contact lens solutions. The solution may contain a supratherapeutic concentration of agent(s), such as 40 microgram/ml or to 80 micrograms/ml or more for topical application ranges 40 nanograms/ml to 4 micrograms/ml Fasudil and its derivatives, etc. as nano- or microparticles with (alpha)-cyclodextrin, or (beta)-cyclodextrin, or (gamma)-cyclodextrin, hydroxypropyl-b-cyclodextrin (bHPCD) so that a therapeutic concentration of a topically administered solution accumulates in a diseased ocular structure sufficient to treat the disease.

In one embodiment, medications are administered with antibody coated nanoparticles, dendrimers, or as nano or microparticles with (alpha)-cyclodextrin, or (beta)-cyclodextrin, or (gamma)-cyclodextrin, hydroxypropyl-b-cyclodextrin (bHPCD), thermosensitive polymers, nanoparticles, dendrimers, lactic or glycolic acid, chitosan or combinations, etc. Immunosuppressives are all conjugated with the antibody coated nanoparticles for slow release as topical drops or an injectable preparation for dry eye after LASIK, meibomian gland inflammation, optic nerve neuritis, uveitis, scleritis, etc.

In one embodiment, Rock inhibitor or Wnt inhibitors are administered by topical drops, spray, subconjunctival injection, subtenon injection, suprachroideal injection, intravitreal injection in combination with standard anti-inflammatory agents etc. and steroids, dexamethasone, etc. as depot, nanoparticles implant biodegradable or non-biodegradable polymers.

In one embodiment, a method of using Rock inhibitors or Wnt inhibitors is disclosed where Rock inhibitors or Wnt inhibitors are administered at non-toxic doses to the skin or mucosa.

In one embodiment, in treating lichen planus, for example, a topical administration may contain between about 10 picogram/ml drug to about 50 micrograms/ml of Fasudil, etc. or other Rock inhibitors in a formulation which may be applied at bedtime or throughout the day or as an injection, a dose of about 50 picograms/ml to about 200 micrograms/ml around or inside the lesion. In one embodiment, the medication may be used as a surgical implant, for example, in a diffusible walled reservoir sutured to the surrounding tissue, or may be contained within an inert carrier, such as microspheres, dendrimers, or liposomes, microparticles or nanoparticles, or porous silicone implant to provide a slow-release drug delivery system to release the medication at 1 picogram to 100 picograms (e.g., Fasudil, etc.) per day.

In one embodiment, a formulation of Wnt or Rock inhibitors is used to treat ocular conditions, such as dry eye disease, as well as other conditions, is disclosed. Rock inhibitors and Wnt inhibitors are used as s topical drop spray application or injection into the eye, or implantation in or on the eye. For example, a topical administration may contain between about 10 picograms/ml drug to about 50 micrograms/ml drug in a formulation which may be applied at bedtime.

In one embodiment, the patient is administered with Rock inhibitors or Wnt inhibitors as nano- or microparticles with (alpha)-cyclodextrin, or (beta)-cyclodextrin, or (gamma)-cyclodextrin, hydroxypropyl-b-cyclodextrin (bHPCD), microparticles or nanoparticles, or porous silicone implant alone or in combination with NSAIDs or to treat associated chronic pain, with more or less inflammatory processes as seen in the eye after refractive surgery or vitreoretinal surgery or ocular hypotony caused either by surgery and associated systemic disease such as diabetes or autoimmune uveitis.

In one embodiment, non-toxic doses of Rock inhibitors, such as Fasudil, etc., 200 picograms to 2 nanograms or as Botox (10-100 units) are administered locally at multiple locations in treatment or pain or chronic inflammation.

In one embodiment, an intrastromal corneal implant is prepared for implantation inside a patient's corneal stroma, and is comprised of an organic stroma, a synthetic 3-D printed corneal stroma, a hybrid polymeric/organic stroma, a genetically modified animal cornea stroma, an eye bank corneal stroma, or tissue culture grown corneal stroma, which are made non-immunogenic to the host cornea by cross-linking the intrastromal corneal implant with riboflavin solution and UV radiation.

In one embodiment, after the enucleated eyes are obtained from the cornea bank, the eyes are dipped in povidone-iodine to sterilize the surface of the tissue, rinsed with saline solution, and then, using a Q-tipped applicator dipped in a saline solution. The corneal epithelium is removed from the donor cornea, then a standard 6-7 mm circular trephine cuts though the remaining cornea and a circular remaining corneal tissue is removed from the eye, cleansed again and the endothelial cells of the cornea are removed while leaving the corneal stromal with its cells.

In one embodiment, using a femtosecond laser or microkeratome, a circular piece of the donor corneal stroma is cut with the thickness of 50, 100, or 150 microns or more thickness that serves for correcting the refractive error of the human recipient cornea from <+1.00 D to +15 D or <−1.00 D to −15.00 power and up to ±6.00 D power of astigmatism including lower and higher order of aberrations.

In one embodiment, the donor stromal inlay is sterilized by dipping it in a solution of 0.1-5% photosensitizer or riboflavin, or riboflavin nanoparticles conjugated with cell penetrating peptides (CPP) or activatable cell penetrating peptides (ACPP) to penetrate the entire stromal block. In one embodiment, the riboflavin solution contains other medications such as NSAIDS, Rock inhibitors, Wnt inhibitors, integrin inhibitors or GSK inhibitors in a polymeric slow release polylactic, glycolic, polycaprolactone, micelles, porous silicon, etc. to release for 3-4 weeks or more. In one embodiment, the riboflavin has the osmolarity of about 300 mOsmol, pH of about 7, with or without dextran or low molecular heparin or hyaluronic acid, and polymeric nanoparticles.

In one embodiment, the corneal inlay containing riboflavin is irradiated with the UV light of a laser with the wavelength of 350-390 nm with a power of 3-30 milliW/cm2 for a period of 1-10 minutes or more to cross-link the inlay by a combination effect of riboflavin and UV radiation creating singlet oxygen and reactive species that cross-link proteins making the inlay non-immunogenic regardless of its origin, such as human or animal of genetically modified animals, such as pig for organ transplant, etc., and the cross-linking simultaneously sterilizes the implant by killing all the potentially existing pathogens.

Figures 54A, 54B:
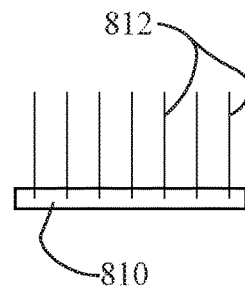
FIG. 54A is a front view of a corneal inlay or implant.
FIG. 54B is a side view of the corneal inlay or implant of FIG. 54A illustrating the formation of small holes in the inlay or implant made using a laser.
Figures 55, 56:
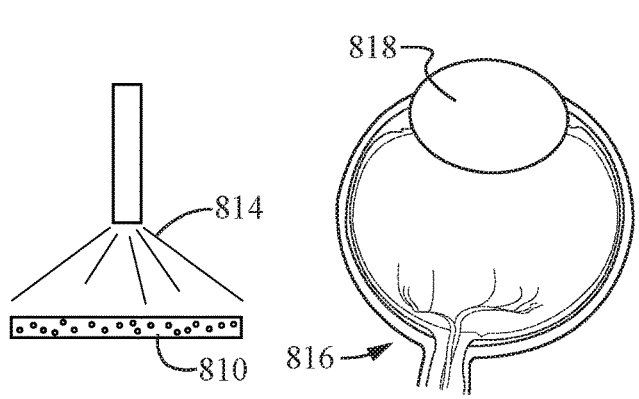
FIG. 55 is a side view of the corneal inlay or implant of FIG. 54A illustrating the cross-linking of the inlay or implant using ultraviolet radiation after the inlay or implant has been soaked in a photosensitizer solution.
FIG. 56 is a cutaway perspective view of an eye before a corneal flap has been formed in the eye.

In one embodiment, the implant is made more permeable to a riboflavin solution by applying femtosecond laser pulses to it (see FIGS. 54A and 54B), then cross-linking by a combination effect of riboflavin and UV radiation (see FIG. 55) creating singlet oxygen and reactive species that cross-link proteins making the inlay non-immunogenic and simultaneously sterilizing the implant by killing all the potentially existing pathogens. The femtosecond laser will create some air bubbles initially, which rapidly dissipate in the air, and do not change the thickness of the inlay. As shown in FIGS. 54A and 54B, small cavities or holes may be formed in the corneal inlay or implant 810 using a femtosecond laser (i.e., the small cavities or holes are formed in the corneal inlay or implant 810 using the laser beam(s) 812 emitted from the femtosecond laser) so as to make the corneal inlay or implant 810 more permeable to a photosensitizer solution (e.g., riboflavin solution), thereby allowing more of the photosensitizer solution to get inside the corneal inlay or implant 810. In the illustrative embodiment, the corneal inlay or implant 810 of FIGS. 54A and 54B is formed from a donor human cornea, and has an outside diameter between 6 and 7 millimeters. As shown in FIG. 55, after the corneal inlay or implant 810 has been soaked in the photosensitizer solution (e.g., the riboflavin solution), the corneal inlay or implant 810 is irradiated using ultraviolet (UV) radiation 814 so as to cross-link the corneal inlay or implant 810. The photosensitizer solution (e.g., the riboflavin solution) in which the corneal inlay or implant 810 is soaked may also contain one or more medications for treating the recipient eye of the patient (e.g., one or more medications described above, such as Rock inhibitors, Wnt inhibitors, integrin inhibitors, GSK inhibitors, etc.).

In another embodiment, the donor cornea, genetically modified cornea, or humanized cornea is prepared by removing it from the donor eye using a 6 to 8 millimeter diameter trephine and scissors to separate it from the eye. The corneal epithelium and endothelium is removed chemically, mechanically, or combination thereof using a Q-tipped applicator dipped either in saline or a solution of 1% or more in water or saline solution and subsequently rinsed immediately with saline to remove the remaining alcohol and/or the loose cells to create a corneal stromal tissue by using a standard femtosecond laser or a mechanical microkeratome to create two or three stromal implant circles of about 100-150 microns in thickness (e.g., see FIG. 61A), when exposed to a solution of 1-5% riboflavin nanoparticles and cell penetrating peptides (CPP), and if needed, an appropriate medication and/or another photosensitizer to cross-link the implant rapidly in less than 3 minutes. Then, the implant is radiated using either a laser with UV radiation of wavelength of between 380 nm to 390 nm, or other wavelength when another photosensitizer rather than riboflavin is used, thereby crosslinking the corneal proteins, including collagen, elastin, etc., and stiffening the corneal collagen and simultaneously killing corneal stromal cells and all pathogens present in the implant and making the implant non-immunogenic without affecting its transparency.

In another embodiment, a 3-D printed cornea is prepared without having the epithelial cells or the endothelial cells, or having only the stromal fibrils, and other proteins, such as collagen and elastin, etc. and mesenchymal stem cells to create a corneal stromal tissue, and by using a standard femtosecond laser or a mechanical microkeratome, create two or three stromal implant circles of about 100-150 microns in thickness, exposed to a solution of 1-5% riboflavin or riboflavin nanoparticles and cell penetrating peptides (CPP) or another photosensitizer to cross-link the implant rapidly in less than 3 minutes. Then, the implant is radiated using a laser with UV radiation of wavelength of 380 nm to 390 nm, a power or 3 milliW/cm2 to 10 milliW/cm2 or more for a time of 1-10 minutes as needed for cross-linking the corneal proteins, including collagen, elastin, etc. to stiffen the corneal collagen and simultaneously kill corneal stromal cells and all pathogens if present in the implant, and make the implant non-immunogenic by cross-linking it, without affecting its transparency.

In one embodiment, the implant is modified to be able to pass through a small incision so as to be placed with an instrument under a flap of the cornea, such as after a LASIK procedure or a procedure that does not require a large corneal incision cutting more corneal nerves. By inserting the implant through a small incision into a stromal pocket, the potential side effects of corneal anesthesia and dry eye are prevented, such as in the small incision lenticule extraction (SMILE) procedure. However in the SMILE procedure, the removed stromal lenticule requires scratching the bordering stroma to the explant, the previously cut stromal lenticule with femtosecond laser inside the stroma for correction of low myopia. However in this typical SMILE procedure, the removed tissue (stromal lenticule) is not replaced with an appropriate lenticule, which would provide a smooth border and shape that reduces or prevents the post-operative glare experienced by majority of the patients.

In one embodiment, in the SMILE procedure, the stromal pocket is not left empty, but is filled with a small porous human corneal, cross-linked implant with an appropriate size and shape to achieve the required refractive correction, while preventing the post-operative glare in this patient.

In one embodiment, the surrounding tissue of the inlay is also cross-linked when the implant has some crosslinker in it, wherein the cross-linker diffuses out of the implant and penetrates the surrounding tissue when the eye is exposed to an external UV radiation for a short period of time after implantation.

In one embodiment, the inlay is placed after a LASIK flap is prepared, and the refractive error of the eye regardless of being myopic, hyperopic, astigmatic, or having any other combined refractive errors, is corrected using a standard excimer laser equipped with wavefront technology and Shack-Hartmann wavefront sensor during in vivo surgery objectively and corrected with the excimer laser immediately, then the corneal flap is repositioned, and the appropriate antibiotic and other medications are applied to the eye.

Figure 57:
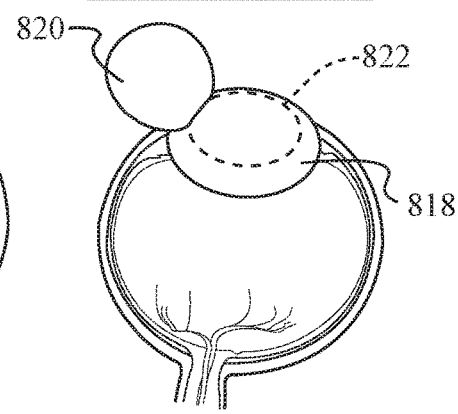
FIG. 57 is another cutaway perspective view of the eye of FIG. 56 illustrating the formation of a corneal flap in the eye using a laser.
Figure 58:
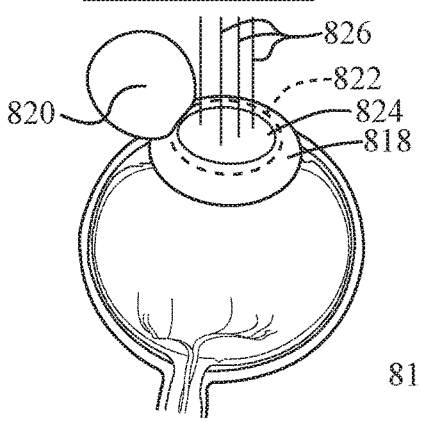
FIG. 58 is yet another cutaway perspective view of the eye of FIG. 56 illustrating the insertion of a corneal inlay under the flap of the eye, wherein corneal inlay is undergoing refractive correction.
Figure 59:
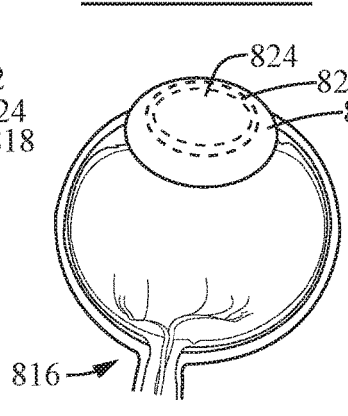
FIG. 59 is still another cutaway perspective view of the eye of FIG. 56 illustrating the eye after the corneal flap has been replaced.
Figure 60:
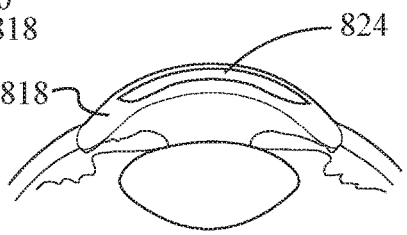
FIG. 60 is a partial side cross-sectional view of the eye of FIG. 56 illustrating the corneal inlay surrounded by the stromal tissue of the cornea.

In one or more embodiments, referring to FIGS. 56-59, a LASIK flap 820 is formed in a cornea 818 of an eye 816 using a femtosecond laser cut 822 (see FIG. 57). Then, a corneal inlay or implant 824 is inserted under the flap 820. The inlay or implant 824 is cross-linked so as to prevent an immune response to the implant and/or rejection of the implant 824 by the patient. Then, as shown in FIG. 58, laser energy 826 is applied to the implant 824 in the eye using an excimer laser so as to modify the refractive power of the implant 824 while being monitored using a Shack-Hartmann wavefront system so as to achieve a desired refractive power for the implant. Finally, as shown in FIG. 59 the cross-linked implant 824 is covered with the flap 820, the cross-linked implant being surrounded entirely by the stromal tissue of the cornea.

In one embodiment, the stromal inlay is a single piece and does not have any curvature to correct the refractive error and as such it is "refractively" neutral with an index of refraction of the normal cornea of 1.33 which similar to the water inside the stroma, and the inlay does not change the refractive power of the cornea, but can increase the thickness of the cornea. In one embodiment, a larger diameter inlay of 8 to 12 mm in diameter and a thickness of 50 to 150 microns can be used in a patient with keratoconus to prevent corneal ectasia or in a patient who has ectasia after refractive surgery, or in combination with photo-therapeutic keratectomy, or as LASIK where the inlay is ablated with an excimer laser to correct the refractive power of the eye. This could be a one step or two step procedure after the initial healing has taken place.

In one embodiment, the implant is used in two different procedures. In one embodiment, in a LASIK procedure, the implant is positioned over the exposed corneal stromal surface after creating a cornea stromal flap, and after ablation the inlay corrects the refractive error of the eye by using an excimer laser and wavefront technology that controls the degree and shape of the tissue removed from the inlay during the surgery to eliminate refractive errors of each eye individually during the surgery, then the corneal stromal flap is returned back over the reshaped anterior surface of the inlay and ultimately the reshaped inlay is surrounded on all sides by the corneal stroma and away from the host's Bowman's membrane or corneal epithelium.

Figure 62:
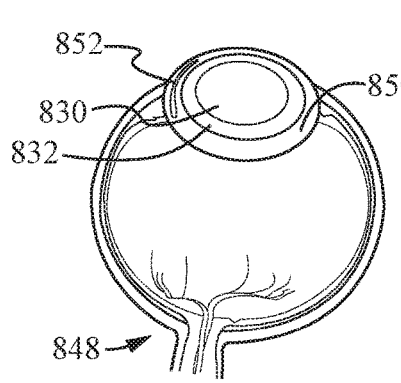
FIG. 62 is a cutaway perspective view of an eye illustrating the cornea of the eye after the two-piece inlay or implant of FIG. 61A has been inserted into a pocket in the cornea through a small incision.
Figure 63:
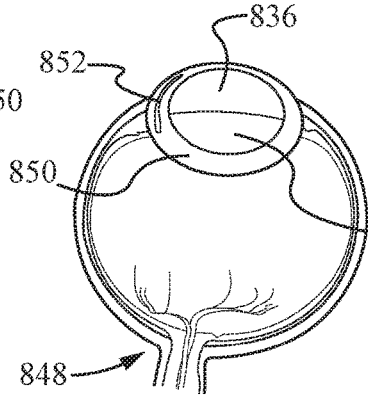
FIG. 63 is a cutaway perspective view of an eye illustrating the cornea of the eye after the two-piece inlay or implant of FIG. 61B has been inserted into a pocket in the cornea through a small incision.
Figure 64:
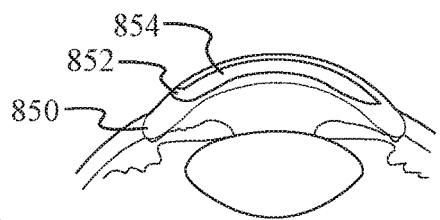
FIG. 64 is a partial side cross-sectional view of the eye of FIGS. 62 and 63 illustrating the cavity of the corneal pocket that is surrounded by stromal tissue.
Figure 65:
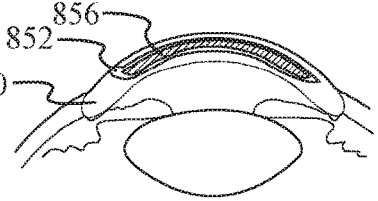
FIG. 65 is a partial side cross-sectional view of the eye of FIGS. 62 and 63 illustrating an inlay or implant that is disposed in the corneal pocket.

In another embodiment, a small incision 852 (e.g., an incision having length of between 4 and 5 millimeters) is created in the cornea 850 of the eye 848 for inlay implantation inside the cornea 850. Initially a 3-D cavity is created inside the corneal stroma with a femtosecond laser, and through the small incision 852 the folded pieces of the inlay 830, 832 or 836, 838, or preferably a composite lens, are implanted inside the stromal cavity as shown in FIGS. 62 and 63. A side cross-sectional view of the stromal cavity 854 of the cornea 850 is shown in FIG. 64, while an implant or inlay 856 is shown disposed in the cavity 854 of the cornea 850 in FIG. 65.

Figure 61A:
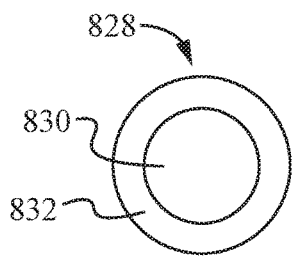
FIG. 61A is a front view of a composite two-piece inlay or implant with a central section and a peripheral section.
Figure 61B:
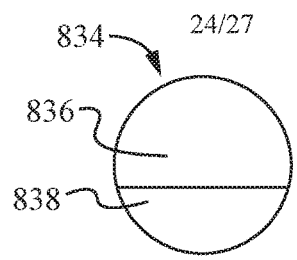
FIG. 61B is a front view of another composite two-piece inlay or implant that is divided transversely into two sections.
Figure 61C:
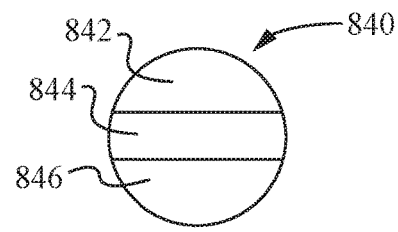
FIG. 61C is a front view of a composite three-piece inlay or implant that is divided transversely into three sections.

A first exemplary composite inlay or implant 828 is illustrated in FIG. 61A. The composite two-piece inlay or implant 828 in FIG. 61A comprises a central portion 830 and a peripheral portion 832. A second exemplary composite inlay or implant 834 is illustrated in FIG. 61B. The composite two-piece inlay or implant 834 in FIG. 61B is transversely divided into two pieces, and comprises a first section 836 and a second section 838. A third exemplary composite inlay or implant 840 is illustrated in FIG. 61C. The composite three-piece inlay or implant 840 in FIG. 61C is transversely divided into three pieces, and comprises a first section 842, a second section 844, and a third section 846.

In one embodiment, the implant or inlay is reshaped prior to implantation inside a 3-D pocket made with a femtosecond laser inside the corneal stroma, with or without the removing of the stromal tissue, e.g., after removal of a part of the scarred stromal tissue or a stromal lenticule, as performed in known SMILE procedure, to fill the cavity with an implant which has a smooth surface and appropriate refraction matching the needed refraction of the eye, using an excimer laser to ablate the surface of the inlay. In one embodiment, the implant or inlay is folded and implanted inside the corneal stromal cavity. In another embodiment, after correcting the inlay to compensate for the refractive error of the patient's eye by using an excimer laser and wavefront technology, the inlay is cut into various pieces and shapes, thus permitting the pieces of the inlay to be implanted inside the stromal cavity through a small incision (e.g., an incision having length of between 4 and 5 millimeters), and simultaneously eliminating the often seen significant glare after the SMILE procedure that lasts about one month or more. The SMILE surgery involves cutting a small 3-D lenticule inside the corneal stroma with a femtosecond laser, then digging out this lenticule with the help of a bent-tipped needle shaped like a hook, but because the femtosecond laser does not completely separates the lenticule from the rest of the stroma, many attempts are done to separate the lenticule from the stroma in a space where there is almost no room for manipulation, thus many scratches are created in the wall of the cavity, which is left to itself to heal. These surface irregularities with bits of the pieces of the left over stromal tissue refract the incoming light and produce glare in extreme situations like scratched on or inside the reading glasses, etc. However, after a month or more, gradually the tissue heals and the glare is reduced or eliminated.

In one embodiment, the post-operative glare can be significantly reduced by implanting a thin non-refracting one-piece inlay or a composite inlay inside the cavity left in the stroma after SMILE procedure where the inlay has a very smooth surface.

In one embodiment, after the SMILE procedure, the stromal cavity can be injected with riboflavin and the excess solution removed immediately by exerting a minor pressure on the cornea to empty the cavity through the small incision in the cornea, the cornea is radiated for about 1-5 minutes with UV radiation to cross-link the wall of the cavity. In one embodiment, after the SMILE procedure, a cross-linker is mixed with a very dilute collagen, or elastin, or just a saline solution to wash out the cavity and immediately removed under mild pressure to cross-link the area so that the stroma with UV radiation heals and strengthens the corneal resiliency despite removal of a part of the corneal stroma.

In another embodiment, composite lenses of implants are used to simplify insertion of the implant through a small incision 852 (see FIGS. 62 and 63) using forceps with the folded pieces of the inlay and a lubricating agent, such as low molecular weight heparin or hyaluronic acid, and then open the inlay with a tiny plastic rod inside the corneal cavity.

In one embodiment, the composite lenses are inserted in the stromal cavity with ease using each piece separately then joining the pieces inside the stromal cavity with or without lubricating agents. Because these lenses are organic and/or formed from a human corneal stroma, they join easily together and the smooth cut edges heal easily without producing significant glare in the post-operative period.

In another embodiment, the implant is a hybrid lens made from partially human cross-linked corneal tissue supported by a more resilient polymeric coating such as polyethylene glycol (PEG), chitosan, or another polymer etc. that is water permeable while providing more resiliency to the implant and keeps the inlay surfaces smooth and easy to implant them through a small incision.

Figure 66:
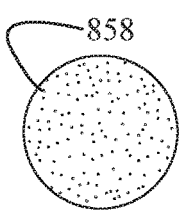
FIG. 66 is a front view of a cross-linked corneal implant or inlay.
Figure 67:
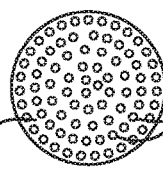
FIG. 67 is a front view of a polymeric back sheet used for supporting the corneal implant or inlay of FIG. 66.
Figure 68:
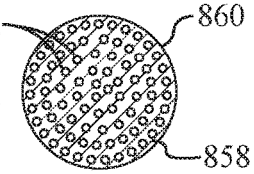
FIG. 68 is a front view illustrating the corneal implant or inlay of FIG. 66 disposed on the polymeric back sheet of FIG. 67.
Figure 69A:
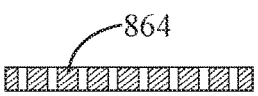
FIG. 69A is a side view of a polymeric back sheet used for supporting a corneal implant or inlay that has a flat surface.
Figure 69B:
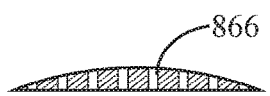
FIG. 69B is a side view of a polymeric back sheet used for supporting a corneal implant or inlay that has a convex surface.
Figure 69C:
FIG. 69C is a side view of a polymeric back sheet used for supporting a corneal implant or inlay that has a concave surface.

In another embodiment, a ribbed, perforated, or sieved polymeric structure (see FIGS. 66-69C) provides support to the overlaying human cross-linked cornea, which drapes over the polymeric structure during the implantation thereof, while the polymeric structure does not prevent the free flow of the fluid from the back of the cornea to the anterior part of the cornea and the holes in this polymeric structure are filled by the surrounding tissue and mostly the fluid in the cornea. Initially, with collective reference to FIGS. 66-68, the cross-linked donor corneal implant or inlay 858 depicted in FIG. 66 may be placed on the polymeric inlay back support structure 860 of FIG. 67 to form the hybrid lens implant depicted in FIG. 68. As shown in FIGS. 67 and 68, the polymeric inlay back support structure 860 is provided with a plurality of tiny holes 862 (e.g., having a diameter of 20 microns to 1 millimeter) disposed therethrough to enable free flow of the fluid from the back of the cornea to the anterior part of the cornea and the holes in this polymeric structure. In the illustrative embodiment, the organic cross-linked corneal implant 858 (e.g., formed from donor corneal tissue) has flat parallel anterior and posterior surfaces, but the shape of the organic cross-linked corneal implant 858 can be modified using a specially-shaped polymeric back support structure. For example, as shown in FIGS. 69A-69C, the polymeric back support structure may have a flat structure 864 (see FIG. 69A) for maintaining the flat shape of the organic cross-linked corneal implant 858, a convex structure 866 (see FIG. 69B) for giving the organic cross-linked corneal implant 858 a convex shape, or a concave structure 868 (see FIG. 69C) for giving the organic cross-linked corneal implant 858 a concave shape. Also, these thin-walled transparent polymeric structures can have an index of refraction similar to the cornea (e.g., 1.3).

In one embodiment, the polymeric supporting elements are made from hydrogel with a very high water content between 50-90% of water. This hybrid implant can be used after a LASIK procedure or small incision intrastromal inlay implantation, the structure can remain in place or removed from the eye by forceps.

In one embodiment, all implants used in conjunction with a LASIK procedure have no refractive surfaces initially, except for an index of refraction which is exactly as the corneal tissue, but after positioning over the exposed corneal stroma and modification of its surface with an excimer laser and wavefront technology to correct all refractive errors only the anterior surface of the inlay is changed during the refractive surgery in vivo, before the corneal flap is repositioned over the inlay. This in vivo correction of refractive error has the advantage that the position of inlay over the corneal stroma does not change after the surgery, since the inlay remains in place all the time during the excimer laser ablation and the flap prevents its motion postoperatively, that is why one can achieve very high satisfaction after LASIK surgery to >98% of the patients. Therefore, there will not be misplacement of the direction of the corrected astigmatism postoperatively which can happen if the inlay surface(s) were corrected ex vivo, and then moved on the cornea or inside in the corneal stroma.

In one embodiment, the crosslinker can be any cross-linker, but preferably it is riboflavin which is excited by UV radiation of 350-390 nm or a 370 nm to 390 nm laser wavelength which crosslinks all the proteins present in the implant including the potential pathogens including viral, bacterial, fungal and parasitic ones.

In one embodiment, the crosslinker is in a nanoparticle form conjugated with cell penetrating peptides (CPP) that penetrate all cellular membranes and cross-link the intercellular proteins eliminating the cells of the human corneal inlay, thus preventing an immune response from the tissue surrounding the inlay that can incite an antigenic response toward a corneal transplant.

In one embodiment, the combination of a riboflavin nanoparticle solution with CPP and an antibiotic, antiviral, antifungal, or anti-parasitic medication is used as topical drops applied to the cornea, then irradiated with UV light to cross-link the infected part of the cornea, so as to kill the pathogens and treat the infectious keratitis.

In one embodiment, all implants are prepared as described, but after implantation of the inlay, the riboflavin is injected in the corneal stromal cavity with a fine needle so that the riboflavin penetrates the wall of the stromal cavity around the implant for a distance of at least 20 microns deep on each side that is cross-linked after termination of the surgery with external UV radiation for short period of time or 1-5 minutes without crosslinking any other part of anterior or posterior stroma not exposed to the riboflavin. The crosslinking of the wall of the cavity kills the stromal cells in that area and creates an immune privileged cavity that prevents an immune response to the implant, the in short situ cross-linking kills potential pathogen that may have contaminated the inlay during the transport.

In one embodiment, medication is present in the riboflavin solution, and the riboflavin nanoparticle solution, and the solution contains free or polymeric slow release nanoparticles of an anti-inflammatory agents such as NSAIDs, Rock inhibitors such as Fasudil, netarsudil, SAR407899, botulinum toxin at 1-10 international units, etc., anti-integrins, resiteganib, Natalizumab at microgram/ml, MLN-00002, Firategrast, IVL745, antagonists of $\alpha v\beta 3$ and/or $\alpha v\beta 5$ integrins, LM609, Vitaxin, Abegrin, CNTO95, Cilengitide etc wnt inhibitors such as Ant1.4Br/Ant 1.4Cl, ivermectin, niclosamide, apicularen and bafilomycin, XAV939, XAV939, G007-LK and G244-LM, NSC668036, SB-216763, gemtuzumab, GSK inhibitors, such as SB-216763, etc., anti-VGEF avastin, lucentis, bevacizumab, afilbercept, antibiotic moxiflacin etc., or antivirals, valcyclovir etc. antifungal amphotericin B, voricanozole or anti-parasitic agents, such as niclosamide, ivermectin, etc. at non-toxic concentrations alone or in combination. These compounds particularly Rock inhibitors and GSK inhibitors encourage sprouting of the cut corneal nerves and regeneration of nerves, and also can be used in combination with nerve growth factors and Brimonidine as topical or slow release polymeric implants, incorporated in the inlay or placed as polymeric implant, in the anterior chamber of the eye, in the vitreous cavity of the eye, under the conjunctiva, etc. (e.g., such as in the subconjunctival drug delivery implant 722 shown in FIG. 46).

In one embodiment, the donor corneal tissue is cut with a circular trephine of at least 7-8 mm in diameter, separating the circular corneal area from the donor eye and removing the corneal epithelium and corneal endothelial cells from the donor corneal tissue, and cutting in two circular leftover corneal donor portions of two equal dimensions with a keratome or a femtosecond laser, one portion from the anterior surface to a distance of 50-200 microns uniform thickness with Bowman's membrane/stroma 3-D inlay, and another portion from the posterior corneal surface with a 50-200 microns uniform thickness having the Descemet membrane to build a 3-D circle of the corneal stroma and Descemet inlay, and then cross-linking portions with a solution having riboflavin nanoparticles and an antibiotic, and irradiating the portions with UV radiation to kill the stromal keratocytes along with potential pathogens while crosslinking the collagen fibrils in the inlays, then transplanting the cross-linked inlay over the exposed corneal stroma after creation of a LASIK hinged flap to ablate the front surface of the inlay with an excimer laser using wavefront technology, and finally replacing the LASIK flap over the inlay covering it with the corneal stroma from all sides.

In another embodiment, the donor corneal tissue is cut with a circular trephine of at least 7-8 mm in diameter, separating the circular corneal area from the donor eye, and removing the corneal epithelium and corneal endothelial cells from the donor corneal tissue, and cutting in two circular leftover corneal donor portions into two equal dimensions with a keratome or a femtosecond laser, one portion from the anterior surface to a distance of 50-200 microns uniform thickness with Bowman's membrane/stroma 3-D inlay, and another portion from the posterior corneal surface with a 50-200 microns uniform thickness having the Descemet membrane to build a 3-D circle of the corneal stroma and Descemet inlay, and then cross-linking the portions with a solution having riboflavin nanoparticles and an antibiotic, irradiating the portions with UV radiation to kill the stromal keratocytes along with potential pathogens while crosslinking the collagen fibrils in the inlays, modifying the front surface of the inlays with an excimer laser to a desired shape, and then cutting the inlay with its Descemet membrane in two or three sections to be implanted inside the host corneal stromal. In this embodiment, the Bowman's membrane and/or Descemet's membrane is kept so as to contribute to biomechanical stability of the inlay. A pocket is created with a femtosecond laser, and then the inlay pieces are inserted through a small incision to correct the refractive power of the host eye. The inlay can be cut into 2-3 pieces with a knife prior or after crosslinking the inlay.

In another embodiment, only a single inlay is cut from the donor cornea, rather than the multiple inlay portions described above.

In one embodiment, the corneal endothelium and epithelium of a human donor cornea is removed mechanically or in combination with low concentration of alcohol in water, etc. prior to implantation of the human donor cornea.

Figure 70:
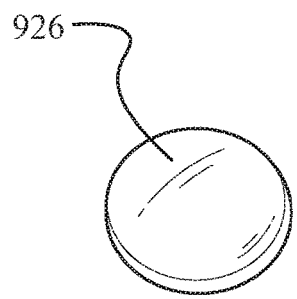
FIG. 70 is a front view illustrating donor corneal stromal tissue, according to one embodiment of the invention.

In one embodiment, a uniform rectangular or circular piece of human donor stromal tissue, a tissue culture grown cornea, a genetically modified cornea, or an acellular human or animal cornea is cut with either a microkeratome or a femtosecond laser or a trephine to create a 3-D corneal stromal circle with a thickness of 10 to 50 microns, 50 to 150 microns, or 50 to 200 microns under sterile conditions (see FIG. 70). The acellular human or animal cornea may be created using 0.05-0.5% or more sodium dodecyl sulfate (SDS), Triton X-100, benzalkonium chloride (BAK), Igepal, or genipin for 15 minutes to 6 hours or more depending on the concentration used to generate acellular corneal inlays, and the corneal tissue is cleaned in 100% glycerol, and sterilized by killing bacteria, viruses and/or parasites, or the corneal inlay may be re-sterilized by ethylene oxide or during the surgery by crosslinking the donor tissue with the host cornea with UV light and 0.1% of riboflavin nanoparticles.

In one embodiment, the human corneal inlay is made acellular by glycerin and cryopreservation and then thawing it for use in a physiological solution of 0.1% riboflavin nanoparticles, and finally cross-linking it with UV radiation after implantation.

In one embodiment, 0.1% of riboflavin nanoparticles in a physiological solution of pH 6.5-7.5 and osmolality of about 300 milliosmole (mOsm) with or without antibiotics or antivirals, etc. as additives, applied topically on the cornea, the conjunctiva, and/or the lid margin and exposed to UV light or just the sunshine or a white light can sterilize the infected cornea, conjunctiva, or the lid, while repeated daily one time administration can cross-link the anterior part of corneal collagen, etc. preventing corneal ectasia, progression of keratoconus, or high myopia.

In one embodiment, by using a trephine, the donor cornea is cut to create inlay circles of 3 to 9 millimeters (mm) or more in diameter for intrastromal implantation that can be preserved in a tissue culture or a physiological solution having an antibiotic, antifungal, and a preservative or detergent, such as sodium dodecyl sulfate (SDS), to eliminate the contaminated pathogens. In addition, the donor cornea may be stored in a low concentration of chondroitin sulfate, hyaluronic acid, or albumin to exert an oncotic pressure on the cornea so as to prevent it from swelling during the transport thereof.

In one embodiment, the corneal stromal inlay is de-cellularized with a solution of 0.1-0.5% sodium dodecyl sulfate (SDS) for simultaneous preservation of the corneal inlay and killing the bacteria, viral, or parasites prior to implantation inside a corneal LASIK flap, then placing the corneal inlay over the exposed corneal stroma after cleaning it in 100% glycerol, correcting the refractive error of the host eye with an excimer laser, then applying a solution of riboflavin/medication over the inlay, replacing the flap, and crosslinking the inlay and the stromal wall with UV radiation.

In one embodiment, the corneal stromal inlay is de-cellularized with a solution of 0.1-0.5% sodium dodecyl sulfate (SDS) for simultaneous preservation of the corneal inlay and killing the bacteria, viral or parasites prior to implantation inside a corneal pocket created with a femtosecond laser, correcting the refractive error of the inlay prior to implantation in the host eye with the excimer laser or a femtosecond laser, then the corneal inlay is placed inside a corneal pocket, and a solution of 0.1% riboflavin/medication in a hyaluronic acid solution is applied to the inlay and the surrounding tissue, excess hyaluronic acid is removed from the cavity, and the inlay and the surrounding wall of the cornea are cross-linked with UV radiation.

In one embodiment, the stromal inlays are preserved in a hypothermic storage at 2 to 8° C., or stored by freezing, by freeze drying, in glycerol, and/or gamma radiated and placed in hypothermic solution of tissue culture medium or organ culture medium.

In one embodiment, hypothermia reduces the demand for metabolic energy and since the stromal inlay does not have a corneal epithelium and endothelium or keratocytes its demand is very low, therefore it can be preserved longer (e.g., 45 days or more) than a normal cornea can be preserved, which is about one month.

In one embodiment, the preserving solution for the stromal inlay can have chondroitin sulfate to prevent swelling of the tissue or it can have 4-8% dextran 40, or include ascorbic acid, albumin, hyaluronic acid, or low molecular weight heparin, etc.

In one embodiment, the solution can become a gel with the corneal inlay in it by the addition of a crosslinker to it so as to crosslink the albumen or adding trehalose to the solution and to maintain a gel-like structure with proper pH and osmolality of the surrounding inlay.

In one embodiment, the preserving solution can be McCarey-Kaufman medium (M-K medium) containing 5% dextran 40.

In one embodiment, the storage temperature can be 2-4 degrees C. or more, and the storage can be 30-45 days or more.

In one embodiment, the solution can have non-ionic surfactants (Poloxamer 188) for hypothermic storage.

In another embodiment, the intrastromal inlay can be placed in in 10-80 ml Eagle's medium containing HEPES buffer, 26 mmol/l, NaHCO$_3$, 2% FBS, 2 mmol/l L-glutamine, penicillin, streptomycin and amphotericin B, and stored at 4-34° C. for 30-45 days in a sterile container.

In one embodiment, the intrastromal inlays can be stored in a solution of amphotericin B Optisol-GS that is effective against *Candida* species.

Figure 71:
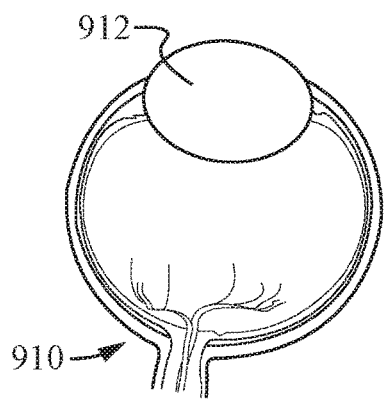
FIG. 71 is a cutaway perspective view of an eye before a corneal flap has been formed in the eye.
Figure 72:
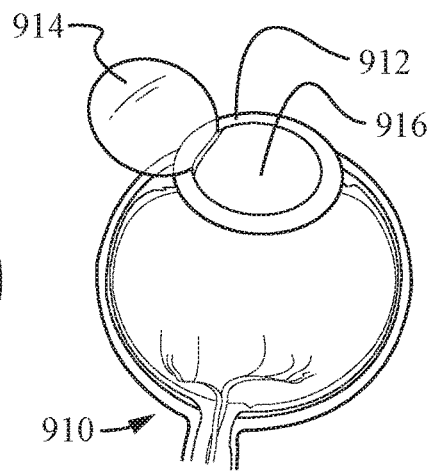
FIG. 72 is another cutaway perspective view of the eye of FIG. 71 illustrating the formation of a corneal flap in the eye.
Figure 73:
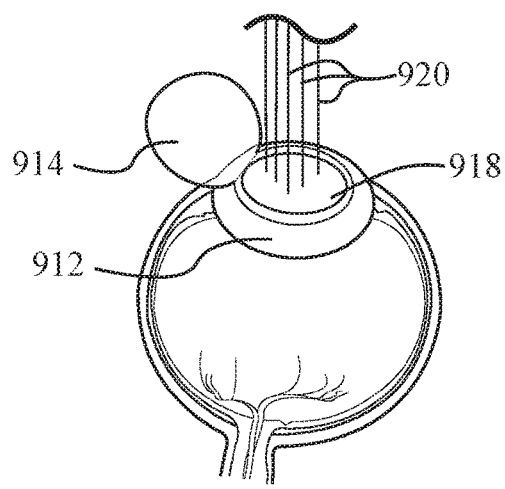
FIG. 73 is yet another cutaway perspective view of the eye of FIG. 71 illustrating the insertion of a corneal inlay under the flap of the eye, wherein corneal inlay is undergoing refractive correction.

In one embodiment, the intrastromal inlay is transplanted over the center of an exposed corneal stroma which is created in a known laser-assisted in situ keratomileusis (LASIK) procedure using a femtosecond laser or a microkeratome where the flap is created and hinged away to expose the corneal stroma (see FIGS. 71-73).

Figure 74:
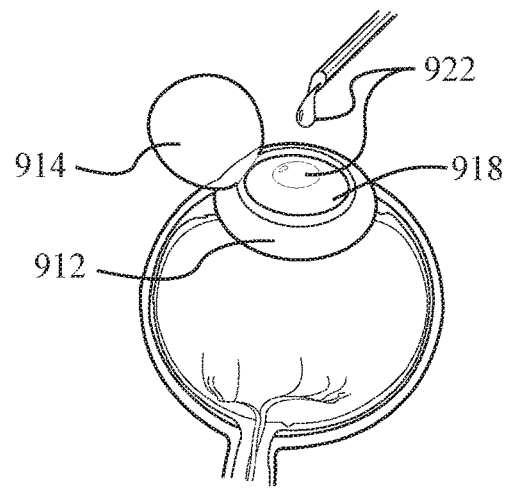
FIG. 74 is still another cutaway perspective view of the eye of FIG. 71 illustrating the application of a photosensitizer solution to the corneal inlay by drops.
Figure 75:
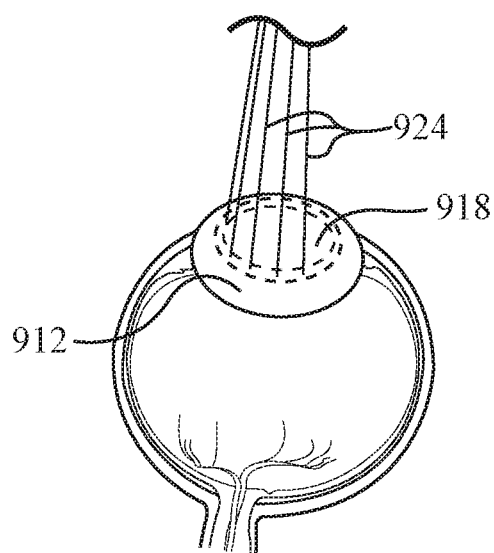
FIG. 75 is yet another cutaway perspective view of the eye of FIG. 71 illustrating the cross-linking of the corneal inlay using ultraviolet radiation after the photo sensitizer solution has been applied to the corneal inlay.
Figure 76:
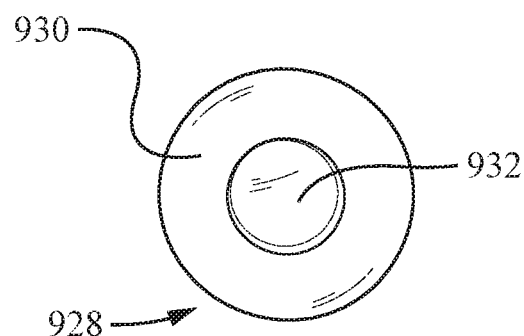
FIG. 76 is a front view of an eye illustrating an intrastromal cavity that has been created in the eye using a laser, according to another embodiment of the invention.
Figure 77:
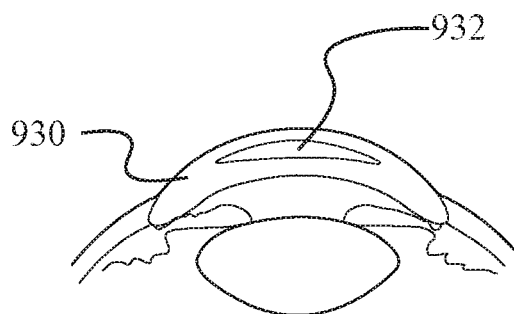
FIG. 77 is a partial side cross-sectional view of the eye of FIG. 76 illustrating the intrastromal cavity.
Figure 78:
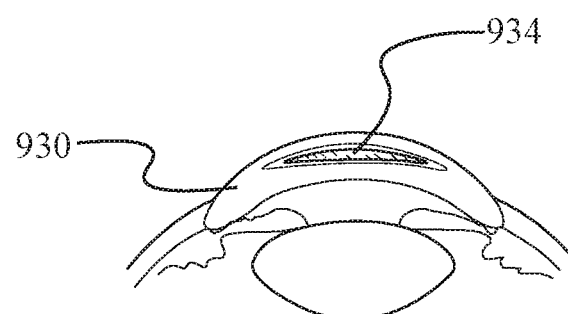
FIG. 78 is another partial side cross-sectional view of the eye of FIG. 76 illustrating a shaped donor cornea that is disposed in the intrastromal cavity.
Figure 79:
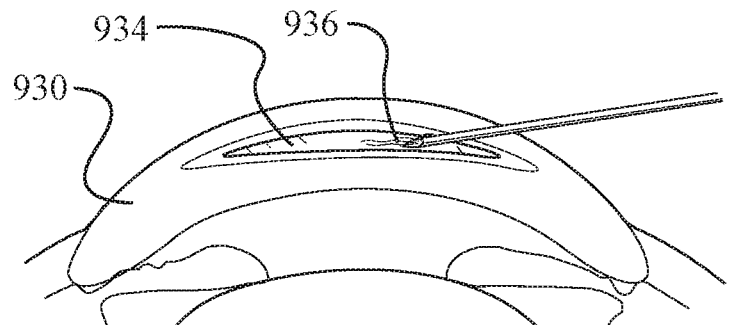
FIG. 79 is yet another partial side cross-sectional view of the eye of FIG. 76 illustrating the injection of a photosensitizer into the shaped donor cornea inside the intrastromal cavity.

In one illustrative embodiment, with reference to FIGS. 70-75, a method of corneal implantation with cross-linking will be described. Initially, referring specifically to FIG. 72, a LASIK flap 914 is formed in a cornea 912 of an eye 910 so as to expose a stromal tissue 916 of the cornea 912 underlying the flap 914. Then, the flap 914 is pivoted so as to expose the stromal tissue 916 of the cornea 912 underlying the flap 914 (see FIG. 72). After pivoting the flap 914, an implant or inlay 918 is inserted under the flap 914 so as to overlie the stromal tissue 916 of the cornea 912 (see FIG. 73). Then, as shown in FIG. 73, laser energy 920 (e.g., by means of an excimer laser) and/or microwaves are applied to the implant 918 in the eye 910 so as to modify the refractive power of the implant 918 while being monitored using a Shack-Hartmann wavefront system so as to achieve a desired refractive power for the implant 918. Turning to FIG. 74, after the laser application, a cross-linking solution 922 that includes a photosensitizer is applied to the implant 918 (e.g., by drops or injection). Next, the implant 918 is covered with the flap 914 such that the implant 918 is surrounded entirely by the stromal tissue of the cornea 912. Finally, as shown in FIG. 75, the implant 918 is irradiated (e.g., with ultraviolet (UV) radiation 924) so as to activate cross-linkers in the implant 918, and thereby cross-link the implant 918 to prevent an immune response to the implant 918 and/or rejection of the implant 918 by the patient. The wall of the stroma of the eye 910 surrounding the implant 918 may also be cross-linked together with the implant 918 for a predetermined time duration (e.g., ten minutes).

In the illustrative embodiment of FIGS. 70-75, the implant or inlay 918 may be formed from donor corneal tissue, a tissue culture grown cornea, or a 3-D printed cornea. When the implant or inlay 918 is formed from donor corneal tissue, the donor corneal tissue may initially be cut into a circular implant 926 using a circular trephine (see FIG. 70), where the circular implant has a diameter between 3 millimeters and 10 millimeters. Then, the circular implant 926 may be cut into two circular disks using a keratome or a femtosecond laser, each of the two circular disks having a thickness between 50 microns and 200 microns.

In one embodiment, the stromal inlay size and thickness is chosen depending on the degree of the corrective dioptric power that is needed. In one embodiment, an inlay with a thickness of 50 microns can correct 5 dioptric powers, and with 150 micron thickness can correct 15 dioptric power, etc.

In one embodiment, the stromal inlay has a diameter of about 3 mm and is placed just inferior to the center of the visual axis and corrected to have a dioptric power of ±1-3.00 D or more for patients with presbyopia for reading that is creating a bifocal cornea, where the patient sees far through the center of the cornea and near, through the small inlay.

In one embodiment, the refractive error of the eye is corrected after the LASIK flap is created and the inlay is positioned over the exposed center of the corneal stroma by the use of an excimer laser and wavefront technology and a Shack-Hartmann sensor to correct myopic, hyperopic, or astigmatic or other higher order of refractive errors of the eye (see FIG. 73), then a few drops of the solution of 0.1% riboflavin nanoparticles, conjugated with cell penetrating peptides (CPP) or activatable cell penetrating peptides (ACPP) having antibiotic, antifungal, or anti-parasitic medication, etc. or anti-inflammatory agents, such as Rock inhibitors, anti-integrins, GSK inhibitors, etc. at a non-toxic dose of 1 microgram to 100 microgram in 0.1 milliliters (ml) or a concentration for use in intravitreal irrigating solutions, or as slow release biodegradable polymeric polylactic acid or polyglycolic acid or their combinations of porous silicon, micelles or polycaprolactone nanoparticles are administered over the inlay and exposed corneal stroma (see FIG. 74) to treat the inflammatory processes and prevent tissue scarring.

In one embodiment, the riboflavin may penetrate the inlay within 1-3 minutes.

In one embodiment, the hinged corneal flap is repositioned so that the inlay is covered on all sides by the host corneal stroma, which now is also exposed the riboflavin solution.

In one embodiment, the nanoparticles of riboflavin solution can be injected under the corneal flap over the inlay though a small 25-30 gauge needle or smaller needle to expose the inlay and the corneal cavity to the riboflavin solution, then the cornea, including the inlay is irradiated with UV radiation of 3-10 milliW/cm$^2$ from outside the cornea for a short period of 3-10 minutes to cross-link only the inlay and its surrounding corneal stroma, thereby killing all remaining cells in the inlay and any potential pathogens that might have contaminated the inlay or the stroma by the combination effects of the UV radiation, riboflavin nanoparticles, CPP, and medication and sterilize the inlay and the stromal cavity. In one embodiment, the corneal cavity and the flap can be irradiated with UV laser brought under the corneal flap through a fiber optic, thus crosslinking the inlay and the surrounding stromal tissue while the tissue close to the corneal endothelium or close to the anterior surface of the corneal are not cross-linked.

In one embodiment, the nanoparticles of riboflavin solution can be injected under the corneal flap over the inlay though a small 25-30 gauge needle or smaller needle to expose the inlay and the corneal cavity to the riboflavin solution, then the cornea, including the inlay is irradiated with UV radiation of 3-10 milliW/cm$^2$ for a short period of 5-10 minutes using a fiber optic with an small lens on its tip to focus the laser beam only for a distance of 20-50 microns, and then it diffuses out so that the endothelial cells, or the crystalline lens, or the retina is not exposed to a heavy dose of UV radiation. In one embodiment, the tip of the fiber optic moves all over the front surface of the intrastromal inlay to crosslink only the inlay and its surrounding corneal stroma, killing all remaining cells in the inlay and any potential pathogens that might have contaminated the surgical area by the combination effects of the UV radiation, riboflavin nanoparticles, CPP, and medication and sterilize the inlay and the stromal cavity while eliminating the toxic effect of the UV radiation to the anterior or the posterior corneal tissue.

Figure 80:
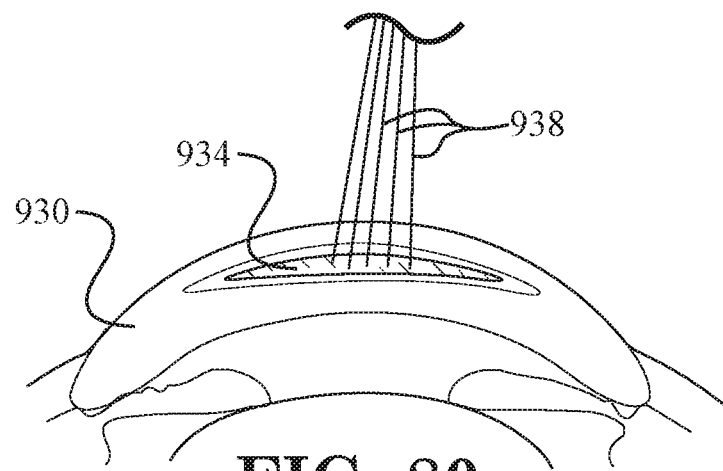
FIG. 80 is still another partial side cross-sectional view of the eye of FIG. 76 illustrating the cross-linking of the shaped donor cornea using externally applied ultraviolet radiation.
Figure 81:
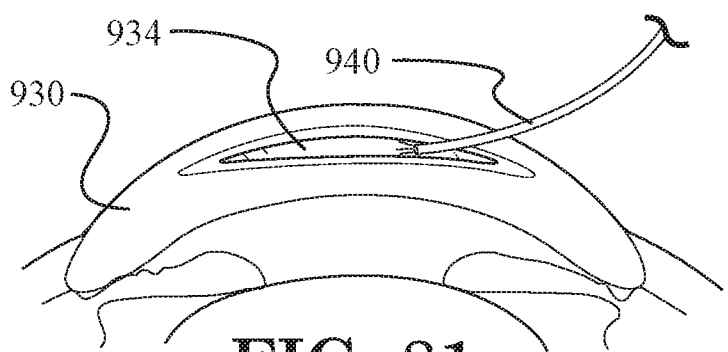
FIG. 81 is yet another partial side cross-sectional view of the eye of FIG. 76 illustrating the cross-linking of the shaped donor cornea using internally applied ultraviolet radiation delivered using a fiber optic.

In one illustrative embodiment, with reference to FIGS. 76-81, another method of corneal implantation with cross-linking will be described. Initially, referring specifically to FIGS. 76 and 77, an intrastromal cavity 932 is formed in the cornea 930 of an eye 928. Then, the intrastromal cavity 932 of the cornea 930 is filled with a shaped donor cornea implant 934 (see FIG. 78). After inserting the shaped donor cornea implant 934 in the intrastromal cavity 932, a cross-linking solution 936 that includes a photosensitizer (e.g., riboflavin) is injected into the implant 934 (e.g., by using a needle for injection—see FIG. 79). Finally, as shown in FIG. 80, the implant 934 is irradiated (e.g., with ultraviolet (UV) radiation 938) so as to activate cross-linkers in the implant 934, and thereby cross-link the implant 934 to prevent an immune response to the implant 934 and/or rejection of the implant 934 by the patient. The wall of the stroma of the eye 928 surrounding the implant 934 may also be cross-linked together with the implant 934 for a predetermined time duration (e.g., ten minutes). In FIG. 80, the ultraviolet (UV) radiation 938 is shown being externally applied to the cornea 930 of the eye 928 with the implant 934. Although, rather than being externally applied, the ultraviolet (UV) radiation may also be internally applied to the implant 934 by means of a fiber optic 940 (see FIG. 81). For example, the UV radiation may be applied inside the tissue with the fiber optic 940, which may include a small incision lens at its tip to focus the lens in the tissue for a very short distance of about 100 microns and then it diverges, thus preventing damage in the back of the corneal, endothelial cells, the crystalline lens, the retina, the corneal epithelial cells, or the corneal nerves plexus under the epithelium.

In the illustrative embodiments described above, the intrastromal implant or inlay 918, 934 is not cross-linked, and its refractive power is not corrected prior its transplantation into the recipient cornea 912, 930. The implantation procedure may be either a MESICK (Meso=inside, I=inlay, C=Crosslinking, K=Keratomileusis) procedure, or small incision implant procedure. In one or more other embodiments, the refractive power of the implant or inlay is corrected, but cross-linking is done after implantation inside a stromal pocket.

In one embodiment, microwave radiation may be used to modify the refractive error of the cornea or the inlay rather than laser radiation delivered by an excimer laser. Also, nanojoule pulses of a femtosecond laser may be applied to small lenticules after implantation to change the index of the refraction of the small incision lenses in the stromal cavity. In addition, a combination of cross-linking and microwave application may be used to crosslink the cornea and correct the refractive error while maintaining the corneal transparency.

In one embodiment, subsequently an antibiotic ointment or solution is applied to the operated eye in the post-operative period, and in some embodiments, if needed, the crosslinking process can be repeated inside the stroma and in the inlay to kill potential invading cells as needed and to keep the inlay's transparency.

In one embodiment, after the surgery, the refractive power of the cornea or the inlay can be modified using focally administrated focused microwaves.

In one embodiment, the corneal crosslinking can be combined with microwave application in the same session to achieve synergistic results.

In one embodiment, one can modify the refractive index of the corneal inlay by the use of few nanojoules of femtosecond laser application which does not cut or damage the inlay.

In one embodiment, the crosslinking solution and its components are used to treat an infected wound of the cornea, skin, or mucosa to be irradiated with UV light and kill the bacterial, viral, fungal and/or parasitic infection or the antibiotic resistant bacteria MRSA, or viruses or prions in the infected tissue and the corneal implant, etc.

In one embodiment, the implant is formed from donor corneal tissue, and wherein, prior to the step of inserting the implant under the flap, the method further comprises the steps of cutting a circular implant from a donor cornea using a circular trephine, the circular implant having a diameter between approximately 3 millimeters and approximately 9 millimeters or more; and cutting the circular implant disks using a trephine or a femtosecond laser, the two circular disks having a thickness between approximately 50 microns and approximately 100 microns and shaping the inlay surface's refractive power with an excimer laser.

In one embodiment, a corneal pocket is created in the host corneal stroma with a diameter of 3-9 mm slightly larger than the diameter of the inlay for ease of implantation, using a femtosecond laser, and marking its center and making a small side incision in the cornea to access the inside of the intrastromal pocket and to separate the stromal pocket using a micro-spatula or a bent needle and hyaluronic acid, and then a pre-shaped corneal inlay and hyaluronic acid is implanted alone or with N-Vinylpyrrolidone and riboflavin for ease of implantation in the corneal stromal pocket, riboflavin or photosensitizer nanoparticles are injected in the corneal pocket to penetrate the inlay and slightly the wall of the pocket, and then the inlay and the wall of the pocket and hyaluronic acid are cross-linked with UV radiation, thus converting the hyaluronic acid into a gel.

In one embodiment, one uses a fluid containing inorganic or organic molecules such as hyaluronic acid, collagen, elastin, chondroitin sulfate or hydrogel, polyethylene glycol, or biotin, polycaprolactone, chitosan, etc. in various combinations in a physiologic solution having in addition a crosslinker such as riboflavin, N-Vinylpyrrolidone, or other medications.

In another embodiment, the implant is formed from donor corneal tissue or a 3-D printed cornea, and prior to the step of inserting the implant in the corneal stroma, one performs the steps of cutting a circular implant from a donor corneal stroma, etc. using a circular trephine, the circular implant having a diameter between approximately 3 millimeters and approximately 9 millimeters and creating a corneal pocket in the host corneal stroma with a diameter of 4-10 mm using a femtosecond laser, or any other laser and making one or two small side incisions in the cornea with the same femtosecond laser or a knife, to access the inside of the intrastromal pocket and to separate the walls of the pocket using a micro-spatula and hyaluronic acid and cutting the circular implant into two concentric circular parts, one circular disk inside the outer doughnut part using a smaller trephine than the diameter of the inlay or a femtosecond laser, the two concentric circular parts having a thickness between approximately 50 microns to approximately 100 microns and their surfaces are shaped to form a desired refractive power with an excimer laser to correct a myopic, hyperopic or astigmatic error of the eye after their separate implantation using forceps or an injector, the annular part first, then the disc part through a small incision that is made from outside to access the inside of the stromal pocket where the two pieces are joined again after their implantation. The pre-shaped corneal inlay is implanted with the annular part first, then the disk inside it second along with hyaluronic or low molecular weight heparin for ease of implantation in the corneal stromal pocket, riboflavin or riboflavin nanoparticles are injected as a 0.1-1% solution or another photosensitizer is injected along with other antibacterial or antifungal medications in the corneal pocket to penetrate the inlay and slightly the wall of the pocket, and finally the inlay and the wall of the pocket are crosslinked with UV radiation and to kill the potential pathogenic contamination associated with the implant.

In one embodiment, the inner disk implant can be organic and the outer annular part of the implant can be made from a synthetic transparent polymer or acrylic that is resilient or flexible and in one piece or multiple separate pieces, which may be implanted through a small incision made in the wall of the cornea after creating a corneal pocket with a larger diameter for the desired implant for ease of implantation.

In one embodiment, one uses a fluid containing inorganic or organic molecules, such as hyaluronic acid, low molecular weight heparin, collagen, elastin, chondroitin sulfate, hydrogel, polyethylene glycol, chitosan, biotin, polycaprolactone, etc. or in various combinations in a physiologic solution having, in addition to a crosslinker such as riboflavin or N-Vinylpyrrolidone, other medications, such as Rock inhibitors or anti-integrins, where the transparent solution has a refractive index of equal to 1.34 or more for correction of a hyperopic error, and is to be injected into a corneal stromal pocket of the recipient cornea prepared using a femtosecond laser or picosecond laser, etc. and to increase the anterior curvature of the stromal cavity by pushing the anterior wall of the cavity forward after injecting more solution, or reducing its curvature by removing an amount of fluid from the stromal cavity, to treat a hyperopic refractive error to the desired degree using a wavefront technology during the processes of the injection and immediately irradiating the cornea with UV radiation to convert the fluid-filled cavity into a cross-linked gel creating an intrastromal transparent lens with an anterior convex surface and an index of refraction of 1.34 or more and cross-linked adjacent corneal stromal tissue to prevent an immune response to the gel and kill potential existing pathogens in the gel and the cornea and prevent the lens from extruding through the small stromal opening made for injection.

In one embodiment, the crosslinking of the cornea and the inlay can be repeated using an internal injection of riboflavin nanoparticles in a physiological solution in the stromal cavity or applying riboflavin/medication drops from outside to penetrate the anterior cornea and the inlay, which are being cross-linked again with externally applied UV radiation to kill potential invading inflammatory cells, or organisms if any sign of rejection or cellular invasion or infection is observed to stop the process, or the implant is emulsified with a femtosecond laser and washed out or removed or replaced.

In one embodiment, a corneal pocket is created inside the corneal stroma using a femtosecond laser and a circular 3-D circular area is cut with a uniform thickness of approximately 60 microns inside the pocket prior to separation of the anterior stromal layer, then a small incision is cut to the side of the cornea to access inside the corneal pocket and remove the circular uniform disc from the stroma near the back of the cavity to create more space inside the corneal pocket and a new corneal inlay is placed inside the pocket, the inlay having a corrected refractive error of the eye for hyperopia, myopia, and astigmatisms, and riboflavin nanoparticles along with hyaluronic acid in solution is injected inside the corneal cavity, and the inlay and the surrounding stromal tissue is cross-linked with UV radiation or another wavelength of light if a different crosslinker is used, to prevent corneal rejection or infection.

In another embodiment, a cavity is formed and a uniform disk or oval-shaped portion of the stroma of about 60-100 micron tissue thickness is removed, and the cavity is injected with cross-linkable molecules in a transparent biocompatible solution having a crosslinker to correct the hyperopic, hyperopic, or astigmatic refractive error of the eye, and the cross-linkable fluid is cross-linked by externally applied UV laser radiation to cross-link the fluidic cavity and convert it into a cross-linked gel and cross-link the corneal pocket wall, while killing potential pathogens infecting the surgical area and preventing the escape of the gel inlay from the small incision that was initially made to access the corneal cavity and preventing glare seen after removal of the stromal tissue.

In one embodiment of corneal implantation with cross-linking, the method comprises the steps of: (i) forming a flap in a cornea of an eye so as to expose a stromal tissue of the cornea underlying the flap; (ii) pivoting the flap so as to expose the stromal tissue of the cornea underlying the flap; (iii) inserting an implant under the flap so as to overlie the stromal tissue of the cornea; (iv) applying laser energy to the implant in the eye so as to modify the refractive power of the implant and the eye while being monitored using a Shack-Hartmann wavefront system so as to achieve a desired refractive power for the implant.

In one embodiment, a cross-linking solution that includes a photosensitizer is applied to the implant and to the stromal tissue of the cornea surrounding the implant, the implant is covered with the flap, the implant being surrounded entirely by the stromal tissue of the cornea; and the implant and the stromal tissue of the cornea surrounding the implant is irradiated so as to activate cross-linkers in the implant and in the stromal tissue of the cornea surrounding the implant, and thereby cross-link the implant and the stromal tissue of the cornea surrounding the implant to prevent an immune response to the implant and/or rejection of the implant by the patient.

In one embodiment, the implant is formed from donor corneal tissue, a tissue culture grown cornea, a 3-D printed cornea, or preferably from human donor corneal tissue that is stored in a sterile container having an antibiotic and a preservative solution without cross-linking the implant prior to implantation, and a corneal LASIK flap is formed in the recipient cornea using one a femtosecond laser or a mechanical keratome.

In one embodiment, the photosensitizer of the cross-linking solution comprises nanoparticles of riboflavin, or another photosensitizer, and the step of irradiating the implant comprises irradiating the implant with ultraviolet light or a chemical crosslinker.

In one embodiment, the cross-linking solution contains one or more medications for treating a medical condition of the patient, the one or more medications selected from a group consisting of a Rock inhibitor, Wnt inhibitor, an integrin inhibitor, a GSK inhibitor, an antibiotic, an anti-fungal medication, and combinations thereof.

In one embodiment, the correction of the refractive power of the eye is done after placement of the inlay over the exposed corneal stroma using an excimer laser so as to modify the refractive power of the implant and the eye under the control of wavefront technology controlled with a Shack-Hartmann sensor.

In one embodiment, the cross-linking solution includes a photosensitizer in the form of riboflavin nanoparticles and a medication selected from the group consisting of an antibiotic, an antiviral, an antifungal, an anti-parasitic, and combinations thereof; and the cornea is irradiated with ultraviolet light to cross-link an infected part of the cornea so as to kill pathogens and treat infectious keratitis.

In one embodiment, the implant is formed from donor corneal tissue by cutting one or more circular implant disks from a donor cornea using a trephine or a femtosecond laser so as to form the implant, the one or more circular implant disks having a diameter between approximately 3 millimeters and approximately 9 millimeters, and the one or more circular implant disks having a thickness between approximately 50 microns and approximately 100 microns; and a surface of the one or more circular implant disks is shaped using an excimer laser prior to implantation under a corneal flap or inside a corneal stromal cavity.

In one embodiment, the implant and the wall of the corneal cavity is cross-linked after implantation using a fiber optic or the implant and the wall of the corneal cavity contains a crosslinker that can be irradiated using an external energy source (e.g., UV radiation) through the surface of the cornea, and the anterior part of the cornea does not have a crosslinker and is not cross-linked during this procedure.

In one embodiment, the cross-linking solution contains nanoparticles of riboflavin, cell penetrating peptides, and an antibiotic, antifungal, anti-viral, and/or antiparasitic medication to treat a bacterial infection of the cornea, skin, or mucosa or the eyelids with ultraviolet radiation to kill the invading pathogens.

In one embodiment, a corneal cavity of 3-9 mm wide or larger is created in the host corneal stroma using a femtosecond laser where a small side incision is made in a recipient cornea of an eye of a patient for insertion of a circular implant into the stromal pocket by injecting the cross linking solution, and then crosslinking the inlay and the wall of the cavity so as to prevent an immune response to the implant and/or prevent rejection of the implant by the patient's tissue.

In one embodiment, the step of forming the small side incision in the recipient cornea of the eye further comprises making the small side incision in the recipient cornea with a femtosecond laser or a knife.

In one embodiment, a cavity is formed in the host stroma and the wall of the cavity is separated using a spatula or a bent needle while injection of a solution of hyaluronic acid, and an implant is inserted along with injection of riboflavin nanoparticles to crosslink the inlay and the wall of the cavity and the remaining hyaluronic acid irradiating the circular implant with ultraviolet light so as to cross-link the circular implant and the portion of the bounding wall of the pocket and the hyaluronic acid, and kill any potential pathogenic contaminants associated with the circular implant and create a clear tissue transition preventing postoperative glare.

In one embodiment, the circular implant is cut with a circular trephine having an outer diameter between approximately 3 millimeters and approximately 9 millimeters; then the circular implant is cut into two concentric circular parts, the first one of the two concentric circular parts comprising an annular disk portion and the second one of the two concentric circular parts comprising a central disk portion inside the annular outer portion, the central disk portion being cut using a femtosecond laser or a trephine having a diameter smaller than the outer diameter of the circular implant, each of the two concentric circular parts having a thickness between approximately 30 microns and approximately 100 microns.

In one embodiment, the surface of the implant is shaped with an excimer laser to prior to implantation in the corneal stromal pocket to form a desired refractive power so as to correct a myopic, hyperopic, or astigmatic error of the eye.

In another embodiment, the implant inserted into the pocket of the recipient cornea via a small incision by initially inserting the annular disk portion into a pocket via the small incision using an injector syringe or a forceps, and then subsequently inserting the central disk portion into the pocket via the small incision using the injector syringe or the forceps, and joining the two concentric circular parts together inside the pocket. Then, a crosslinker with hyaluronic acid is injected inside the pocket over the implant, and the implant and the stromal wall are cross-linked with UV radiation to prevent postoperative glare.

In one embodiment, the central disk portion of the circular implant is organic and the annular disk portion of the circular implant is made from a synthetic transparent polymer, acrylic, or hydrogel, etc. that is resilient or flexible.

In one embodiment, a corneal pocket is formed in the host's posterior corneal stroma using a femtosecond laser, first a circular or oval-shaped three-dimensional disk is cut in the corneal stroma, and a second cut is made in front of the first cut, but the second cut is slightly larger with a substantially uniform thickness or distance from the first cut of approximately 60 microns and 100 microns using the femtosecond laser so as to form the pocket, and the circular or oval-shaped three-dimensional posterior disk is removed from the host corneal stroma to create more space inside the pocket; and the anterior lamella is separated and the posterior lamellar is removed using a micro-spatula or a bent needle, hyaluronic acid is applied for ease of removal of the tissue and insertion of the circular implant into the pocket in the recipient cornea of the eye and to smoothen up the wall of the cavity; riboflavin or other photosensitizer nanoparticles are injected into the pocket in the recipient cornea of the eye so as to penetrate the circular implant and a portion of a bounding wall of the pocket; and the circular implant is irradiated with ultraviolet light or another wavelength of light so as to cross-link the circular implant and the portion of the bounding wall of the pocket, and to prevent corneal rejection of the circular implant and/or prevent corneal infection and postoperative glare.

In one embodiment, a corneal pocket is formed in the host's posterior corneal stroma using a femtosecond laser, first a circular or oval-shaped three-dimensional disk is cut from the corneal stroma, then a second cut is made in front of the first cut, but the second cut is slightly larger with a substantially uniform thickness or distance from the first cut of approximately 60 microns and 100 microns using the femtosecond laser so as to form the pocket, and the circular or oval-shaped three-dimensional posterior disk is removed from the host corneal stroma to create more space inside the pocket by creating two small side incisions opposite each other to gain entry in the pocket from two sides, thus simplifying removal of the stromal tissue or implantation of an inlay afterwards having the two instruments inserted inside the corneal pocket, one having a sharp edge to separate the tissue from the underlying stroma, and the other to hold the edges or two prongs to pull the tissue for ease of manipulation and removal of the circular or oval-shaped three-dimensional disk with a uniform thickness from the host's posterior corneal stroma to create more space inside the pocket; and portions of the pocket are separated using a micro-spatula or a bent needle and hyaluronic acid; and hyaluronic acid is used for ease of insertion of the circular shaped implant into the pocket to correct the refractive error of the eye in the recipient cornea of the eye and smoothen up the wall of the cavity, an riboflavin or other photosensitizer nanoparticles are injected with or without hyaluronic acid into the pocket in the recipient cornea of the eye so as to penetrate the circular implant and a portion of a bounding wall of the pocket; and the circular implant is irradiated with ultraviolet light or another wavelength of light so as to cross-link the circular implant and the portion of the bounding wall of the pocket, and to prevent corneal rejection of the circular implant and/or prevent corneal infection and postoperative glare.

In one embodiment, after creating and removing a circular or oval-shaped three-dimensional disk from the pocket, cross-linkable molecules or monomers are injected in a transparent biocompatible solution containing a crosslinker into the pocket so as to correct a hyperopic, hyperopic or astigmatic refractive error of the eye; and under control of wavefront technology and a Shack-Hartmann sensor, the transparent biocompatible solution is cross-linked by externally applying ultraviolet radiation so as to cross-link the solution inside the pocket and convert the solution to a cross-linked gel, and to further cross-link a bounding wall of the pocket and kill any potential pathogens infecting the surgical area of the eye and preventing postoperative glare.

In one embodiment, one uses a femtosecond laser or picosecond laser to form the pocket in the recipient cornea of the eye, then injects a cross-linking solution into the pocket in the recipient cornea of the eye so as to penetrate the circular implant and a portion of a bounding wall of the pocket, the cross-linking solution comprising a transparent fluid that contains inorganic or organic molecules or monomers that include hyaluronic acid, and its modified derivatives, N-isopropylacrylamide, alginate, thiol, tyramine, collagen, elastin, chondroitin sulfate, hydrogel, photo-crosslinked hydrogel, polyethylene glycol, poly(vinyl alcohol) (PVA), biotin, chitosan, and combinations thereof, in addition to a photosensitizer and one or more medications, the transparent fluid having a refractive index equal to 1.34 or more for correction of a hyperopic error; increasing the corneal curvature by pushing an anterior wall of the pocket forward by injecting more of the transparent fluid, or reducing an amount of the transparent fluid to treat a hyperopic refractive error to the desired degree using wavefront technology; and the recipient cornea is irradiated with ultraviolet light to convert the transparent fluid in the pocket into a cross-linked gel, thus creating an intrastromal transparent lens with an anterior convex surface and an index of refraction of 1.34 or more, producing cross-linked adjacent corneal tissue so as to prevent an immune response to the cross-linked gel and kill potential existing pathogens in the cross-linked gel and the recipient cornea, and to prevent the intrastromal transparent lens from extruding through the small side incision in the recipient cornea and prevent postoperative glare.

In one embodiment, the crosslinking preparation containing medications is cross-linked and used as a device that can be placed over or under the conjunctiva, or the lid, so as to be used as a drug delivery device for delivering a non-toxic dose of antibiotic, antiviral, antifungal, anti-parasitic, Rock inhibitors, integrin inhibitors, or Wnt inhibitors after LASIK surgery, corneal transplant, PRK, or after any corneal or conjunctival procedure to treat infection, reduce inflammatory process to reduce scarring, after ocular surgery, encourage nerve growth in the cornea after refractive surgery and treat infective diseases of the cornea, conjunctiva, or the lid.

In one embodiment, the photosensitizer or the cross-linking solution is riboflavin, and the one or more medications are selected from a group consisting of a Rock inhibitor, Wnt inhibitor, an integrin inhibitor, a GSK inhibitor, an antibiotic, an anti-fungal medication, and combinations thereof.

In one embodiment, the recipient cornea and the intrastromal inlay are cross-linked one or more additional times with the crosslinker and a suitable medication is applied if any sign of rejection and/or cellular invasion or infection is observed so as to stop the rejection and/or the cellular invasion.

In one embodiment, one can emulsify the intrastromal transparent gel using a femtosecond laser, washing out or removing the emulsified intrastromal transparent gel, and replacing the emulsified intrastromal transparent gel with a new intrastromal transparent gel-able preparation.

In one or more further embodiments described hereinafter, improved procedures for preserving donor corneas will be explained. Although the transplantation of the cornea was introduced a century ago, it was much later in the 1940s-1950s that corneal preservation for the full thickness transplantation was attempted. Using the so-called moist chamber, initially the entire eye was stored at 2-6° C. as hypothermic. Subsequently, the cornea and some surrounding tissues were kept in organ culture at 31-37° C. Freezing the corneal tissue was discouraged, since it damages the endothelial cells that are useful for regulating the fluid transport in the full thickness corneal graft.

At present, the maximal time that the corneal tissue can be preserved is about 14 days, but, in general, the preserved cornea loses their viability after 3-4 days. These corneas become permeable to water in the culture media, become cloudy and useless as corneal transplant are discarded.

In one embodiment, the corneas are obtained shortly after the donor's death. Biopsies of the eye surfaces are taken for bacteriological evaluation and culture. Corneal storage after corneal or scleral crosslinking does not require any matching, since all proteins, such as collagen are cross-linked during the process of cross-linking using a photosensitizer, such as riboflavin, and light, such as ultraviolet (UV) light and the cross-linked collagen is not immunogenic. Nevertheless, after the initial step of bacteriological biopsy, the eye is placed in a bottle for transfer under aseptic conditions having a solution containing antibiotics and/or antimycotics, since about 10% of the eyes can be contaminated, but the actual incidence of endophthalmitis is very low.

In one embodiment, the retrieved corneas from the eye bank are prepared by dissecting the soft tissue conjunctiva, muscles, retina, choroid, iris, the ciliary body, and the optic nerve, which are cut away and removed. The endothelial cells and the corneal epithelium are scraped away leaving only the sclera and the corneal stroma. The corneal stroma and scleral tissue are washed and cleansed in a physiological solution or washed with a solution of povidone iodine and then with a physiological solution, and prepared for in vitro crosslinking.

In one embodiment, the advantage of using a photosensitizer and its activation in the tissue with light (e.g. UV light) is that the corneal tissue is cross-linked, and it does not lose its transparency, which is very important after corneal transplantation so that the light reaches the retina without being distorted or absorbed, whereas the cross-linking of tissue with the use of chemical crosslinkers, such as a formaldehyde, interferes with not only the transparency of the cornea, but makes it very stiff, in addition to being very toxic to the surrounding tissue.

In one embodiment, the cornea or the sclera are cut to a specific shape and size as needed.

In one embodiment, the corneal tissue can be cut using a knife, keratome, a femtosecond laser, or excimer laser to the shape and thickness of a lens with defined diameter, or dioptric power creating plus or minus astigmatic lens, or a toric lens.

In one embodiment, the corneal or scleral tissues are initially cross-linked prior to the surgery, and then cut using a knife, keratome, a femtosecond laser, or an excimer laser to the shape and thickness of a lens with defined diameter, or dioptric power and thickness creating a plus or minus astigmatic lens or a combination thereof.

In one embodiment, the corneas may be cut to be circular, with a central hole of 1-7 millimeters (mm) or rectangular, oval, etc. or any desired shape for implantation inside the host cornea in a pocket created with a femtosecond laser at any depth of the host corneal stroma.

In one embodiment, the lens implant may have one of: (i) a concave surface to correct myopic refractive errors (i.e., a minus lens for correcting nearsightedness), (ii) a convex surface to correct hyperopic refractive errors (i.e., a plus lens for correcting farsightedness), or (iii) a toric shape to correct astigmatic refractive errors.

In one embodiment, the corneas are cross-linked for storage in eye bank by placing them is a crosslinking solution having any photosensitizer, such as riboflavin, at any desired concentration and osmolarity, preferably of 300 mOsm/L at a pH of 4-8, preferably pH 7.4, and having a concentration between about 0.1% to about 100%, for example, of riboflavin therein, etc.

In one embodiment, the cross-linked cornea and sclera can be placed in a sterile vial under vacuum, or in a standard storage solution, such as tissue culture medium 199 (M-199) containing 5% dextran 40 for hypothermia, even cryopreservation, and can be kept frozen under very low temperature after ice-free cryopreservation by vitrification of the cross-linked cornea in a high concentration of propane-1,2-diol or liquid nitrogen by stepwise cooling the tissue, etc.

In one embodiment, the cellular components of the corneal stroma may be initially destroyed using enzymatic agents, such as Trypsin, Nucleases, Phospholiphases $A_2$ ($PLA_2$), Sera, all have shortcomings of damaging the basement membrane, such as Bowman's or Descemet's membrane. Although destruction of the cellular elements can be beneficial, alone it is useless since the antigenic component of the stroma that is the collagen is not cross-linked.

In one embodiment, one can destroy the cellular component of the corneal or sclera initially using chemical means, such as Ethanol, Glycerol, acids and alkalis, Peracetic acid, Ammonium hydroxide ionic detergents, Sodium dodecyl sulfate, Sodium deoxycholate non-ionic detergents, zwitterionic detergents, (CHAPS), but all damage the Glycosaminoglycans (GAG) component of the stroma of the cornea or the sclera and do not cross-link the collagen, thus the tissue maintains its antigenicity.

In one embodiment, the corneal stroma or the sclera is exposed to hypo- and hypertonic solutions that are basically harmless, but it is not effective in destroying the cellular elements of the cornea or sclera and does not cross-link the collagen, etc. while maintaining the antigenicity of the tissue.

In one embodiment, the cornea or sclera is exposed to Tris-HCL that eliminates cellular elements and also damages the GAG component of the tissue, and it does not cross-link the collagen.

In one embodiment, the physical means, such as freeze-thawing or snap freezing can be used that damages the cellular elements of the tissue, but also damages the extracellular matrix (ECM) of the tissue without crosslinking the collagen.

In another embodiment, the tissue can be exposed to high ultrasonic energy and frequency that can damage the cells when the cornea is immersed in the fluid and the ultrasonic transducer in also immersed in the solution. This technique and/or exposing the cornea or sclera to high hydrostatic pressure can destroy the cells without damaging the collagen in the stroma or in the sclera, but both techniques do not cross-link the cornea, and the tissues maintain their immunogenicity and create an immune response that encourage immune cell migration and enzymatic destruction of the implant, and the implant is ultimately rejected.

In one embodiment, one can expose the donor cornea or sclera to ultrasonic destruction or high hydrostatic destruction of the cellular elements, then apply a photosensitizer, such as riboflavin, to the tissue immersed in a riboflavin solution that is then radiated with UV radiation or another light to crosslink the cornea or the scleral tissue. Subsequently, the tissue is cleansed in a saline solution to wash out the reactive oxygen species and enzymes that are released by destroying the cells by a simple agitation of the tissue or a low frequency ultrasound. In one embodiment, this ultrasonic technique can be also applied to in vivo corneas or the sclera after their cross-linking with a photosensitizer/UV radiation.

In one embodiment, the cross-linked cornea can be used as an inlay to augment the thickness of the cornea and render it more resilient for refractive surgery procedures.

In one embodiment, the cross-linked cornea is placed over the host cornea using a Shack-Hartmann system or other available instrument to correct the refractive error of the eye with an excimer laser, prior to implantation of the implant inside a corneal pocket.

In one embodiment, the cross-linked cornea or sclera can be used to replace injured lip, nose, or cheek augmentation in cosmetic surgery, chin augmentation, or reconstruction, while the cornea or sclera that is cross-linked maintains its flexibility and softness.

In one embodiment, for eye bank storage, the cornea and/or sclera can be cross-linked (see e.g., FIG. 4B) using a photosensitizer/cross-linker and UV radiation to kill the cellular elements and crosslink the cornea and scleral collagen making them less antigenic while being able to store them for a long time (e.g., greater than 1 year storage) and maintaining the corneal stromal clarity.

In one embodiment, the corneal stroma and/or the sclera can be preserved by the photosensitizer crosslinking technique and kept almost indefinitely if the cross-linked cornea is kept at temperature close to zero, and is sealed in a bottle under vacuum for many years. The cross-linked corneal stroma can be washed with a sterile physiological saline solution to regain its shape and transparency and shaped with a femtosecond laser to any shape lenslet for correction of myopia, hyperopia, and astigmatism while strengthening the cornea by increasing its shape rather than decreasing it as is done with the present photorefractive, or LASIK or SMILE laser procedures. The preserved corneal inlay also can be once again cross-linked or exposed to UV radiation or gamma radiation to completely sterilize it. This procedure prevents post implantation bacteria, fungal parasites, or viral infections seen often after implantation of the partial corneal tissue or inlay where the pathogens can hide in the crevices of the tissue (e.g., inside the cornea) and grow a few days or weeks later producing a difficult to manage endophthalmitis or corneal ulcer.

In one embodiment, the corneal transplant is cross-linked to render the corneal tissue more resilient to expansion as occurs after refractive surgery.

In one embodiment, the photosensitizer (e.g., riboflavin) or other crosslinkers are conjugated with cell penetrating peptides (CPP) or activatable cell penetrating peptides (ACPP) or other cell penetrating agents, such as cyclodextrin, etc. that enhances penetration of the crosslinker in the tissue, saving time for surgery if the crosslinking is done on a patient, or if the crosslinking is done for the storage of the tissue.

In one embodiment, the photosensitizer formulation permits faster penetration of the crosslinker inside the corneal transplant, thus reducing the operative time less than ½, ⅓, ⅕ or less than ⅒ of the time that it would take to cross-link the corneal tissue as done by the standard procedure.

In one embodiment, the crosslinkers are made in the form of nanoparticles, such as dendrimers, and can be organic, non-organic, metallic, such as gold, iron or ferric oxide or zinc, silver, silica, graphene, carbon nanotubes, nanowires, quantum dots (QDs), etc. or coated with lipids, or an antibody that encourages the cell penetration, etc.

In one embodiment, the crosslinker is conjugated with CPP and antibody against a bacterium, fungi, viruses, prions, parasites, attached to either metallic or organic nanoparticles, such as a carbon nanospheres or nanotubes, or gold or silver or zinc nanoparticles, etc. and CPP, and radiated with UV light or other wavelengths of light that is absorbed by the nanoparticles and the photosensitizer heats up the nanoparticle/pathogens complex creating thermal damage to the pathogens in addition to being cross-linked by the photosensitizer. The use of UV radiation, in addition, damages the genetic components of the pathogens along with the medication that kills the pathogens or makes them more sensitive to the medication to which the pathogens would not be sensitive normally or were resistant, such as methicillin-resistant *Staphylococcus aureus* (MRSA) bacteria, after administering the crosslinker complex locally or topically.

In one embodiment, the antibody-coated nanoparticles can be attached to the antimicrobial peptides, and the crosslinker is applied topically to the eye, lid, skin or mucosa, or any reachable infection even with a fiber optic (e.g., in the lung, eye, bladder, vagina, uterus, throat, nose, or exposed tumor) as needed and radiated with UV light to crosslink the protein of the bacteria and kill them along with potentially a cancerous lesion or cells.

In one embodiment, the process of crosslinking using UV radiation creates singlet oxygen and reactive oxygen species in the presence of the oxygen that crosslinks the proteins, including those present in the bacteria, fungi, viruses, prions, and parasites, thereby killing them, and in case of the cornea or the sclera, crosslinks the collagens in the tissue and makes then less immunogenic.

In one embodiment, the corneal tissue is cross-linked to be used in refractive surgery as a corneal inlay to change the refractive power of the cornea. In another embodiment, it replaces the damaged corneal tissue. In yet another embodiment, the cross-linked cornea or sclera can be used as a tissue filler or provide a shape for the surrounding tissue structures, such as in cosmetic surgery in the face, replacement for the damaged lids, reconstructing the facial appearance, etc. In still another embodiment, it can serve as a protecting container to prevent immune response to the cells, etc. inside the container or can be used as a reservoir for drug delivery etc.

In one embodiment, the cross-linked cornea or sclera is co-cultured in a medium having nanoparticles/CPP or lipids that penetrates the tissues scaffold, and the nanoparticles are made of polylactic, polyglycolic or polycaprolactone of silicon nanoparticles conjugated with one or more medications (e.g., anti-inflammatory agents, steroids, NSAIDs, anti-proliferative agents, immunosuppressives, such as cyclosporine, mycophenolic acid, antibiotics, anti-glaucoma agents, such as prostaglandin analogues, Rock inhibitors, such as Fasudil, rhopressa, etc., anti-integrins, Wnt inhibitors, or GSK inhibitors, anti-VEGFs, or combinations thereof). The cross-linked cornea or sclera can be cut to any size or thickness (e.g., 10 microns to 1 millimeter and more) be radius shaped, circular, rectangular, etc. to release the medication depending on the bio-degradation of polymeric nanoparticles. The implant can be implanted anywhere in the eye (see e.g., FIG. 4E).

In one embodiment, the cross-linked cornea or sclera is made any desired shape and thickness using a femtosecond laser or an excimer laser, and using the same lasers one can punch partial or full thickness holes in the implant, so that after penetration of the nanoparticles, the release time will depend on the number and the size of the holes created inside the cross-linked cornea ranging from 1 month to few years, the cross-linked cornea or sclera is then co-cultured in a medium having nanoparticles/CPP or lipids that penetrate the tissues scaffold and nanoparticles are made of polylactic, polyglycolic or polycaprolactone of silicon nanoparticles conjugated with medications (e.g., anti-inflammatory agents, steroids, NSAIDs, anti-proliferative agents, immunosuppressives, such as cyclosporine, mycophenolic acid, antibiotics, anti-glaucoma agents, such as prostaglandin analogues, Rock inhibitors, such as Fasudil, rhopressa, etc., anti-integrins, Wnt inhibitors, or GSK inhibitors, anti-VEGFs, or a combination thereof). The cross-linked cornea or sclera can be cut to any size or thickness (e.g., 10 microns to 1 millimeter and more), be radius shaped, circular, rectangular, etc. to release the medication depending on the bio-degradation of polymeric nanoparticles. The implant can be implanted anywhere in the eye or enhanced its release by a focused ultrasound.

In one embodiment, the scleral tissue is cross-linked for long term storage.

In one embodiment, the photosensitizer, such as riboflavin, is in a physiological solution with osmolarities of 200 mOsm/L to 400 mOsm/L, or preferably about 300 mOsm/L.

In one embodiment, the pH of the solution is between 6-8 pH or preferably 7.4 pH.

In one embodiment, the photosensitizer solution contains dextran of 0.1%-3%.

In one embodiment, the photosensitizer/nanoparticle solution can contain low molecular weight heparin or hyaluronic acid or chondroitin sulfate, etc., the low molecular weight heparin enhances the killing of the bacteria in vitro and in vivo after topical application and irradiation with UV light or other light. These preparations can be used for treatment of bacterial, fungi, viral, parasitic keratitis or conjunctivitis.

The crosslinking of the tissue is done when the photosensitizer is radiated with a light wavelength of ultraviolet to infrared depending on the photosensitizer that absorbs the light beam. In one embodiment, the photosensitizer solution can, in addition, contain some additives, such as antibiotics, antifungals, antivirals, and/or anti-parasites.

In one embodiment, the corneal crosslinker is conjugated with CPP, nanoparticles applied to the cornea and irradiated with UV light or other light to kill all cellular elements of the cornea and sclera and crosslink the collagen, and sterilize the corneal implant for storage prior to its use.

In one embodiment, for the cross-linked corneal storage (CCS), the corneal crosslinker is conjugated with CPP, antibody-coated metallic nanoparticles, such as gold nanoparticles, etc. When the implant is completely penetrated by the crosslinker, it is radiated with UV light or other light wavelengths to kill the bacteria by thermal energy, and the crosslinking kills bacteria, fungi, parasites, viruses and prions for corneal storage prior to its use.

In still a further embodiment, the photosensitizer is conjugated with one or more metallic or non-metallic nanoparticles and/or one or more antibody-coated nanoparticles, and the one or more nanoparticles and/or one or more antibody-coated nanoparticles are further conjugated with one or more cell penetrating peptides (CPP) and/or activatable-cell penetrating peptides (ACPP), thereby forming a photosensitizer-nanoparticle-CPP/ACPP complex for facilitating an enhanced penetration of the photosensitizer into a corneal stroma and stromal cells of the host cornea with or without the use of low intensity ultrasound to kill the stromal cells after UV radiation.

In a further embodiment of the present invention, the step of cross-linking the corneal implant prior to implantation of the cornea comprises the substeps of: (a) applying a photosensitizer to the cornea so as to penetrate the entire corneal implant; (b) irradiating the cornea with ultraviolet light so as to activate cross-linkers in the cornea and thereby crosslink the entire corneal implant; (c) cutting the cross-linked cornea to the desired shape or dioptric power; (d) creating a pocket in the recipient cornea; and (e) implanting the cross-linked cornea inside the corneal pocket along with a lubricating substance, such as hyaluronic acid, etc.

In one embodiment, the corneal inlay is implanted as above, then cross-linked with a photosensitizer injected inside the corneal pocket to penetrate the implant and the wall of the corneal pocket, and then the cornea and the inlay are simultaneously cross-linked. Followed by copious washing of the cornea with saline and/or an anti-inflammatory agent, such as steroid, NSAIDs, or Rock inhibitors, anti-integrins, or GSK inhibitors or Wnt inhibitors.

In still a further embodiment, the photosensitizer is conjugated with one or more nanoparticles and/or one or more antibody-coated nanoparticles, and the one or more nanoparticles and/or one or more antibody-coated nanoparticles are further conjugated with an antimicrobial peptide that damages the bacterial cell membrane while the normal cells are not affected, and one or more cell penetrating peptides (CPP) and/or activatable-cell penetrating peptides (ACPP), and thereby forming a photosensitizer-nanoparticle-CPP/ACPP complex for facilitating an enhanced penetration of the photosensitizer into a corneal stroma and stromal cells of the host cornea to kill the stromal cells. The preparation is administered inside an infected corneal pocket of a large abscess, of nasolacrimal duct, or the lid, or skin or mucosa and irradiated with the light to activate the photosensitizer and kill all organisms while protecting the normal tissue.

In still a further embodiment, the photosensitizer is conjugated with one or more antibody-coated nanoparticles or dendrimers, and the one or more antibody-coated nanoparticles or dendrimers are further conjugated with one or more cell penetrating peptides (CPP) and/or activatable-cell penetrating peptides (ACPP), thereby forming a photosensitizer-antibody-coated nanoparticle or dendrimer-CPP/ACPP complex; and the method further comprises the steps of: (iv) administering the photosensitizer-antibody-coated nanoparticle or dendrimer-CPP/ACPP complex topically or by injection to the host cornea, the photosensitizer being absorbed by bacteria, viruses, fungi, and/or protozoa present in an infected corneal ulcer of the host cornea; and (v) irradiating the host cornea with light so as to kill the bacteria, viruses, fungi, or protozoa by cross-linking the cytoplasmic proteins of the bacteria, viruses, fungi, and/or protozoa by thermal energy and crosslinking of the proteins of the micro-organisms, viruses, and/or prions, and sterilizing the entire cross-linked corneal and scleral implant's thickness and killing all pathogens and cells in the implant and cleansed with a physiological solution to wash out the toxins and the debris in the tissue.

In one embodiment, the antimicrobial peptides are from the group of chemotactic peptides having inflammatory and antimicrobial activity, such as polybia-CP (Pol-CP-NH$_2$: Ile-Leu-Gly-Thr-Ile-Leu-Gly-Leu-Leu-Lys-Ser-Leu-NH$_2$), Pol-CP-NH$_2$, and protonectin and polybia-MPI, linear cationic amphipathic AMPs, or wasp *Polybia paulista.*

In one embodiment, when the patient suffers from an infected corneal ulcer, or skin ulcer, or mucosa ulcer, the crosslinker is conjugated with CPP, antibiotics, antifungals, anti-parasites, antivirals etc. and the antibody-coated metallic nanoparticles, such as gold nanoparticles, and the ulcer is treated with a topical application of the crosslinker complex to the ulcer, followed by UV radiation or other light wavelengths to kill the bacteria/fungi parasites, or viruses, etc. by thermal energy, medication, and crosslinking the proteins of the bacteria, fungi, parasites, viruses, while crosslinking the cornea or the skin to resist enzymatic degradation and healing the infected ulcer.

In one embodiment, corneal crosslinking is performed with CPP, antibody-coated metallic gold nanoparticles and antibiotics and/or antimicrobial proteins, etc. using UV or other light wavelengths to kill the bacteria by thermal energy and crosslinking. The thermal energy and crosslinking kills bacteria, fungi, parasites, viruses and prions, and their infectious pathogens, such as viral infections, such as hepatitis B, West Nile virus, Chagas disease, and prion agents.

In one embodiment, scleral crosslinking with CPP, nanoparticles using UV light or other wavelengths of light kills all cellular elements of the cornea and/or sclera, and cross-links the collagen, and sterilizes the implant.

In one embodiment, scleral crosslinking with CPP, antibody-coated metallic gold nanoparticles, etc. using UV light or other light wavelengths kills the bacteria, fungi, parasites, viruses and prions by thermal energy and crosslinking.

In one embodiment, scleral crosslinking with CPP, antibody-coated metallic gold nanoparticles and antibiotics and/or antimicrobial proteins, etc. using UV or other light wavelengths kills the bacteria, fungi, viruses and prions by thermal energy and crosslinking, and subsequently, the tissue is washed with a physiologic solution and exposed to low frequency ultrasound to cleanse the tissue toxins released by killing the bacteria, fungi, viruses, prions, or parasites.

In one embodiment, after storage of the cross-linked cornea or sclera, if the cross-linked tissue appears swollen, it can be treated with a physiological solution containing antibiotics, deturgescent agents like dextran 4-8%, and chondroitin sulphate, resulting in deswelling of the cornea or the sclera.

In one embodiment, the cross-linked tissue after long term storage can be re-sterilized with gamma radiation.

In one embodiment, the corneas can be stored using standard techniques while suspended in 80 ml Eagle's MEM containing HEPES buffer, 26 mmol/l NaHCO$_3$, 2% FBS, 2 mmol/l L-glutamine, penicillin, streptomycin and amphotericin B, and stored at 34° C. for 1-7 days, then, if they have not used for corneal transplantation, they can now prepared as described above for crosslinking or the cornea and sclera, which can be then stored for greater than 1 year, etc.

In one embodiment, the cross-linked cornea is denuded from corneal epithelial cells and endothelial cells while keeping the Descemet's membrane co-cultured with stem cells, or endothelial stem cells, or pre-corneal conjunctival stem cells, or mesenchymal stem cells of the potentially host patient with polymeric anti-inflammatory nanoparticles of PLA, PLA GLA having Rock inhibitors, anti-integrins, GSK inhibitors, and/or immunosuppressive agents combined with electrophoresis tissue penetration in the implant and/or followed with medical treatment using topical antibiotics, anti-inflammatory compounds, such as Rock inhibitors, anti-integrins, GSK inhibitors, and/or immunosuppressive agents.

In one embodiment, the cross-linked cornea is denuded from corneal epithelial cells and endothelial cells while keeping the Descemet's membrane co-cultured with stem cells, or endothelial stem cells, or pre-corneal conjunctival stem cells, or mesenchymal stem cells of the potentially host patient and polymeric nanoparticles conjugated with anti-inflammatory compounds, such as Rock inhibitors, anti-integrins, GSK inhibitors, and/or immunosuppressive agents, such as cyclosporine, mycophenolic acid, tacrolimus, combined with electrophoresis tissue penetration in the cross-linked implant etc. to release the medication after implantation for a long time after implantation.

In one embodiment, the cross-linked cornea is denuded from corneal epithelial cells and endothelial cells while keeping the Descemet's membrane co-cultured with stem cells, endothelial stem cells, and transfection with transcription factors such as E2F2, which has been reported to stimulate cell-cycle progression and endothelial cell replication to grow endothelial cells on the Descemet's membrane for transplantation in a patient. The technology can be used as Descemet stripping automated endothelial keratoplasty (DSEK) or Descement membrane endothelial keratoplasy (DMEK) or deep lamellar keratoplasty (DLK) for partial transplantation of the cornea that is now cross-linked with or without corneal endothelial cells as known in the art, simplifying the 3-D printing of the cornea, for the transplantation, since one has now a resilient cross-linked cornea to work with, and the process can be made simple by manufacturing all the tissues except for growing endothelial cells on the back of a cross-linked cornea with its Descemet's membrane intact, thus reducing the chance of the rejection since the corneal stroma part of the transplant is cross-linked and will not induce an immune response in the host followed after implantation with topical or subconjunctival medical treatment using antibiotics, anti-inflammatory compounds, such as Rock inhibitors, anti-integrins, GSK inhibitors, and/or immunosuppressive agents.

In one embodiment, one can use a combination or cross-linked cornea or cross-linked animal cornea or genetically engineered animal cornea to grow corneal endothelial cells prior to their implantation in DSEK or DMEK, since the cross-linked corneal stromas are not immunogenic. The cross-linked tissue is co-cultured with a medium having nanoparticles/CPP or lipids that penetrates the tissue scaffolds and the nanoparticles are made of polylactic, polyglycolic or polycaprolactone or silicon nanoparticles conjugated with medications, such as anti-inflammatory agents, steroids, NSAID, anti-proliferative agents, immunosuppressives, such as cyclosporine, mycophenolic acid, antibiotics, anti-glaucoma agents, such as prostaglandin analogues, Rock inhibitors, such as Fasudil, rhopressa, etc., anti-integrins, Wnt inhibitors, or GSK inhibitors, anti-VEGFs, or combinations thereof combined with or without electrophoresis tissue penetration in the implant thereof, to release the medication after implantation depending on the bio-degradation of polymeric nanoparticles.

In one embodiment, one can use a combination or cross-linked cornea or cross-linked animal cornea or genetically engineered animal cornea to grow corneal endothelial cells prior to their implantation in DSEK or DMEK since the cross-linked corneal stromas are not immunogenic. The cross-linked tissue is co-cultured with a medium having nanoparticles/CPP or lipids that penetrates the tissue scaffolds and the nanoparticles are made of polylactic, polyglycolic or polycaprolactone or silicon nanoparticles conjugated with medications, such as anti-inflammatory agents, steroids, NSAIDs, anti-proliferative agents, immunosuppressives, such as cyclosporine, mycophenolic acid, antibiotics, anti-glaucoma agents, such as prostaglandin analogues, Rock inhibitors, such as Fasudil, rhopressa, etc., anti-integrins, Wnt inhibitors, or GSK inhibitors, anti-VEGFs, or combinations thereof and the tissue is exposed to low intensity ultrasound to enhance penetration of the nanoparticles in the implant and to release the medication after implantation slowly, depending on the bio-degradation of polymeric nanoparticles to release the medication after implantation depending on the bio-degradation of polymeric nanoparticles.

In one embodiment, one can use a combination or cross-linked cornea or cross-linked animal cornea or genetically engineered animal cornea to grow corneal endothelial cells prior to their implantation in DSEK or DMEK since the cross-linked corneal stromas are not immunogenic. The cross-linked tissue is co-cultured with a medium having nanoparticles/CPP or lipids that penetrates the tissue scaffolds and nanoparticles are made of polylactic, polyglycolic or polycaprolactone or silicon nanoparticles conjugated with medications, such as anti-inflammatory agents, steroids, NSAIDs, anti-proliferative agents, immunosuppressives, such as cyclosporine, mycophenolic acid, antibiotics, anti-glaucoma agents, such as prostaglandin analogues, Rock inhibitors, such as Fasudil, rhopressa, etc., anti-integrins, Wnt inhibitors, or GSK inhibitors, anti-VEGFs, or their combination, and the tissue is exposed to low intensity ultrasound to enhance penetration of the nanoparticles in the implant and to release the medication after implantation slowly, depending on the bio-degradation of polymeric nanoparticles.

In one embodiment, the cross-linked cornea can be re-cellularized by either injecting appropriate stem cells inside the cross-linked implant, or after implantation, encouraging stem cells, such as mesenchymal cells migration from the adjacent tissue. In either case, the topical administration of nerve growth factors alone or Rock inhibitors alone, or a combination of them encourage cell migration and migration of nerve azons in the cross-linked graft.

In one embodiment, the epithelial cells can be seeded on the cross-linked Bowman's membrane or the endothelial cells seeded on the Descemet's membrane prior or after implantation.

In one embodiment, the corneal or scleral graft can be built using a standard 3-D printing technique using the cross-linked cornea or a part of it as a base in addition to use of one or the other polymeric materials such as Silk sericin, Poly(vinyl alcohol), Poly(2-hydroxyethyl methacrylate), Polyethylene (glycol) diacrylate, Poly(lactic-co-glycolic acid), Poly(ethylene glycol), Poly(acrylic acid), Poly(glycerol sebacate), Poly(ester urethane) urea, Peptide amphiphiles, naturally/synthetically derived, m Arginine-glycine-aspartic acid, the cellular elements of the cornea can be added subsequently in the tissue culture, such a hybrid cornea can renders itself to modification of its refractive power after implantation or before implantation, using low energy level pulses of a femtosecond laser.

Any of the features, attributes, or steps of the above described embodiments and variations can be used in combination with any of the other features, attributes, and steps of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A method of corneal or scleral inlay crosslinking and preservation, the method comprising the steps of:
   cross-linking at least a portion of a donor cornea or a donor sclera so as to kill cellular elements in the portion of the donor cornea or the donor sclera, and make the portion of the donor cornea or the donor sclera less antigenic to a body portion of a recipient patient in which the portion of the donor cornea or the donor sclera is to be implanted;
   storing the cross-linked donor cornea or the donor sclera for a long period of time prior to implanting the portion of the donor cornea or the donor sclera into the body portion of the recipient patient;
   forming cavities or holes in the portion of the cross-linked donor cornea or the donor sclera using a laser so that the portion of the donor cornea or the donor sclera is capable of being used for sustained drug delivery; and
   co-culturing the donor cornea or the donor sclera in a medium having nanoparticles conjugated with one or more medications and cell penetrating peptides (CPP) or lipids that penetrate the tissue scaffolds formed by the cavities or holes in the portion of the donor cornea or the donor sclera, the portion of the donor cornea or the donor sclera configured to be used for sustained drug delivery when the portion of the donor cornea or the donor sclera is implanted in the body portion of the recipient patient.

2. The method according to claim 1, wherein the step of cross-linking the portion of the donor cornea or the donor sclera comprises the substeps of:
   applying a photosensitizer to the portion of the donor cornea or the donor sclera so as to penetrate the tissue of the donor cornea or the donor sclera; and
   irradiating the portion of the donor cornea or the donor sclera with ultraviolet light so as to cross-link collagen in the portion of the donor cornea or the donor sclera so as to make the portion of the donor cornea or the donor sclera less antigenic to the body portion of the recipient patient in which the portion of the donor cornea or the donor sclera is to be implanted.

3. The method according to claim 2, wherein the photosensitizer comprises riboflavin and a cell penetrating agent, and wherein the portion of the donor cornea or the donor sclera is irradiated by using a laser emitting the ultraviolet light.

4. The method according to claim 3, wherein the cell penetrating agent comprises one or more nanoparticles conjugated with one or more cell penetrating peptides (CPP) and/or activatable-cell penetrating peptides (ACPP).

5. The method according to claim 4, wherein the method further comprises the steps of:
   implanting the portion of the donor cornea into a host cornea of the recipient patient; and
   applying low intensity focused ultrasound to stromal cells of the host cornea of the recipient patient so as to kill the stromal cells of the host cornea.

6. The method according to claim 1, wherein the step of storing the cross-linked donor cornea or the donor sclera for a long period of time comprises storing the cross-linked donor cornea or the donor sclera for a time period of one year or more.

7. The method according to claim 1, wherein, prior to the step of cross-linking at least a portion of the donor cornea or the donor sclera, the method comprises the steps of:
   dissecting and removing all of the soft tissue from a donor eye so to leave only the donor cornea and/or the donor sclera, the removed soft tissue of the donor eye comprising the conjunctiva, muscles, retina, choroid, iris, ciliary body, and optic nerve; and
   cleansing the donor cornea and/or the donor sclera in a physiological solution so as to prepare the donor cornea and/or the donor sclera for cross-linking.

8. The method according to claim 1, further comprising the step of:
   cutting and shaping the donor cornea using a cutting instrument so as to form a lens having a desired thickness, shape, and diameter; the lens comprising a plus lens, a minus lens, an astigmatic lens, or a combination thereof.

9. The method according to claim 1, wherein, prior to the step of cross-linking at least a portion of the donor cornea or the donor sclera, the method comprises the step of:
   exposing the donor cornea or the donor sclera to a high intensity ultrasonic or hydrostatic force so as to destroy the cellular elements in the portion of the donor cornea or the donor sclera; and
   wherein, after the step of cross-linking at least a portion of the donor cornea or the donor sclera, the method comprises the step of:
   cleansing the donor cornea and/or the donor sclera in a saline solution to remove the reactive oxygen species and enzymes released from the destroyed cellular elements by mechanical agitation of the donor cornea or the donor sclera or by applying a low frequency ultrasound to the donor cornea or the donor sclera.

10. The method according to claim 1, wherein the method further comprises the step of:
    implanting the portion of the donor cornea or the donor sclera in the body of the recipient patient to replace an injured chin, lip, nose, or cheek; or in cosmetic surgery, to augment a chin, lip, nose, or cheek.

11. The method according to claim 1, wherein the step of cross-linking the portion of the donor cornea or the donor sclera comprises the substeps of:
    applying a photosensitizer comprising riboflavin to the donor cornea or the donor sclera so as to penetrate the tissue of the donor cornea or the donor sclera; and
    irradiating the donor cornea or the donor sclera with ultraviolet light so as to sterilize the donor cornea or the donor sclera.

12. The method according to claim 1, wherein the nanoparticles are formed from polylactic, polyglycolic, polycaprolactone, and/or silicon; and wherein the one or more medications are selected from the group consisting of anti-inflammatory agents, steroids, nonsteroidal anti-inflammatory drugs (NSAIDs), anti-proliferative agents, immunosuppressives, antibiotics, anti-glaucoma agents, Rock inhibitors, anti-integrins, Wnt inhibitors, GSK inhibitors, anti-vascular endothelial growth factors (anti-VEGFs), and combinations thereof.

13. The method according to claim 1, wherein the step of cross-linking the portion of the donor cornea or the donor sclera comprises the substeps of:
    applying riboflavin to the portion of the donor cornea or the donor sclera so as to penetrate the tissue of the donor cornea or the donor sclera; and
    irradiating the portion of the donor cornea or the donor sclera using a laser emitting ultraviolet light so as to cross-link collagen in the portion of the donor cornea or the donor sclera so as to make the portion of the donor cornea or the donor sclera less antigenic to the body portion of the recipient patient in which the portion of the donor cornea or the donor sclera is to be implanted.

14. The method according to claim 13, wherein, prior to the step of cross-linking the portion of the donor cornea or the donor sclera with the riboflavin and the ultraviolet light, the method comprises the step of:

using chemical means or mechanical means to destroy the cellular elements in the portion of the donor cornea or the donor sclera.

15. The method according to claim 14, wherein the chemical means for destroying the cellular elements in the portion of the donor cornea or the donor sclera are selected from the group consisting of ethanol, glycerol, acids, alkalis, peracetic acid, ammonium hydroxide ionic detergents, sodium dodecyl sulfate, sodium deoxycholate non-ionic detergents, zwitterionic detergents, non-ionic surfactants, benzalkonium chloride, non-ionic non-denaturing detergents, genipin, and combinations thereof.

16. The method according to claim 14, wherein the mechanical means for destroying the cellular elements in the portion of the donor cornea or the donor sclera comprises applying low intensity focused ultrasound to the portion of the donor cornea or the donor sclera.

17. A method of corneal or scleral implantation associated with an infection, the method comprising the steps of:

applying a photosensitizer conjugated with one or more antibody-coated metallic nanoparticles, one or more cell penetrating peptides (CPP), and one or more medications to a host eye of a recipient patient having an infected corneal ulcer or scleral infection, the one or more medications selected from the group consisting of antibiotics, antifungals, anti-parasites, antivirals, and combinations thereof; and irradiating the area of the host eye having the infected corneal ulcer or the scleral infection with ultraviolet light so as to kill bacteria, fungi, parasites, and/or viruses while cross-linking the area of the host eye to resist enzymatic degradation and heal the infected corneal ulcer or the scleral infection.

18. A method of corneal or scleral inlay crosslinking and preservation, the method comprising the steps of:

using mechanical means to destroy cellular elements in at least a portion of a donor cornea or a donor sclera, wherein the mechanical means for destroying the cellular elements in the portion of the donor cornea or the donor sclera comprises applying low intensity focused ultrasound to the portion of the donor cornea or the donor sclera;

cross-linking the portion of the donor cornea or the donor sclera so as to further kill cellular elements in the portion of the donor cornea or the donor sclera, and make the portion of the donor cornea or the donor sclera less antigenic to a body portion of a recipient patient in which the portion of the donor cornea or the donor sclera is to be implanted, wherein cross-linking the portion of the donor cornea or the donor sclera further comprises:

applying riboflavin to the portion of the donor cornea or the donor sclera so as to penetrate the tissue of the donor cornea or the donor sclera; and irradiating the portion of the donor cornea or the donor sclera using a laser emitting ultraviolet light so as to cross-link collagen in the portion of the donor cornea or the donor sclera so as to make the portion of the donor cornea or the donor sclera less antigenic to the body portion of the recipient patient in which the portion of the donor cornea or the donor sclera is to be implanted; and storing the cross-linked donor cornea or the donor sclera for a long period of time prior to implanting the portion of the donor cornea or the donor sclera into the body portion of the recipient patient.

19. A method of corneal or scleral inlay crosslinking and preservation, the method comprising the steps of:

cross-linking at least a portion of a donor cornea or a donor sclera so as to kill cellular elements in the portion of the donor cornea or the donor sclera, and make the portion of the donor cornea or the donor sclera less antigenic to a body portion of a recipient patient in which the portion of the donor cornea or the donor sclera is to be implanted, wherein cross-linking the portion of the donor cornea or the donor sclera further comprises:

applying a photosensitizer to the portion of the donor cornea or the donor sclera so as to penetrate the tissue of the donor cornea or the donor sclera, the photosensitizer comprising riboflavin and a cell penetrating agent, the cell penetrating agent comprising one or more nanoparticles conjugated with one or more cell penetrating peptides (CPP) and/or activatable-cell penetrating peptides (ACPP); and irradiating the portion of the donor cornea or the donor sclera using a laser emitting ultraviolet light so as to cross-link collagen in the portion of the donor cornea or the donor sclera so as to make the portion of the donor cornea or the donor sclera less antigenic to the body portion of the recipient patient in which the portion of the donor cornea or the donor sclera is to be implanted; and storing the cross-linked donor cornea or the donor sclera for a long period of time prior to implanting the portion of the donor cornea or the donor sclera into the body portion of the recipient patient.

\* \* \* \* \*